United States Patent
Wang et al.

(10) Patent No.: US 11,377,449 B2
(45) Date of Patent: Jul. 5, 2022

(54) BTK INHIBITORS WITH IMPROVED DUAL SELECTIVITY

(71) Applicant: BEIGENE, LTD., Grand Cayman (KY)

(72) Inventors: Zhiwei Wang, Beijing (CN); Yunhang Guo, Beijing (CN); Desheng Yu, Beijing (CN)

(73) Assignee: BEIGENE, LTD., Grand Cayman (KY)

( * ) Notice: Subject to any disclaimer, the term of this patent is extended or adjusted under 35 U.S.C. 154(b) by 4 days.

(21) Appl. No.: 16/637,615

(22) PCT Filed: Aug. 12, 2018

(86) PCT No.: PCT/CN2018/100145
§ 371 (c)(1),
(2) Date: Feb. 7, 2020

(87) PCT Pub. No.: WO2019/034009
PCT Pub. Date: Feb. 21, 2019

(65) Prior Publication Data
US 2020/0181150 A1    Jun. 11, 2020

(30) Foreign Application Priority Data

Aug. 12, 2017 (WO) ................ PCT/CN2017/097291

(51) Int. Cl.
| A61P 35/00 | (2006.01) |
| A61P 37/00 | (2006.01) |
| C07D 519/00 | (2006.01) |
| C07D 487/04 | (2006.01) |
| C07D 487/14 | (2006.01) |
| C07D 471/14 | (2006.01) |

(52) U.S. Cl.
CPC ......... *C07D 487/04* (2013.01); *C07D 471/14* (2013.01); *C07D 487/14* (2013.01); *C07D 519/00* (2013.01)

(58) Field of Classification Search
CPC ........ A61P 35/00; A61P 37/00; C07D 519/00; C07D 487/04; C07D 487/14; C07D 471/14
See application file for complete search history.

(56) References Cited

U.S. PATENT DOCUMENTS

| 7,393,848 | B2 | 7/2008 | Currie et al. |
| 7,514,444 | B2 | 4/2009 | Honigberg et al. |
| 7,718,662 | B1 | 5/2010 | Chen et al. |
| 8,084,620 | B2 | 12/2011 | Liu et al. |
| 8,735,553 | B1 | 5/2014 | Li et al. |
| 9,447,106 | B2 | 9/2016 | Wang et al. |
| 9,556,188 | B2 | 1/2017 | Wang et al. |
| 10,005,782 | B2 | 6/2018 | Wang et al. |
| 10,570,139 | B2 | 2/2020 | Wang et al. |
| 10,927,117 | B2 | 2/2021 | Wang et al. |
| 2002/0094989 | A1 | 7/2002 | Hale et al. |
| 2006/0178367 | A1 | 8/2006 | Currie et al. |
| 2006/0183746 | A1 | 8/2006 | Currie et al. |
| 2008/0076921 | A1 | 3/2008 | Honigberg et al. |
| 2008/0139582 | A1 | 6/2008 | Honigberg et al. |
| 2009/0105209 | A1 | 4/2009 | Dewdney et al. |
| 2009/0318441 | A1 | 12/2009 | Brain et al. |
| 2010/0004231 | A1 | 1/2010 | Dewdney et al. |
| 2010/0016296 | A1 | 1/2010 | Singh et al. |
| 2010/0016301 | A1 | 1/2010 | Dewdney et al. |
| 2010/0029610 | A1 | 2/2010 | Singh et al. |
| 2010/0035841 | A1 | 2/2010 | Jankowski et al. |
| 2010/0087464 | A1 | 4/2010 | Mi et al. |
| 2010/0105676 | A1 | 4/2010 | Liu et al. |
| 2010/0144705 | A1 | 6/2010 | Miller |
| 2010/0160292 | A1 | 6/2010 | Whitney et al. |
| 2010/0160303 | A1 | 6/2010 | Liu et al. |
| 2010/0222325 | A1 | 9/2010 | Berthel et al. |
| 2010/0249092 | A1 | 9/2010 | Singh et al. |
| 2010/0254905 | A1 | 10/2010 | Honigberg et al. |
| 2011/0118233 | A1 | 5/2011 | Blomgren et al. |
| 2011/0124640 | A1 | 5/2011 | Liu et al. |
| 2011/0224235 | A1 | 9/2011 | Honigberg et al. |
| 2011/0301145 | A1 | 12/2011 | Barbosa, Jr. et al. |
| 2012/0028981 | A1 | 2/2012 | Miller |
| 2012/0040961 | A1 | 2/2012 | Gray et al. |
| 2012/0053189 | A1 | 3/2012 | Loury |
| 2012/0058996 | A1 | 3/2012 | Liu et al. |
| 2012/0077832 | A1 | 3/2012 | Witowski et al. |
| 2012/0082702 | A1 | 4/2012 | DeLucca et al. |
| 2012/0129852 | A1 | 5/2012 | Duan et al. |
| 2012/0157442 | A1 | 6/2012 | Bui et al. |
| 2012/0157443 | A1 | 6/2012 | Bui et al. |
| 2012/0232054 | A1 | 9/2012 | Moriarty et al. |
| 2013/0079327 | A1 | 3/2013 | Yamamoto et al. |

(Continued)

FOREIGN PATENT DOCUMENTS

| GB | 1412017 | 10/1975 |
| JP | H 07-278148 A | 10/1995 |

(Continued)

OTHER PUBLICATIONS

Extended European Search Report for European Application No. 18744173.8, dated Oct. 21, 2020, 12 pages.
Balbach, S. et al., "Pharmaceutical evaluation of early development candidates the 100 mg-approach," International Journal of Pharmaceutics, 275 (2004), pp. 1-12.
Kersseboom, R. et al., "Constitutive activation of Bruton's tyrosine kinase induces the formation of autoreactive IgM plasma cells," Eur. J. Immunol. 40:2643-2654, 2010.
Luo, J. et al., "Modern Physical Pharmaceutics Theory and Practice," Shang Hai Science and Technology Literature Publishing House, Apr. 2005, pp. 293-295.
Singhal, D. et al., "Drug polymorphism and dosage form design: a practical perspective," Advanced Drug Delivery Reviews, 56 (2004) pp. 335-347.

(Continued)

*Primary Examiner* — Sun Jae Yoo
(74) *Attorney, Agent, or Firm* — Cooley LLP

(57) ABSTRACT

Disclosed herein is a tri-substituted phenyl Btk inhibitors with improved dual selectivity, a method and a composition for inhibiting Btk and treating disease associated with undesirable Btk activity (Btk-related diseases).

22 Claims, 3 Drawing Sheets

(56) References Cited

U.S. PATENT DOCUMENTS

Figure 1A:
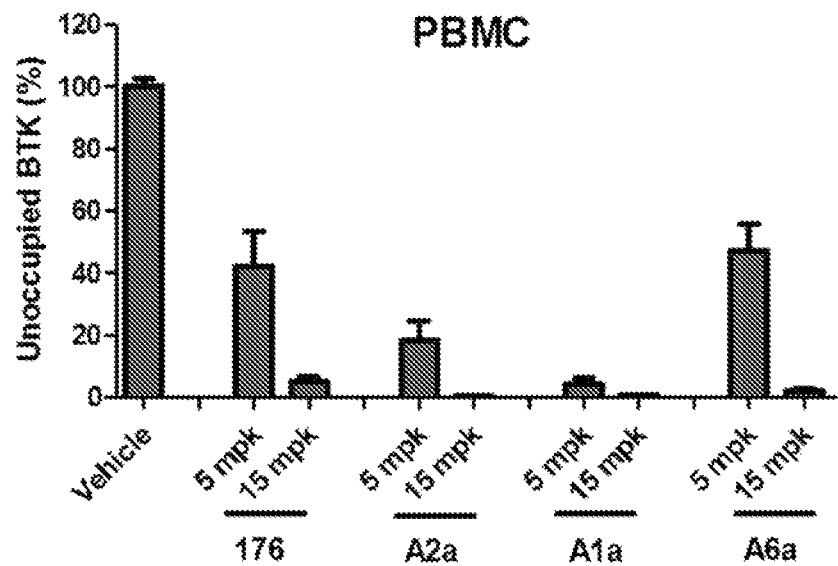

| | | |
|---|---|---|
| 2013/0096118 A1 | 4/2013 | Liu et al. |
| 2013/0116213 A1 | 5/2013 | Cha et al. |
| 2013/0261103 A1 | 10/2013 | Currie et al. |
| 2013/0281432 A1 | 10/2013 | Currie et al. |
| 2014/0045833 A1 | 2/2014 | Laurent et al. |
| 2014/0094459 A1 | 4/2014 | Goldstein et al. |
| 2014/0107151 A1 | 4/2014 | Goldstein et al. |
| 2014/0162983 A1 | 6/2014 | Hodous et al. |
| 2014/0221398 A1 | 8/2014 | Goldstein et al. |
| 2014/0243306 A1 | 8/2014 | Heng et al. |
| 2015/0079109 A1 | 3/2015 | Li et al. |
| 2015/0259354 A1 | 9/2015 | Wang et al. |
| 2015/0315274 A1 | 11/2015 | Li et al. |
| 2016/0083392 A1 | 3/2016 | Wang et al. |
| 2017/0073349 A1 | 3/2017 | Wang et al. |
| 2018/0251466 A1 | 9/2018 | Wang et al. |
| 2019/0169201 A1 | 6/2019 | Wang et al. |
| 2020/0148690 A1 | 5/2020 | Wang et al. |
| 2020/0368237 A1 | 11/2020 | Hilger et al. |
| 2021/0130363 A1 | 5/2021 | Wang et al. |
| 2021/0275530 A1 | 9/2021 | Hu et al. |
| 2021/0332049 A1 | 10/2021 | Guo et al. |

FOREIGN PATENT DOCUMENTS

| | | |
|---|---|---|
| WO | WO 2001/016138 A1 | 3/2001 |
| WO | WO 2001/019829 A2 | 3/2001 |
| WO | WO 2002/050071 A1 | 6/2002 |
| WO | WO 2002/072576 A1 | 9/2002 |
| WO | WO 2003/004497 A1 | 1/2003 |
| WO | WO 2004/017908 A2 | 3/2004 |
| WO | WO 2005/005429 A1 | 1/2005 |
| WO | WO 2005/011597 A2 | 2/2005 |
| WO | WO 2005/014599 A1 | 2/2005 |
| WO | WO 2005/047290 A2 | 5/2005 |
| WO | WO 2006/053121 A2 | 5/2006 |
| WO | WO 2006/065946 A1 | 6/2006 |
| WO | WO 2006/099075 A2 | 9/2006 |
| WO | WO 2007/026720 A1 | 3/2007 |
| WO | WO 2007/026950 A1 | 3/2007 |
| WO | WO 2007/027594 A1 | 3/2007 |
| WO | WO 2007/027729 A1 | 3/2007 |
| WO | WO 2007/087068 A2 | 8/2007 |
| WO | WO 2007/136790 A2 | 11/2007 |
| WO | WO 2008/033834 A1 | 3/2008 |
| WO | WO 2008/033854 A1 | 3/2008 |
| WO | WO 2008/033857 A2 | 3/2008 |
| WO | WO 2008/039218 A2 | 4/2008 |
| WO | WO 2008/054827 A2 | 5/2008 |
| WO | WO 2008/144253 A1 | 11/2008 |
| WO | WO 2009/039397 A2 | 3/2009 |
| WO | WO 2009/051822 A1 | 4/2009 |
| WO | WO 2009/077334 A1 | 6/2009 |
| WO | WO 2009/098144 A1 | 8/2009 |
| WO | WO 2009/158571 A1 | 12/2009 |
| WO | WO 2010/000633 A1 | 1/2010 |
| WO | WO 2010/006947 A1 | 1/2010 |
| WO | WO 2010/006970 A1 | 1/2010 |
| WO | WO 2010/028236 A1 | 3/2010 |
| WO | WO 2010/051549 A1 | 5/2010 |
| WO | WO 2010/065898 A2 | 6/2010 |
| WO | WO 2010/068788 A1 | 6/2010 |
| WO | WO 2010/068806 A1 | 6/2010 |
| WO | WO 2010/068810 A2 | 6/2010 |
| WO | WO 2010/122038 A1 | 10/2010 |
| WO | WO 2011/006074 A1 | 1/2011 |
| WO | WO 2011/140488 A1 | 11/2011 |
| WO | WO 2011/153514 A2 | 12/2011 |
| WO | WO 2012/020008 A1 | 2/2012 |
| WO | WO 2012/135801 A1 | 10/2012 |
| WO | WO 2012/143522 A1 | 10/2012 |
| WO | WO 2012/156334 A1 | 11/2012 |
| WO | WO 2012/158795 A1 | 11/2012 |
| WO | WO 2014/173289 A1 | 10/2014 |
| WO | WO 2015/035606 | 3/2015 |
| WO | WO 2015/061752 A1 | 4/2015 |
| WO | WO-2016008411 A1 | 1/2016 |
| WO | WO 2016/025720 | 2/2016 |
| WO | WO-2016024228 A1 | 2/2016 |
| WO | WO 2016/087994 A1 | 6/2016 |
| WO | WO 2016/100914 A1 | 6/2016 |
| WO | WO 2016/105582 A1 | 6/2016 |
| WO | WO 2017/046746 A1 | 3/2017 |
| WO | WO 2017/059224 A2 | 4/2017 |
| WO | WO 2018/033135 | 2/2018 |
| WO | WO 2018/033853 | 2/2018 |
| WO | WO 2018/137681 | 8/2018 |
| WO | WO 2018/193105 A1 | 10/2018 |
| WO | WO 2019/034009 | 2/2019 |
| WO | WO 2019/108795 | 6/2019 |

OTHER PUBLICATIONS

Extended European Search Report for European Application No. 14787642.9, dated Jan. 26, 2016, 5 pages.
International Search Report and Written Opinion for International Application No. PCT/CN2014/075943, dated Jul. 18, 2014, 10 pages.
Extended European Search Report for European Application No. 17841172.4, dated Mar. 5, 2020, 6 pages.
International Search Report and Written Opinion for International Application No. PCT/IB2017/054955, dated Sep. 10, 2018, 16 pages.
Extended European Search Report for European Application No. 17841107.0, dated Feb. 21, 2020, 12 pages.
International Search Report and Written Opinion for International Application No. PCT/CN2017/098023, dated Nov. 16, 2017, 10 pages.
International Search Report and Written Opinion for International Application No. PCT/CN2018/074108, dated Apr. 23, 2018, 12 pages.
International Search Report and Written Opinion for International Application No. PCT/CN2018/100145, dated Nov. 14, 2018, 8 pages.
International Search Report and Written Opinion for International Application No. PCT/US2018/063068, dated Feb. 27, 2019, 8 pages.
Bradshaw, J. M., "The Src, Syk, and Tec family kinases: Distinct types of molecular switches," Cell. Signalling, 22:1175-1184 (2010).
Caira, E. D. et al., "Crystalline polymorphism of organic compounds," Topics in Current Chemistry, vol. 198, 1998, pp. 163-208.
Conley, M. E. et al., "Primary B Cell Immunodeficiencies: Comparisons and Contrasts," Annu. Rev. Immunol., 27:199-227 (2009).
Davis, R. E. et al., "Chronic active B-cell-receptor signalling in diffuse large B-cell lymphoma," Nature, 463:88-92 (2010).
Gurcan, H. M. et al., "A review of the current use of rituximab in autoimmune diseases," Int. Immunopharmacol., 9:10-25 (2009).
Hackam, D. G. et al., "Translation of research evidence from animals to humans," JAMA, 296(14):1731-1732 (2006).
Humphries, L. A. et al., "Tec Kinases Mediate Sustained Calcium Influx via Site-specific Tyrosine Phosphorylation of the Phospholipase Cγ Src Homology 2-Src Homology 3 Linker," J. Biol.Chem. 279(36):37651-37661 (2004).
Jenkins, S. M. et al., "Substituent variation in azabicyclic triazole- and tetrazole-based muscarinic receptor ligands," J. Med. Chem., 35(13):2392-2406 (1992).
Jordan, V. C., "Tamoxifen: A most unlikely pioneering medicine," Nature Reviews: Drug Discovery, 2:205-213 (2003).
Khan, W. N., "Regulation of B lymphocyte development and activation by Bruton's tyrosine kinase," Immunol. Res., 23(2/3):147-156 (2001).
Kim, K.-H. et al., "Imidazo[1,5-a]quinoxalines as irreversible BTK inhibitors for the treatment of rheumatoid arthritis," Bioorg. Med. Chem. Lett., 21:6258-6263 (2011).
Lou, Y. et al., "Bruton's tyrosine kinase inhibitors: Approaches to potent and selective inhibition, preclinical and clinical evaluation for inflammatory diseases and B cell malignancies," J. Med. Chem., 55(10):4539-4550 (2012).

(56) References Cited

OTHER PUBLICATIONS

Mohamed, A. J. et al., "Bruton's tyrosine kinase (Btk): function, regulation, and transformation with special emphasis on the PH domain," Immunol. Rev., 228:58-73 (2009).

Pan, Z, "Bruton's tyrosine kinase as a drug discovery target," Drug News Perspect, 21(7):357-362 (2008).

Rokosz, L. L. et al., "Kinase inhibitors as drugs for chronic inflammatory and immunological diseases: progress and challenges," Expert Opin. Ther. Targets, 12(7):883-903 (2008).

Smith, C. I. E. et al., "Expression of Bruton's Agammaglobulinemia Tyrosine Kinase Gene, BTK, Is Selectively Down-Regulated in T Lymphocytes and Plasma Cells," J. Immunol., 152:557-565 (1994).

Takayama, T. et al., "Ring-fused pyrazole derivatives as potent inhibitors of lymphocyte-specific kinase (Lck): Structure, synthesis, and SAR," Bioorganic & Medicinal Chemistry Letters, 20(1):112-116 (Jan. 2010).

Takayama, T. et al., "Effects of the novel and potent lymphocyte-specific protein tyrosine kinase inhibitor TKM0150 on mixed lymphocyte reaction and contact hypersensitivity in mice," Arzneimittelforschung, 60(5):282-285 (2010).

Uckun, F. M. et al., "Bruton's tyrosine kinase as a new therapeutic target," Anti-Cancer Agents in Medicinal Chemistry, 7(6):624-632 (2007).

Vetrie, D. et al., "The gene involved in X-linked agammaglobulinaemia is a member of the sre family of protein-tyrosine kinases," Nature, 361:226-233 (1993).

Wilson, W. H. et al., "686—The Bruton's Tyrosine Kinase (Btk) Inhibitor, Ibrutinib (PCI-32765), Has Preferential Activity in the ABC Subtype of Relapsed/Refractory De Novo Diffuse Large B-Cell Lymphoma (DLBCL): Interim Results of a Multicenter, Open-Label, Phase2 Study," Poster #686, 54th American Society of Hematology (ASH) annual meeting abstract (Dec. 10, 2012).

Cartigny, D. et al., "General Asymmetric Hydrogenation of 2-Alkyl- and 2-Aryl-Substituted Quinoxaline Derivatives Catalyzed by Iridium-Difluorphos: Unusual Halide Effect and Synthetic Application," J. Org. Chem., Apr. 2012, vol. 77, No. 10, pp. 4544-4556.

Hirayama, Y., "Handbook for organic compound crystal—Principle and know-how," 2008, 28 pages.

Jie, L., "Deuterated Drugs Progress," Chemical Engineering Design Communication Medicine and Chemical Industry, 2016, vol. 42 (4), pp. 199.

Li, N. et al., "BGB-3111 is a novel and highly selective Bruton's tyrosine kinase (BTK) inhibitor," Cancer Center, vol. 75, No. 15, Supp. 1, Abstract No. 2597, 106th Annual Meeting of the American Association for Cancer Research, AACR 2015, Philadelphia, PA, United States, Aug. 2015, 2 pages.

MedChemExpress, "Zanubrutinib," Product Data Sheet, Retrieved from the Internet: www.medchemexpress.com, Retrieved Aug. 17, 2021, 2 pages.

Shioji, Y., "Production Technology of Solid Preparations," Tokyo, CMC Publication, Jan. 27, 2003, Popular Edition, pp. 9 and 12-13.

Takada, N., "Bulk Drug Form Screening and Selection at Drug Discovery Phase," Pharm Stage, Jan. 15, 2007 vol. 6, No. 10, pp. 20-25.

Office Action for Japanese Application No. 2019-508889, dated Jun. 22, 2021, 7 pages.

BTK INHIBITORS WITH IMPROVED DUAL SELECTIVITY

CROSS-REFERENCE TO RELATED APPLICATIONS

This application is a U.S. National Stage Application under 35 U.S.C. § 371 of International Application No. PCT/CN2018/100145, filed Aug. 12, 2018, which claims priority to, and the benefit of International Patent Application No. PCT/CN2017/097291, filed Aug. 12, 2017, the disclosures of which are hereby incorporated by reference in their entireties for all purposes.

FILED OF THE INVENTION

Disclosed herein is a tri-substituted phenyl Btk inhibitors with improved dual selectivity, a method and a composition for inhibiting Btk and treating disease associated with undesirable Btk activity (Btk-related diseases).

BACKGROUND OF THE INVENTION

Bruton's tyrosine kinase (Btk) belongs to the Tec family of cytoplasmic tyrosine kinases, which is the second largest family of non-receptor kinases in humans (Vetrie et al., Nature 361: 226-233, 1993; Bradshaw, Cell Signal. 22: 1175-84, 2010). It is expressed in all cell lineages of the hematopoietic system, except for T cells and is localized in bone marrow, spleen and lymph node tissue (Smith et al., J. Immunol. 152: 557-565, 1994). Inactivating mutations in the gene encoding Btk cause X-linked agammaglobulinemia (XLA) in humans and X-linked immunodeficiency (XID) in mice (Conley et al., Annu. Rev. Immunol. 27: 199-227, 2009). Both diseases are characterized by dramatic defects in B cell development and function, suggesting the essential role of Btk for B cell development and function. In addition, constitutive activation of Btk in B cells results in the accumulation of autoreactive plasma cells (Kersseboom et al., Eur J Immunol. 40:2643-2654, 2010). Btk is activated by upstream Src-family kinases in BCR signaling pathway. Once activated, Btk in turn phosphorylates phospholipase-Cγ (PLCγ), leading to $Ca^{2+}$ mobilization and activation of NF-κB and MAP kinase pathways. These proximal signaling events promote expression of genes involved in proliferation and survival (Humphries et al., J. Biol. Chem. 279: 37651, 2004). In addition to its essential regulatory role as downstream of BCR, Btk activity also plays a critical role in FcR signaling. Signaling via FcRγ associated receptors also promotes Btk-dependent proinflammatory cytokine production by cells such as macrophages (Di Paolo et al., Nat. Chem. Biol. 7: 41-50, 2011). Btk has been an important target due to its proximal location in the BCR and FcR signaling pathways. Preclinical studies show that Btk deficient mice are resistant to developing collagen-induced arthritis. Moreover, clinical studies of Rituxan, a CD20 antibody to deplete mature B-cells, reveal the key role of B-cells in a number of inflammatory diseases such as rheumatoid arthritis, systemic lupus erythematosus and multiple sclerosis (Gurcan et al., Int. Immunopharmacol. 9: 10-25, 2009). In addition, aberrant activating of Btk plays important role in pathogenesis of B-cell lymphomas indicating that inhibition of Btk is useful in the treatment of hematological malignancies (Davis et al., Nature 463: 88-92, 2010).

The covalent Btk inhibitor, i.e., ibrutinib (Imbruvica®) was approved by the US Food and Drug Administration for the treatment of chronic lymphocytic leukemia (CLL), mantle cell lymphoma (MCL), Waldenström's macroglobulinemia (WM) and chronic graft versus host disease (cGVHD). Even though excellent efficacy and general tolerability, there are adverse events like bleeding, rash and diarrhea reported, which are not typically observed in Btk deficient patients. From early phase of clinical trials testing Ibrutinib as monotherapy in MCL, CLL and small lymphocytic lymphoma (SLL), rash occurred at a frequency of 20-25% and diarrhea occurred at a frequency of 50-60% (Varinder et al., Ann Hematol 96(7): 1175-1184, 2017). These common toxicities are self-limiting grade 1 or 2 adverse events, and dose interruption or reduction is typically not required. Bleeding episodes were observed in 44% of patients in the CLL registration trial (Byrd J C, et al., N Engl J Med 369: 32-42, 2013) and in up to 61% of patients after a longer observation period (Byrd J C, et al., Blood 125: 2497-2506, 2015 and Wang M L, N Engl J Med 369: 507-516, 2013). Patients taking ibrutinib have experienced fatal bleeding events. Grade ≥3 bleeding, including subdural hematoma, gastrointestinal bleeding, hematuria, and post-procedural hemorrhage, which have been reported in up to 6% of patients taking ibrutinib (Lisa A. Raedler, Am Health Drug Benefits. 9: 89-92, 2016). Bleeding as a common adverse event (AE) has also been found in other Btk inhibitors such as ONO-4059, ACP-196, and BGB-3111 (Jun Chen, et al., EHA Learning Center, meeting abstract 2016).

These Ibrutinib related adverse effects were thought to be mostly associated with the off-target effects of ibrutinib that demonstrated to inhibit EGFR and Tec. Targeting EGFR is well known to induce dramatic cutaneous toxicity and gastrointestinal adverse effects because EGFR-signaling cascade is involved in biology of the skin and gastrointestinal system (Li, et al., Target Oncol 4(2):107-19, 2009 and Melosky, et al., Curr Oncol 19 (Suppl 1): S59-63, 2012). Both of Btk and Tec are belong to the Tec family kinases. Platelets express Btk and Tec, which serve as downstream of Glycoprotein VI (GPVI) signaling. Tec compensates for the absence of Btk in signaling downstream of GPVI in murine platelets (Atkinson B T, Blood 102: 3592-3599, 2003). Ibrutinib inhibition of Tec kinase interferes with platelet aggregation and may contribute to the observed bleeding (John C. Byrd, et al., N Engl J Med 374:323-332, 2016).

International application WO2014173289A disclosed a series of fused heterocyclic compounds, which were proved to be potent Btk inhibitors with high or comparable affinity to the target kinase. In WO2014173289, Compound 167 was proved to the most selective compound against Btk over Tec. The IC50 activity data of Compound 167 against Btk and Tec are reported in Table II of the present specification (i.e., 167 # in Table II). However, Compound 167 was also proved to have high affinity to EGFR, which is likely to give rise to adverse effects such as dramatic cutaneous toxicity and gastrointestinal adverse effects. This compound also showed low cellular potency, oral bioavailability and pharmacodynamic activity, which are not acceptable drug like properties.

Therefore, there is a need to develop a new Btk inhibitor which exhibits potent inhibitory activity against Btk and, at the same time, improves the selectivity of Btk over both Tec and EGFR (i.e., good dual selectivity corresponding to no less than 100 fold selectivity of Btk over Tec and of Btk over EGFR), which will reduce the clinical adverse effects significantly.

SUMMARY OF THE INVENTION

The inventors have unexpectedly found a new Btk inhibitor which exhibits potent inhibitory activity against Btk and, at the same time, exhibits improved or good dual selectivity of Btk over Tec and of Btk over EGFR. The good dual selectivity of Btk over Tec and of Btk over EGFR may be attributed to a combination of a tri-substituted phenyl ring and a piperidine ring (particularly N-substituted acryloyl piperidine ring) in the molecule. Such a combination may also improve cellular potency, oral bioavailability and pharmacodynamic activity.

In a first aspect, disclosed herein is a compound of formula (I):

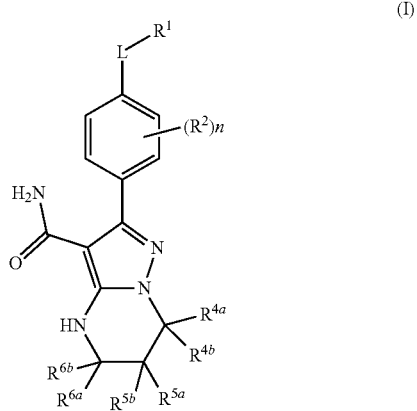

or a stereoisomer thereof, or a pharmaceutically acceptable salt thereof, wherein:

L is a bond, $CH_2$, $NR^{12}$, O, or S;

$R^1$ is halogen, heteroalkyl, alkyl, alkenyl, cycloalkyl, aryl, saturated or unsaturated heterocyclyl, heteroaryl, alkynyl, —CN, —$NR^{13}R^{14}$, —$OR^{13}$, —$COR^{13}$, —$CO_2R^{13}$, —$CONR^{13}R^{14}$, —$C(=NR^{13})NR^{14}R^{15}$, —$NR^{13}COR^{14}$, —$NR^{13}CONR^{14}R^{15}$, —$NR^{13}CO_2R^{14}$, —$SO_2R^{13}$, —$NR^{13}SO_2NR^{14}R^{15}$, or —$NR^{13}SO_2R^{14}$, wherein the alkyl, alkenyl, alkynyl, cycloalkyl, heteroaryl, aryl, and saturated or unsaturated heterocyclyl are optionally substituted with at least one substituent $R^{16}$;

n is an integer of 2, 3 or 4;

each $R^2$ is independently halogen, alkyl, —S-alkyl, —CN, —$NR^{13}R^{14}$, —$OR^{13}$, —$COR^{13}$, —$CO_2R^{13}$, —$CONR^{13}R^{14}$, —$C(=NR^{13})NR^{14}R^{15}$, —$NR^{13}COR^{14}$, —$NR^{13}CONR^{14}R^{15}$, —$NR^{13}CO_2R^{14}$, —$SO_2R^{13}$, —$NR^{13}SO_2NR^{14}R^{15}$, or —$NR^{13}SO_2R^{14}$;

$R^{4a}$ and $R^{4b}$ are each independently hydrogen, halogen, heteroalkyl, alkyl, alkenyl, cycloalkyl, saturated or unsaturated heterocyclyl, heteroaryl, alkynyl, —CN, —$NR^{13}R^{14}$, —$OR^{13}$, —$COR^{13}$, —$CO_2R^{13}$, —$CONR^{13}R^{14}$, —$C(=NR^{13})NR^{14}R^{15}$, —$NR^{13}COR^{14}$, —$NR^{13}CONR^{14}R^{15}$, —$NR^{13}CO_2R^{14}$, —$SO_2R^{13}$, —$NR^{13}SO_2NR^{14}R^{15}$, or —$NR^{13}SO_2R^{14}$, wherein the alkyl, alkenyl, alkynyl, cycloalkyl, heteroaryl, aryl, and saturated or unsaturated heterocyclyl are optionally substituted with at least one substituent $R^{16}$;

$R^{5a}$ and $R^{5b}$ are each independently hydrogen, halogen, heteroalkyl, alkyl, alkenyl, cycloalkyl, aryl, saturated or unsaturated heterocyclyl, heteroaryl, alkynyl, —CN, —$NR^{13}R^{14}$, —$OR^{13}$, —$COR^{13}$, —$CO_2R^{13}$, —$CONR^{13}R^{14}$, —$C(=NR^{13})NR^{14}R^{15}$, —$NR^{13}COR^{14}$, —$NR^{13}CONR^{14}R^{15}$, —$NR^{13}CO_2R^{14}$, —$SO_2R^{13}$, —$NR^{13}SO_2NR^{14}R^{15}$, or —$NR^{13}SO_2R^{14}$, wherein the alkyl, alkenyl, alkynyl, cycloalkyl, heteroaryl, aryl, and saturated or unsaturated heterocyclyl are optionally substituted with at least one substituent $R^{16}$;

$R^{6a}$ and $R^{6b}$ are each independently hydrogen, halogen, heteroalkyl, alkyl, alkenyl, cycloalkyl, aryl, saturated or unsaturated heterocyclyl, heteroaryl, alkynyl, —CN, —$NR^{13}R^{14}$, —$OR^{13}$, —$COR^{13}$, —$CO_2R^{13}$, —$CONR^{13}R^{14}$, —$C(=NR^{13})NR^{14}R^{15}$, —$NR^{13}COR^{14}$, —$NR^{13}CONR^{14}R^{15}$, —$NR^{13}CO_2R^{14}$, —$SO_2R^{13}$, —$NR^{13}SO_2NR^{14}R^{15}$, or —$NR^{13}SO_2R^{14}$, wherein the alkyl, alkenyl, alkynyl, cycloalkyl, heteroaryl, aryl, and saturated or unsaturated heterocyclyl are optionally substituted with at least one substituent $R^{16}$; or wherein ($R^{4a}$ and $R^{5a}$), or ($R^{4a}$ and $R^{5b}$), or ($R^{4b}$ and $R^{5a}$), or ($R^{4b}$ and $R^{5b}$), or ($R^{5a}$ and $R^{6a}$), or ($R^{5a}$ and $R^{6b}$), or ($R^{5b}$ and $R^{6a}$), or ($R^{5b}$ and $R^{6b}$), together with the atoms to which they are attached, may form a fused ring selected from cycloalkyl, saturated or unsaturated heterocycle, aryl, and heteroaryl rings, optionally substituted with at least one substituent $R^{16}$;

$R^{12}$ is H or alkyl;

$R^{13}$, $R^{14}$ and $R^{15}$ are each independently H, heteroalkyl, alkyl, alkenyl, alkynyl, cycloalkyl, saturated or unsaturated heterocyclyl, aryl, or heteroaryl; wherein ($R^{13}$ and $R^{14}$), and/or ($R^{14}$ and $R^{15}$) together with the atom(s) to which they are attached, each can form a ring selected from cycloalkyl, saturated or unsaturated heterocycle, aryl, and heteroaryl rings optionally substituted with at least one substituent $R^{16}$;

$R^{16}$ is halogen, substituted or unsubstitued alkyl, substituted or unsubstitued alkenyl, substituted or unsubstitued alkynyl, substituted or unsubstitued cycloalkyl, substituted or unsubstitued aryl, substituted or unsubstitued heteroaryl, substituted or unsubstitued heterocyclyl, oxo, —CN, —$OR^a$, —$NR^aR^b$, —$COR^a$, —$CO_2R^a$, —$CONR^aR^b$, —$C(=NR^a)NR^bR^c$, —$NR^aCOR^b$, —$NR^aCONR^aR^b$, —$NR^aCO_2R^b$, —$SO_2R^a$, —$SO_2$aryl, —$NR^aSO_2NR^bR^c$, or —$NR^aSO_2R^b$, wherein $R^a$, $R^b$, and $R^c$ are independently hydrogen, halogen, substituted or unsubstitued alkyl, substituted or unsubstitued alkenyl, substituted or unsubstitued alkynyl, substituted or unsubstitued cycloalkyl, substituted or unsubstitued aryl, substituted or unsubstitued heteroaryl, substituted or unsubstitued heterocyclyl, wherein ($R^a$ and $R^b$), and/or ($R^a$ and $R^b$) together with the atoms to which they are attached, can form a ring selected from cycloalkyl, saturated or unsaturated heterocycle, aryl, and heteroaryl rings.

In some embodiments of the first aspect, L is a bond.

In some embodiments of the first aspect, $R^1$ is halogen, alkyl, alkenyl, cycloalkyl, aryl, saturated heterocyclyl, heteroaryl, or —$OR^{13}$, wherein the alkyl, alkenyl, cycloalkyl, and heteroaryl are optionally substituted with at least one substituent $R^{16}$. In some preferred embodiment, $R^1$ is alkyl or cycloalkyl.

In some embodiments of the first aspect, n is 2.

In some embodiments of the first aspect, one of $R^2$ is at position 3 of the phenyl ring, and the other $R^2$ is at position 5 of the phenyl ring.

In some embodiments of the first aspect, n is 2; and one of $R^2$ is at position 3 of the phenyl ring, and the other $R^2$ is at position 5 of the phenyl ring. In some preferred embodiment, $R^2$ is optionally partially or fully deuterated, i.e., one or more carbon-bound hydrogen(s) in the definition of $R^2$ are replaced by one or more deuterium(s). In some more preferred embodiments, $R^2$, at each of its occurrence, is halogen, alkyl or —O-alkyl.

In some embodiments of the first aspect, $R^{4a}$, $R^{5a}$, $R^{5b}$, $R^{6a}$ and $R^{6b}$ are hydrogen; and $R^{4b}$ is alkyl, or saturated heterocyclyl, wherein the alkyl and saturated heterocyclyl are optionally substituted with at least one substituent $R^{16}$. In other embodiments, $R^{4a}$, $R^{5a}$, $R^{5b}$, $R^{6a}$ and $R^{6b}$ are hydrogen; and $R^{4b}$ is a saturated heterocyclyl containing a nitrogen atom which is optionally substituted with acryloyl or propiolyl. In further embodiments, the nitrogen atom of the saturated heterocyclyl in the definition of $R^{4b}$ is substituted with acryloyl. In even further embodiments, the saturated heterocyclyl in the definition of $R^{4b}$ is a monocyclic ring selected from a azetidine, pyrrole, piperidine, azapane and azocane ring; or a spiro or bridged bicyclic ring selected from azabicyclooctanyl, azaspirononanyl and azaspiroheptanyl.

In alternative embodiments of the first aspect, ($R^{4a}$ and $R^{5a}$), or ($R^{4a}$ and $R^{5b}$), or ($R^{4b}$ and $R^{5a}$), or ($R^{4b}$ and $R^{5b}$), or ($R^{5a}$ and $R^{6a}$), or ($R^{5a}$ and $R^{6b}$), or ($R^{5b}$ and $R^{6a}$), or ($R^{5b}$ and $R^{6b}$), together with the atoms to which they are attached, form a fused ring selected from cycloalkyl, saturated or unsaturated heterocycle, aryl, and heteroaryl rings, optionally substituted with at least one substituent $R^{16}$. In further embodiments, ($R^{4a}$ and $R^{5a}$), or ($R^{4a}$ and $R^{5b}$), or ($R^{4b}$ and $R^{5a}$), or ($R^{4b}$ and $R^{5b}$), or ($R^{5a}$ and $R^{6a}$), or ($R^{5a}$ and $R^{6b}$), or ($R^{5b}$ and $R^{6a}$), or ($R^{5b}$ and $R^{6b}$), together with the atoms to which they are attached, form a fused saturated heterocycle ring optionally substituted with at least one substituent $R^{16}$. In even further embodiments, the fused saturated heterocycle ring is a azetidine, pyrrole, piperidine, zapane or azocane ring optionally substituted with a substituent $R^{16}$ at the nitrogen atom of the fused ring, wherein the substituent $R^{16}$ is acryloyl or propiolyl.

In some embodiments of the first aspect, the compounds disclosed herein are deuterated compounds. Specifically, the compounds disclosed herein are partially or fully deuterated in the definition of $R^2$. More preferably, the definition of $R^2$ as alkyl or O-alkyl is partially or fully deuterated.

In a second aspect, disclosed herein is a compound of formula (II):

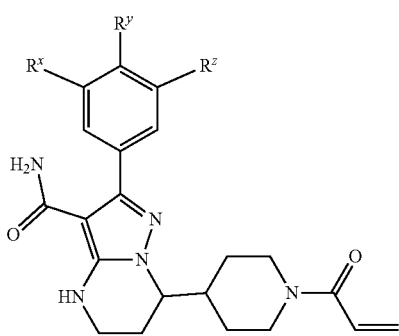

(II)

or a stereoisomer thereof, or a pharmaceutically acceptable salt thereof, wherein:

$R^x$ is halogen, alkyl, or —O-alkyl, wherein the alkyl group or moiety is optionally partially or fully deuterated;

$R^y$ is halogen, alkyl optionally substituted with at least substituents selected from hydroxy or halogen, or cycloalkyl; and $R^z$ is halogen, alkyl, or —O-alkyl, wherein the alkyl group or moiety is optionally partially or fully deuterated.

In some embodiments of the second aspect, disclosed herein is a compound of formula (IIa):

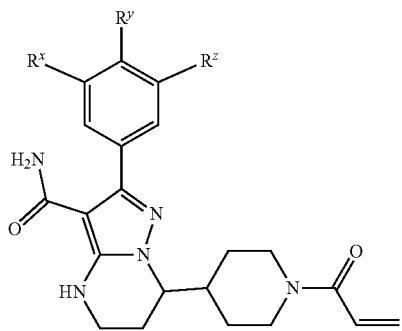

(IIa)

or a stereoisomer thereof, or a pharmaceutically acceptable salt thereof, wherein:

$R^x$ is methoxy, ethoxy, methyl, ethyl or chloro, wherein the methoxy, ethoxy, methyl, ethyl is optionally partially or fully deuterated;

$R^y$ is 2-hydroxylethyl, trifluoromethyl, isopropyl, cyclopropyl, methyl, chloro, bromo, or iodo; and $R^z$ is methoxy, methyl, or chloro, wherein the methoxy or methyl is optionally partially or fully deuterated.

In some embodiments of the second aspect, $R^x$ is methoxy, ethoxy, methyl, chloro, $CD_3$, —$CD_2CD_3$, $OCD_3$, or —O-$CD_2CD_3$; $R^y$ is 2-hydroxylethyl, $CF_3$, isopropyl, cyclopropyl, Methyl, chloro, bromo, or iodo; and $R^z$ is ethoxy, methoxy, methyl, ethyl, chloro, or $CD_3$, —$CD_2CD_3$, $OCD_3$, or —O-$CD_2CD_3$.

In some embodiments of the second aspect, $R^x$ is methoxy, ethoxy, methyl, ethyl, chloro, or $OCD_3$; $R^y$ is 2-hydroxylethyl, $CF_3$, isopropyl, cyclopropyl, methyl, chloro, bromo, or iodo; and $R^z$ is methoxy, methyl, chloro, or $OCD_3$.

In some embodiments of the second aspect, $R^x$ is methoxy or $OCD_3$, $R^y$ is cyclopropyl or methyl; and $R^z$ is methoxy or $OCD_3$.

In some embodiments of the above first and second aspects, disclosed herein is a compound or a stereoisomer thereof, or a pharmaceutically acceptable salt thereof, which is selected from: Example Nos. A1, A1a, A1b, A2, A2a, A2b, A3, A4, A5, A6, A6a, A6b, A7, A8, A9, A10, A11, A11a, A11b, A12, A13, A14, A15, A16, A17, A18, A19, A20, A21, A22, A23, A24, A25, A26, A27, A28, A29, A30, A31, A32, A33, A34, A35, A36, A37, A38, A39, A40, A41, A42, A43, A44, A45, A46, A47, A48, A49, A50, A51, A52, A52a, A52b, B1, B2, B3, C1, C2, D1, D2, E1, F1, G1, H1,

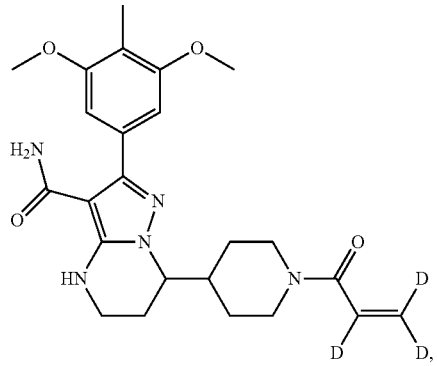

7
-continued
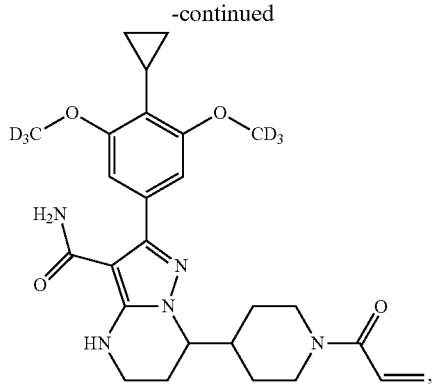
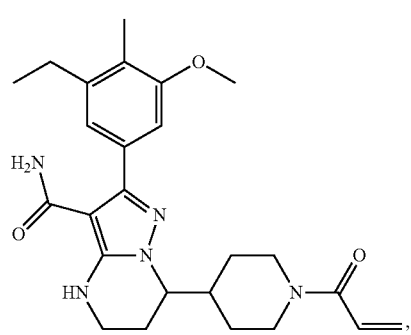
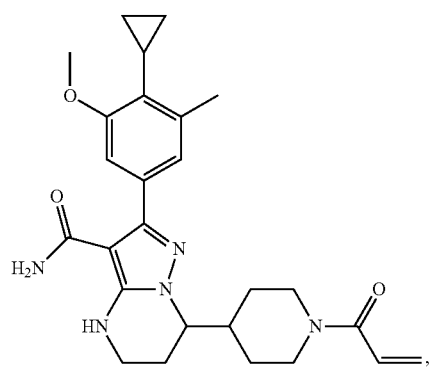
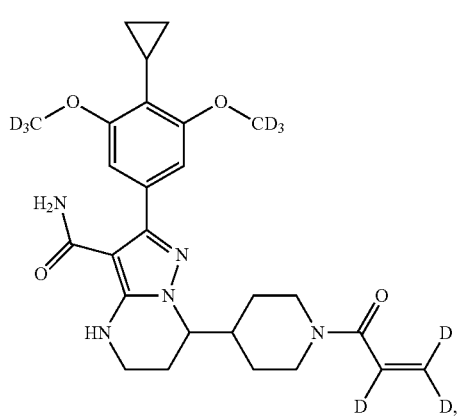
8
-continued
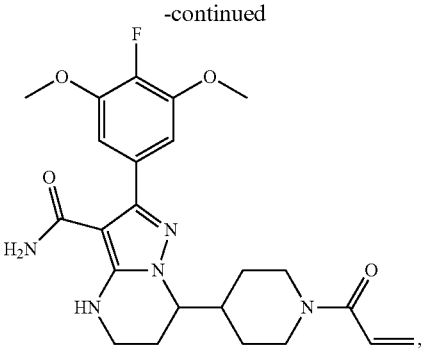
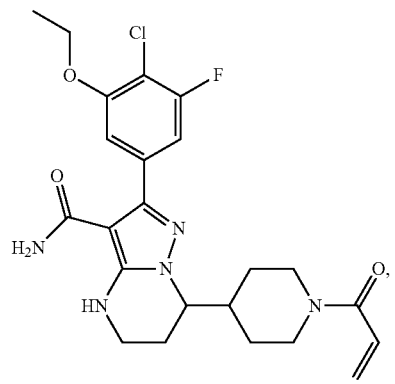
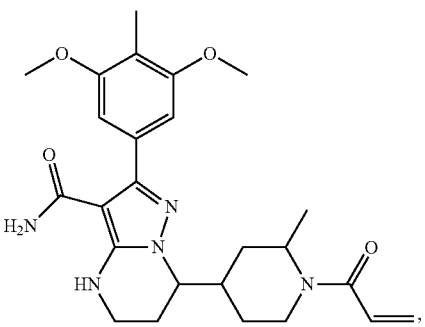

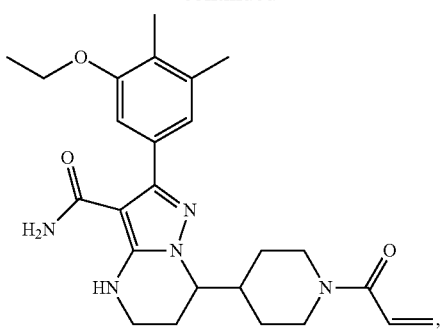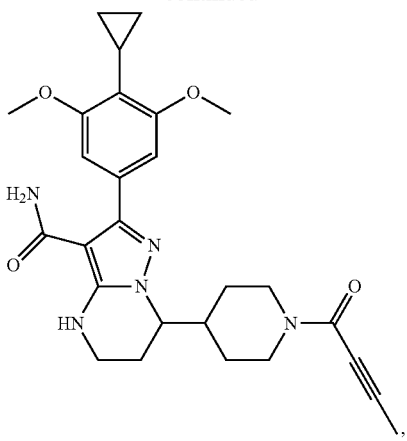

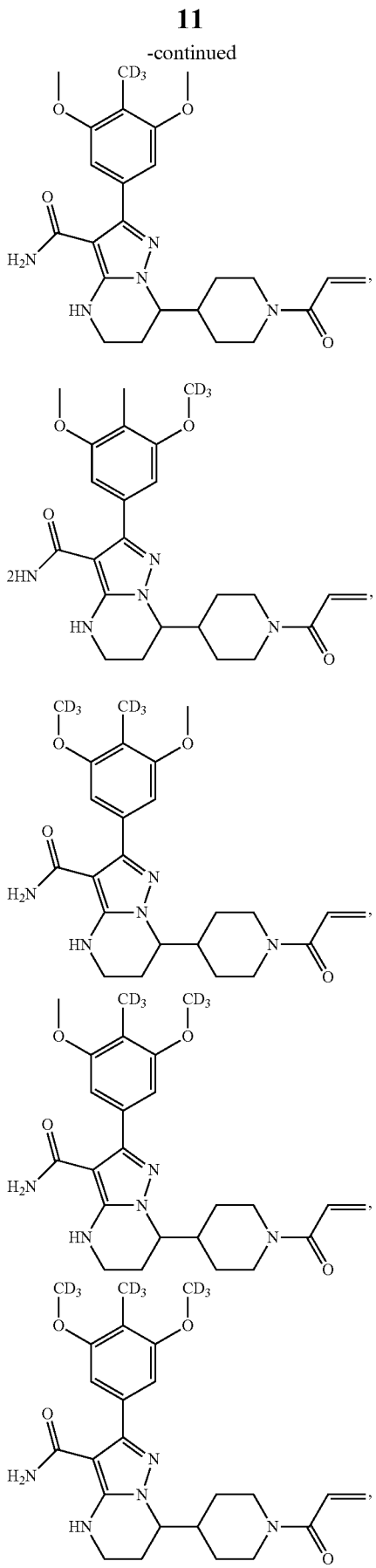

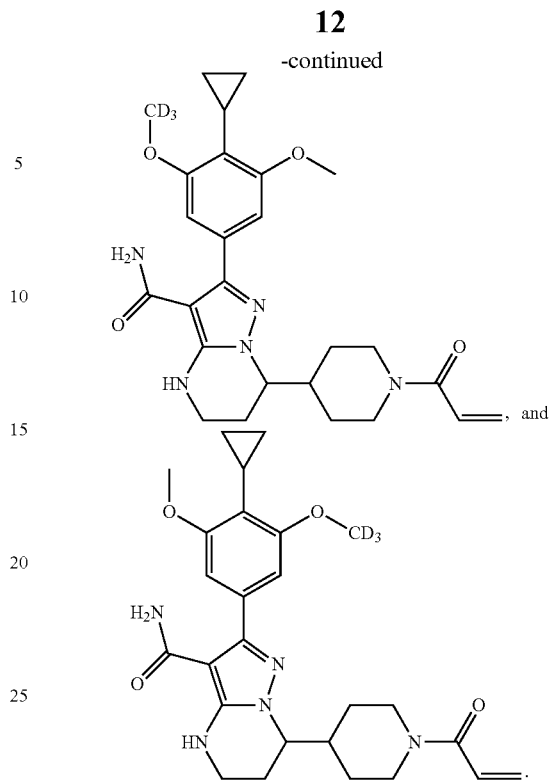

In other embodiments of the above first and second aspects, disclosed herein is a compound or a stereoisomer thereof, or a pharmaceutically acceptable salt thereof, which is selected from: A1a, A2a, A5, A6a, A8, A11, A11b, A18, A20, A22, A33, A34, A36, A46 and C1.

In a third aspect, disclosed herein is a method of treating a disease associated with undesirable Btk activity in a subject by administering to the subject the compound disclosed herein or a stereoisomer thereof, or a pharmaceutically acceptable salt thereof.

In a fourth aspect, disclosed herein is the compound disclosed herein or a stereoisomer thereof, or a pharmaceutically acceptable salt thereof for use in treating a disease associated with undesirable Btk activity.

In a fifth aspect, disclosed herein is a pharmaceutical composition comprising the therapeutically effective amount of a compound disclosed herein or a stereoisomer thereof, or a pharmaceutically acceptable salt thereof, and at least one pharmaceutically acceptable carrier.

BRIEF DESCRIPTIONS OF THE DRAWINGS

Figure 1B:
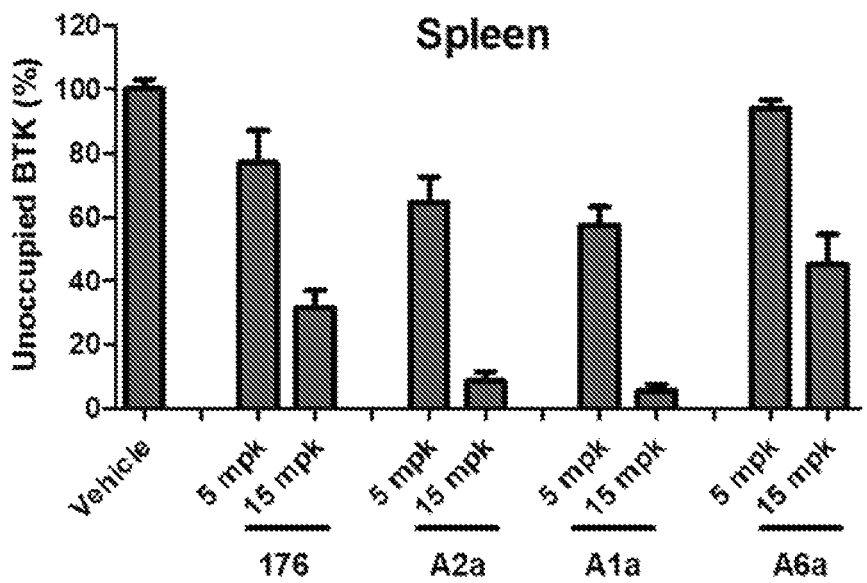
Figure 2A:
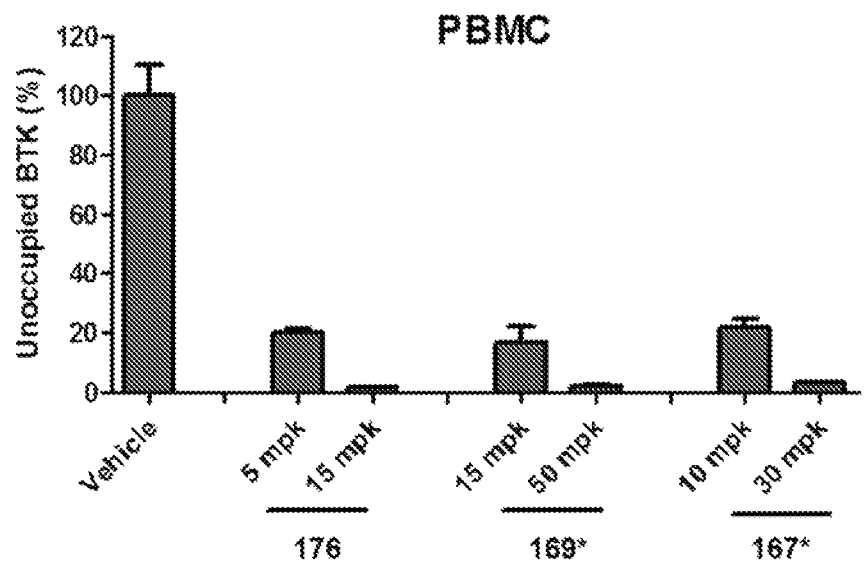
Figure 2B:
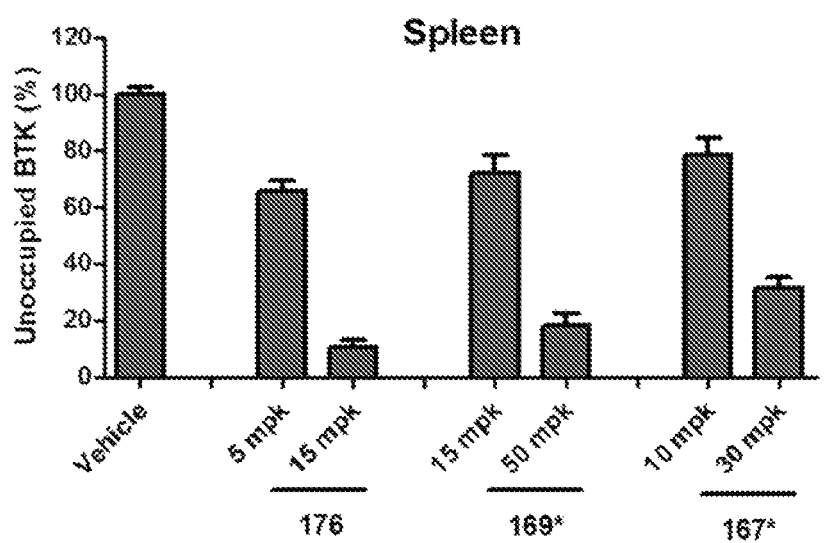
Figure 3:
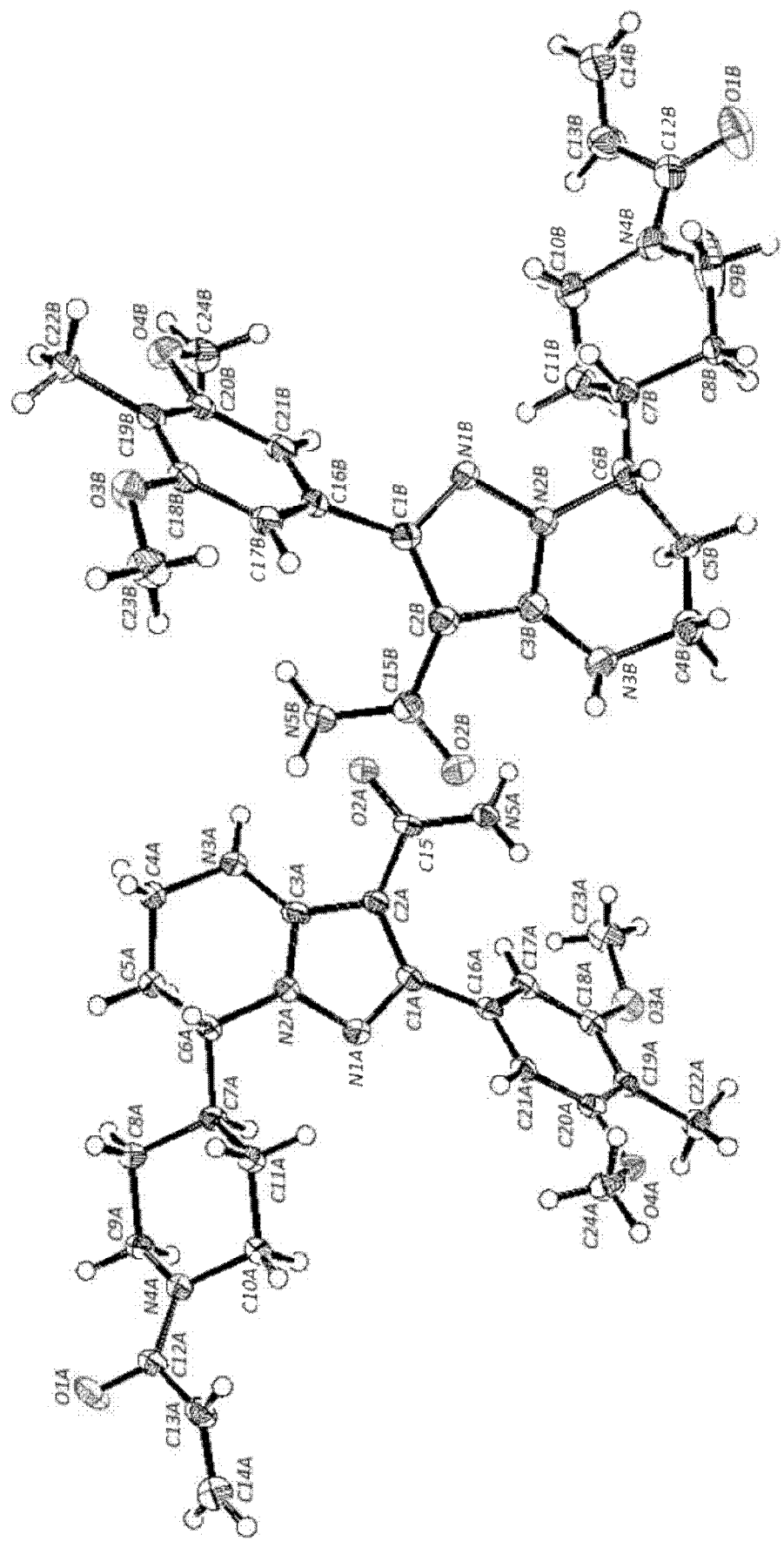

FIG. 1A shows in vivo PD result of Compounds A1a, A2a and A6a compared to Compound 176 in PBMC;
FIG. 1B shows in vivo PD result of Compounds A1a, A2a and A6a compared to compound 176 in Spleen;
FIG. 2A shows in vivo PD result of Compounds 169* and 167* compared to Compound 176 in PBMC; and
FIG. 2B shows in vivo PD result of Compounds 169* and 167* compared to Compound 176 in Spleen.
FIG. 3 shows the single crystal of compound A1a used to determine the (S)-configuration.

DETAILED DESCRIPTION OF THE INVENTION

Unless specifically defined elsewhere in this document, all other technical and scientific terms used herein have the meaning commonly understood by one of ordinary skill in the art to which this invention belongs.

As used herein, including the appended claims, the singular forms of words such as "a", "an", and "the", include their corresponding plural references unless the context clearly indicates otherwise.

The term "or" is used to mean, and is used interchangeably with, the term "and/or" unless the context clearly dictates otherwise.

The term "alkyl" refers to a hydrocarbon group selected from linear and branched saturated hydrocarbon groups of 1-18, or 1-12, 1-6 or 1-4 carbon atoms. Examples of the alkyl group include methyl, ethyl, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), and 1,1-dimethylethyl or t-butyl ("t-Bu"). Other examples of the alkyl group include 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl and 3,3-dimethyl-2-butyl groups. Lower alkyl means 1-8, preferably 1-6, more preferably 1-4 carbon atoms; lower alkenyl or alkynyl means 2-8, 2-6 or 2-4 carbon atoms. The alkyl group can be optionally partially or fully enriched in deuterium, e.g., $-CD_3$, $-CD_2CD_3$ and the like.

The term "—O-alkyl" refer to o an alkyl group, as previously defined, attached to the parent molecular moiety through an oxygen atom.

The term "alkenyl" refers to a hydrocarbon group selected from linear and branched hydrocarbon groups comprising at least one C=C double bond and of 2-18, or 2-12, or 2-6 carbon atoms. Examples of the alkenyl group may be selected from ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl, and hexa-1,3-dienyl groups. The alkenyl group can be optionally partially or fully enriched in deuterium.

The term "alkynyl" refers to a hydrocarbon group selected from linear and branched hydrocarbon group, comprising at least one C≡C triple bond and of 2-18, or 2-12, or 2-6 carbon atoms. Examples of the alkynyl group include ethynyl, 1-propynyl, 2-propynyl (propargyl), 1-butynyl, 2-butynyl, and 3-butynyl groups. The alkynyl group can be optionally partially or fully enriched in deuterium.

The term "cycloalkyl" refers to a hydrocarbon group selected from saturated and partially unsaturated cyclic hydrocarbon groups, comprising monocyclic and polycyclic (e.g., bicyclic and tricyclic) groups. For example, the cycloalkyl group may be of 3-12, or 3-8, or 3-6 carbon atoms. Even further for example, the cycloalkyl group may be a monocyclic group of 3-12, or 3-8, or 3-6 carbon atoms. Examples of the monocyclic cycloalkyl group include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, and cyclododecyl groups. Examples of the bicyclic cycloalkyl groups include those having 7-12 ring atoms arranged as a bicycle ring selected from [4,4], [4,5], [5,5], [5,6] and [6,6] ring systems, or as a bridged bicyclic ring selected from bicyclo[2.2.1]heptane, bicyclo[2.2.2]octane, and bicyclo[3.2.2]nonane. The ring may be saturated or have at least one double bond (i.e. partially unsaturated), but is not fully conjugated, and is not aromatic, as aromatic is defined herein. The cycloalkyl group can be optionally partially or fully enriched in deuterium.

The term "deuterated compound" refers to a compound wherein one or more carbon-bound hydrogen(s) are replaced by one or more deuterium(s). Similarly, the term "deuterated" is be used herein to modify a chemical structure or an organic group or radical, wherein one or more carbon-bound hydrogen(s) are replaced by one or more deuterium(s), e.g., "deuterated-alkyl", "deuterated-cycloalkyl", "deuterated-heterocycloalkyl", "deuterated-aryl", "deuterated-morpholinyl", and the like. For example, the term "deuterated-alkyl" defined above refers to an alkyl group as defined herein, wherein at least one hydrogen atom bound to carbon is replaced by a deuterium. In a deuterated alkyl group, at least one carbon atom is bound to a deuterium; and it is possible for a carbon atom to be bound to more than one deuterium; it is also possible that more than one carbon atom in the alkyl group is bound to a deuterium.

The term "aryl" herein refers to a group selected from: 5- and 6-membered carbocyclic aromatic rings, for example, phenyl; bicyclic ring systems such as 7-12 membered bicyclic ring systems wherein at least one ring is carbocyclic and aromatic, selected, for example, from naphthalene, and indane; and tricyclic ring systems such as 10-15 membered tricyclic ring systems wherein at least one ring is carbocyclic and aromatic, for example, fluorene. For example, the aryl group is selected from 5- and 6-membered carbocyclic aromatic rings fused to a 5- to 7-membered cycloalkyl or heterocyclic ring optionally comprising at least one heteroatom selected from N, O, and S, provided that the point of attachment is at the carbocyclic aromatic ring when the carbocyclic aromatic ring is fused with a heterocyclic ring, and the point of attachment can be at the carbocyclic aromatic ring or at the cycloalkyl group when the carbocyclic aromatic ring is fused with a cycloalkyl group. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap with heteroaryl, separately defined below. Hence, if one or more carbocyclic aromatic rings are fused with a heterocyclic aromatic ring, the resulting ring system is heteroaryl, not aryl, as defined herein.

The term "halogen" or "halo" refers to F, Cl, Br or I.

The term "heteroalkyl" refers to alkyl comprising at least one heteroatom.

The term "heteroaryl" refers to a group selected from: 5- to 7-membered aromatic, monocyclic rings comprising 1, 2, 3 or 4 heteroatoms selected from N, O, and S, with the remaining ring atoms being carbon; 8- to 12-membered bicyclic rings comprising 1, 2, 3 or 4 heteroatoms, selected from N, O, and S, with the remaining ring atoms being carbon and wherein at least one ring is aromatic and at least one heteroatom is present in the aromatic ring; and 11- to 14-membered tricyclic rings comprising 1, 2, 3 or 4 heteroatoms, selected from N, O, and S, with the remaining ring atoms being carbon and wherein at least one ring is aromatic and at least one heteroatom is present in an aromatic ring. For example, the heteroaryl group includes a 5- to 7-membered heterocyclic aromatic ring fused to a 5- to 7-membered cycloalkyl ring. For such fused, bicyclic heteroaryl ring systems wherein only one of the rings comprises at least one heteroatom, the point of attachment may be at the heteroaromatic ring or at the cycloalkyl ring. When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1. Examples of the heteroaryl group include, but are not limited to, (as numbered from the linkage position assigned priority 1) pyridyl (such as 2-pyridyl, 3-pyridyl, or 4-pyridyl), cinnolinyl, pyrazinyl, 2,4-pyrimidinyl, 3,5-pyrimidinyl, 2,4-imidazolyl, imidazopyridinyl, isoxazolyl, oxazolyl, thiazolyl, isothiazolyl, thiadiazolyl, tetrazolyl, thienyl, triazinyl, benzothienyl, furyl, benzofuryl, benzoimidazolyl, indolyl, isoindolyl, indolinyl, phthalazinyl, pyrazinyl, pyridazinyl, pyrrolyl, triazolyl, quinolinyl, isoquinolinyl, pyrazolyl, pyrrolopyridinyl (such as 1H-pyrrolo[2,3-b]pyridin-5-yl), pyrazolopyridinyl (such as 1H-pyrazolo[3,4-b]pyridin-5-yl), benzoxazolyl (such as benzo[d]oxazol-6-yl), pteridinyl, purinyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, furazanyl, benzofurazanyl, benzothiophenyl, benzothiazolyl, benzoxazolyl, quinazolinyl, quinoxalinyl, naphthyridinyl, furopyridinyl, benzothiazolyl (such as benzo[d]thiazol-6-yl), indazolyl (such as 1H-indazol-5-yl) and 5,6,7,8-tetrahydroisoquinoline.

The term "heterocyclic" or "heterocycle" or "heterocyclyl" refers to a ring selected from 4- to 12-membered monocyclic, bicyclic and tricyclic, saturated and partially unsaturated rings comprising at least one carbon atoms in addition to 1, 2, 3 or 4 heteroatoms, selected from oxygen, sulfur, and nitrogen. "Heterocycle" also refers to a 5- to 8-membered heterocyclic ring comprising at least one heteroatom selected from N, O, and S fused with 5-, 6-, 7-, and/or 8-membered cycloalkyl, carbocyclic aromatic or heteroaromatic ring, provided that the point of attachment is at the heterocyclic ring when the heterocyclic ring is fused with a carbocyclic aromatic or a heteroaromatic ring, and that the point of attachment can be at the cycloalkyl or heterocyclic ring when the heterocyclic ring is fused with cycloalkyl.

The "heterocycle" also refers to an aliphatic spirocyclic ring comprising at least one heteroatom selected from N, O, and S, provided that the point of attachment is at the heterocyclic ring. The rings may be saturated or have at least one double bond (i.e. partially unsaturated). The heterocycle may be substituted with oxo. The point of the attachment may be carbon or heteroatom in the heterocyclic ring. A heterocycle is not a heteroaryl as defined herein. Examples of the heterocycle include, but not limited to, (as numbered from the linkage position assigned priority 1) 1-pyrrolidinyl, 2-pyrrolidinyl, 2,4-imidazolidinyl, 2,3-pyrazolidinyl, 1-piperidinyl, 2-piperidinyl, 3-piperidinyl, 4-piperidinyl, 2,5-piperazinyl, pyranyl, 2-morpholinyl, 3-mo holinyl, oxiranyl, aziridinyl, thiiranyl, azetidinyl, oxetanyl, thietanyl, 1,2-dithietanyl, 1,3-difhietanyl, dihydropyridinyl, tetrahydropyridinyl, thiomorpholinyl, thioxanyl, piperazinyl, homopiperazinyl, homopiperidinyl, azepanyl, oxepanyl, thiepanyl, 1,4-oxathianyl, 1,4-dioxepanyl, 1,4-oxafhiepanyl, 1,4-oxaazepanyl, 1,4-difhiepanyl, 1,4-fhiazepanyl and 1,4-diazepane 1,4-dithianyl, 1,4-azathianyl, oxazepinyl, diazepinyl, thiazepinyl, dihydrofhienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, 1,4-dioxanyl, 1,3-dioxolanyl, pyrazolinyl, pyrazolidinyl, dithianyl, difhiolanyl, pyrazolidinylimidazolinyl, pyrimidinonyl, 1,1-dioxo-thiomo holinyl, 3-azabicyco[3.1.0]hexanyl, 3-azabicyclo[4.1.0]heptanyl and azabicyclo[2.2.2]hexanyl. Substituted heterocycle also includes ring systems substituted with one or more oxo moieties, such as piperidinyl N-oxide, morpholinyl-N-oxide, 1-oxo-1-thiomorpholinyl and 1,1-dioxo-1-thiomorpholinyl.

The term "fused ring" herein refers to a polycyclic ring system, e.g., a bicyclic or tricyclic ring system, in which two rings share only two ring atoms and one bond in common. Examples of fused rings may comprise a fused bicyclic cycloalkyl ring such as those having from 7 to 12 ring atoms arranged as a bicyclic ring selected from [4,4], [4,5], [5,5], [5,6] and [6,6] ring systems as mentioned above; a fused bicyclic aryl ring such as 7 to 12 membered bicyclic aryl ring systems as mentioned above, a fused tricyclic aryl ring such as 10 to 15 membered tricyclic aryl ring systems mentioned above; a fused bicyclic heteroaryl ring such as 8- to 12-membered bicyclic heteroaryl rings as mentioned above, a fused tricyclic heteroaryl ring such as 11- to 14-membered tricyclic heteroaryl rings as mentioned above; and a fused bicyclic or tricyclic heterocyclyl ring as mentioned above.

When compounds contain olefin double bonds, unless specified otherwise, such double bonds are meant to include both E and Z geometric isomers.

Some of the compounds may exist with different points of attachment of hydrogen, referred to as tautomers. For example, compounds including carbonyl —CFbC(O)— groups (keto forms) may undergo tautomerism to form hydroxyl —CH═C(OH)— groups (enol forms). Both keto and enol forms, individually as well as mixtures thereof, are also intended to be included where applicable.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. In addition, if a compound is obtained as an acid addition salt, the free base can be obtained by basifying a solution of the acid salt. Conversely, if the product is a free base, an addition salt, such as a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable addition salts.

The terms "administration", "administering", "treating" and "treatment" herein, when applied to an animal, human, experimental subject, cell, tissue, organ, or biological fluid, mean contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. The term "administration" and "treatment" also means in vitro and ex vivo treatments, e.g., of a cell, by a reagent, diagnostic, binding compound, or by another cell. The term "subject" herein includes any organism, preferably an animal, more preferably a mammal (e.g., rat, mouse, dog, cat, rabbit) and most preferably a human.

An "effective amount" refers to an amount of at least one compound and/or at least one stereoisomer thereof, and/or at least one pharmaceutically acceptable salt thereof effective to "treat" a disease or disorder in a subject, and that will elicit, to some significant extent, the biological or medical response of a tissue, system, animal or human that is being sought, such as when administered, is sufficient to prevent development of, or alleviate to some extent, one or more of the symptoms of the condition or disorder being treated. The therapeutically effective amount will vary depending on the compound, the disease and its severity and the age, weight, etc., of the mammal to be treated.

The term "at least one substituent" includes, for example, from 1 to 4, such as from 1 to 3, further as 1 or 2, substituents, depending on the available valence. For example, "at least one substituent $R^{16}$" herein includes from 1 to 4, such as from 1 to 3, further as 1 or 2, substituents selected from the list of $R^{16}$ as disclosed herein.

The compound disclosed herein or a stereoisomer thereof, or a pharmaceutically acceptable salt thereof can be used to treat a disease selected from an allergic disease, an autoimmune disease, an inflammatory disease, a cancer, or a combination of two or more thereof. The compound disclosed herein or a stereoisomer thereof, or a pharmaceutically acceptable salt thereof can also be used to treat a B-cell proliferative disease. Specifically, the B-cell proliferative disease is B-cell malignancies, selected from lymphoma, non-Hodgkin's lymphoma (NHL), diffuse large B cell lymphoma (DLBCL), mantle cell lymphoma (MCL), follicular lymphoma (FL), chronic lymphocytic leukemia (CLL), small lymphocytic lymphoma (SLL), waldenstrom macroglobulinemia (WM), marginal zone lymphoma (MZL), Hairy cell leukemia (HCL), Burkitt's-like lymphoma (BL), or a combination of two or more thereof.

EXAMPLES

The examples below are intended to be purely exemplary and should not be considered to be limiting in any way. Efforts have been made to ensure accuracy with respect to numbers used (for example, amounts, temperature, etc.), but some experimental errors and deviations should be accounted for. Unless indicated otherwise, temperature is in degrees Centigrade. Reagents were purchased from commercial suppliers such as Sigma-Aldrich, Alfa Aesar, or TCI, and were used without further purification unless indicated otherwise.

Unless indicated otherwise, the reactions set forth below were performed under a positive pressure of nitrogen or argon or with a drying tube in anhydrous solvents; the reaction flasks were fitted with rubber septa for the introduction of substrates and reagents via syringe; and glassware was oven dried and/or heat dried.

$^1$H NMR spectra were recorded on a Agilent instrument operating at 400 MHz. $^1$HNMR spectra were obtained using CDCl$_3$, CD$_2$Cl$_2$, CD$_3$OD, D$_2$O, d$_6$-DMSO, d$_6$-acetone or (CD$_3$)$_2$CO as solvent and tetramethylsilane (0.00 ppm) or residual solvent (CDCl$_3$: 7.25 ppm; CD$_3$OD: 3.31 ppm; D$_2$O: 4.79 ppm; d$_6$-DMSO: 2.50 ppm; d$_6$-acetone: 2.05; (CD$_3$)$_2$CO: 2.05) as the reference standard. When peak multiplicities are reported, the following abbreviations are used: s (singlet), d (doublet), t (triplet), q (quartet), qn (quintuplet), sx (sextuplet), m (multiplet), br (broadened), dd (doublet of doublets), dt (doublet of triplets). Coupling constants, when given, are reported in Hertz (Hz).

LC-MS spectrometer (Agilent 1260) Detector: MWD (190-400 nm), Mass detector: 6120 SQ Mobile phase: A: acetonitrile with 0.1% Formic acid, B: water with 0.1% Formic acid Column: Poroshell 120 EC-C18, 4.6×50 mm, 2.7 μm Gradient method: Flow: 1.8 mL/min

| Time (min) | A (%) | B (%) |
|---|---|---|
| 0.00 | 5 | 95 |
| 1.5 | 95 | 5 |
| 2.0 | 95 | 5 |
| 2.1 | 5 | 95 |
| 3.0 | 5 | 95 |

Preparative HPLC was conducted on a column (150×21.2 mm ID, 5 μm, Gemini NX-C18) at a flow rate of 20 mL/min, injection volume 2 ml, at room temperature and UV Detection at 214 nm and 254 nm.

In the following examples, the abbreviations below are used:

AcOH or HOAc Acetic acid aq. aqueous

Brine Saturated aqueous sodium chloride solution

DCM Dichloromethane

C$_2$H$_5$I Iodoethane

DMF N,N-Dimethylformamide

DMAC Dimethyl acetamide

DMSO Dimethyl sulfoxide

EA Ethyl acetate

EDCI 1-Ethyl-3-(3-dimethylaminopropyl)carbodiimide hydrochloride

EtOH ethyl alcohol h hour

H$_2$O$_2$ Hydrogen peroxide

HOBt Hydroxybenzotriazole

MeOH Methanol

MsOH Methanesulfonic acid n-BuLi n-Butyllithium

NCS N-Chlorosuccinimide

NH$_4$Cl Ammonium chloride

Pd/C Palladium on carbon powder

Pd(dppf)Cl$_2$ [1,1'-Bis(diphenylphosphino)ferrocene]dichloropalladium(II)

Pd(OAc)$_2$ Palladium acetate

Pd(OH)$_2$/C Palladium hydroxide on carbon powder

PE Petroleum ether pH -lg(hydrogen ion concentration)

Pre-TLC Prepared thin layer chromatography

RT room temperature sat. Saturated t-Bu$_3$P Tritert-butylphosphane

THF Tetrahydrofuran

TEA Triethylamine

TFA Trifluoroacetic acid

Examples of A Series

Example A1: 7-(1-acryloylpiperidin-4-yl)-2-(3,5-dimethoxy-4-methylphenyl)-4,5,6,7-tetrahydropyrazolo[1,5-a]pyrimidine-3-carboxamide

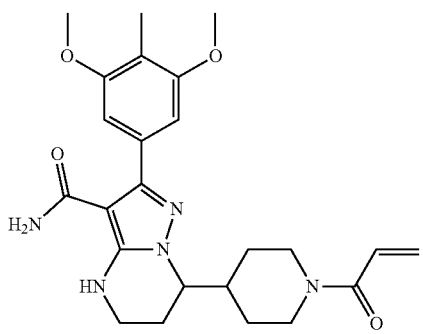 [SMILES: C=CC(=O)N1CCC(C2CCNc3c(C(N)=O)c(-c4cc(OC)c(C)c(OC)c4)nn32)CC1]

Step 1: 2-((3,5-dimethoxy-4-methylphenyl)(hydroxy)methylene)malononitrile

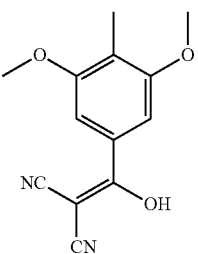

To a mixture of 3,5-dimethoxy-4-methylbenzoic acid (5.0 g, 25 mmol), malononitrile (1.65 g, 25 mmol), HOBT (3.4 g, 25 mmol) and EDCI (5.37 g, 25 mmol) in EA (200 mL) was added TEA (7.5 g, 75 mmol). The reaction was stirred at RT for 10 h. The mixture was filtered and the filtrate was washed by sat. NaHCO₃ (50 mL) and H₂O (50 mL), then stirred with 1.5 N HCl (50 mL) for 30 min, washed with NaCl (50 mL) and evaporated to give the product as a yellow solid (5.1 g, 80%). ¹H NMR (400 MHz, DMSO-d₆) δ 6.87 (s, 2H), 3.77 (s, 6H), 1.99 (s, 3H). MS (ESI, m/e) [M+1]⁺ 244.9.

Step 2: 2-((3,5-dimethoxy-4-methylphenyl)(methoxy)methylene)malononitrile

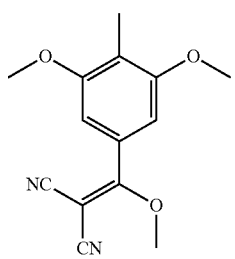

A solution of 2-((3,5-dimethoxy-4-methylphenyl)(hydroxy)methylene)malononitrile (5.0 g, 20 mmol) in trimethoxymethane (50 mL) was stirred at 100° C. for 10 h, then evaporated to give the crude product as a brown oil (5.5 g). MS (ESI, m/e) [M+1]⁺ 259.1.

Step 3: 5-amino-3-(3,5-dimethoxy-4-methylphenyl)-1H-pyrazole-4-carbonitrile

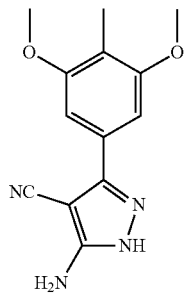 [SMILES: COc1cc(-c2n[nH]c(N)c2C#N)cc(OC)c1C]

To a solution of 2-((3,5-dimethoxy-4-methylphenyl)(methoxy)methylene) malononitrile (5.0 g, 19 mmol) in EtOH (50 mL) was added hydrazine hydrate (2.0 mL) at 0° C. Then the reaction was allowed to warm to RT and stirred for 2 h. The mixture was evaporated to give the crude product as a brown oil (6.0 g). MS (ESI, m/e) [M+1]⁺ 259.1.

Step 4: tert-butyl 4-(3-cyano-2-(3,5-dimethoxy-4-methylphenyl)pyrazolo[1,5-a]pyrimidin-7-yl)piperidine-1-carboxylate

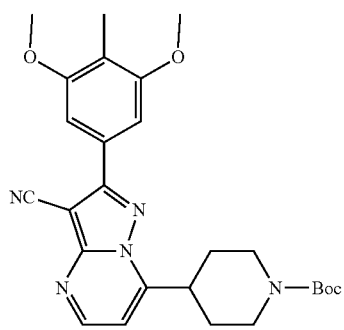 [SMILES: COc1cc(-c2nn3c(C4CCN(C(=O)OC(C)(C)C)CC4)ccnc3c2C#N)cc(OC)c1C]

To a solution of 5-amino-3-(3,5-dimethoxy-4-methylphenyl)-1H-pyrazole-4-carbonitrile (3.0 g, 11.6 mmol) in toluene (50 mL) and AcOH (10 mL) was added tert-butyl (E)-4-(3-(dimethylamino)acryloyl)piperidine-1-carboxylate (ref: PCT/CN2016/095510, 3.27 g, 11.6 mmol). The reaction was stirred at 110° C. for 16 h. The reaction was cooled to RT and evaporated under reduced pressure. EA (30 mL) was added to the residue. The solid was collected by filtration and dried to give the product as a yellow solid (2.0 g, 36%). MS (ESI, m/e) [M+1]⁺ 477.8.

Step 5: tert-butyl 4-(3-cyano-2-(3,5-dimethoxy-4-methylphenyl)-4,5,6,7-tetrahydropyrazolo[1,5-a]pyrimidin-7-yl)piperidine-1-carboxylate

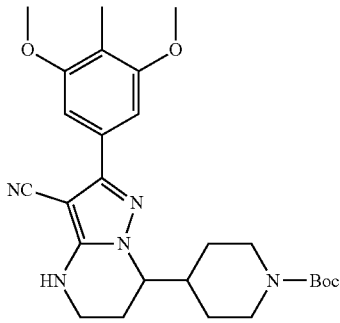 [SMILES: COc1cc(-c2nn3c(c2C#N)NCCC3C2CCN(C(=O)OC(C)(C)C)CC2)cc(OC)c1C]

To a suspension of tert-butyl 4-(3-cyano-2-(3,5-dimethoxy-4-methylphenyl)pyrazolo[1,5-a]pyrimidin-7-yl)piperidine-1-carboxylate (2.0 g, 4.1 mmol) in MeOH (500 mL) was added NaBH$_4$ (465 mg, 12.5 mmol) in portions over 30 min. The reaction was stirred at RT for 2 h. When the system turned clear, the starting material was consumed, the mixture was evaporated, the residue was partitioned between DCM (500 mL) and H$_2$O (300 mL). The organic phase was evaporated to give the crude product as a light yellow solid (2.3 g). MS (ESI, m/e) [M+1]$^+$ 481.8.

Step 6: 2-(3,5-dimethoxy-4-methylphenyl)-7-(piperidin-4-yl)-4,5,6,7-tetrahydropyrazolo[1,5-a]pyrimidine-3-carboxamide

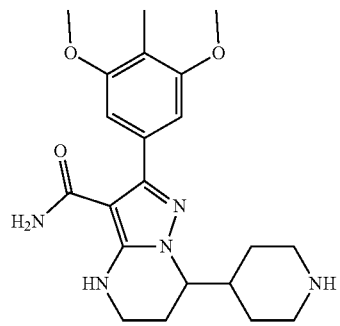 [SMILES: COc1cc(-c2nn3c(c2C(N)=O)NCCC3C2CCNCC2)cc(OC)c1C]

A solution of tert-butyl 4-(3-cyano-2-(3,5-dimethoxy-4-methylphenyl)-4,5,6,7-tetrahydropyrazolo[1,5-a]pyrimidin-7-yl)piperidine-1-carboxylate (2.3 g, 4.78 mmol) in methanesulfonic acid (5 mL) was heated at 100° C. for 2 h. The reaction was then cooled to RT and added dropwise to a system of sat. NaHCO$_3$ (100 mL) and DCM (50 mL). The organic phase was washed with sat. NaCl (50 mL), evaporated to give the desired product as a light yellow solid (1.5 g, 78.6%). MS (ESI, m/e) [M+1]$^+$ 399.8.

Step 7: 7-(1-acryloylpiperidin-4-yl)-2-(3,5-dimethoxy-4-methylphenyl)-4,5,6,7-tetrahydropyrazolo[1,5-a]pyrimidine-3-carboxamide

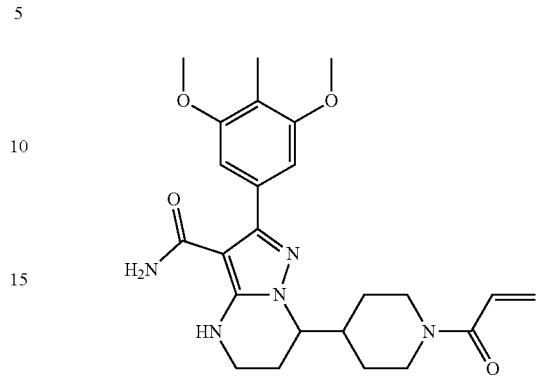

To a mixture of 2-(3,5-dimethoxy-4-methylphenyl)-7-(piperidin-4-yl)-4,5,6,7-tetrahydropyrazolo[1,5-a]pyrimidine-3-carboxamide (1.5 g, 3.9 mmol) in sat. NaHCO$_3$ (20 mL) and DCM (50 mL) was added acryloyl chloride (354 mg, 3.9 mmol) dropwise over 3 min at 0° C. The reaction was allowed to warm to RT and stirred for 2 h. Then the organic phase was washed with sat. NH$_4$Cl (30 mL) and sat. NaCl (30 mL), evaporated and purified by flash column chromatography (eluted with DCM:MeOH=50:1) to yield the compound (400 mg, 23.4%).

Example A1a and A1b: (S or R)-7-(1-acryloylpiperidin-4-yl)-2-(3,5-dimethoxy-4-methylphenyl)-4,5,6,7-tetrahydropyrazolo[1,5-a]pyrimidine-3-carboxamide and (R or S)-7-(1-acryloylpiperidin-4-yl)-2-(3,5-dimethoxy-4-methylphenyl)-4,5,6,7-tetrahydropyrazolo[1,5-a]pyrimidine-3-carboxamide A1a (Faster isomer)

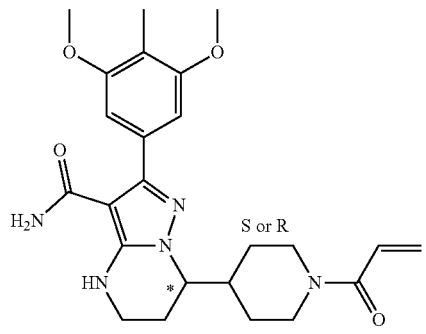 [SMILES: C=CC(=O)N1CCC(C2CCNc3c(C(N)=O)c(-c4cc(OC)c(C)c(OC)c4)nn32)CC1]

A1b (Slower isomer)

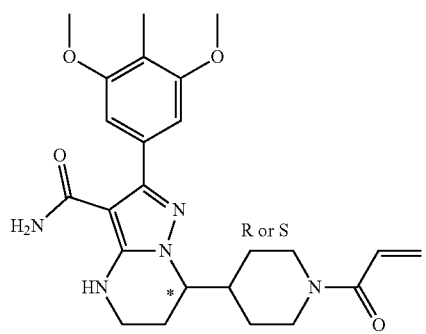

Two enantiomers A1a (faster isomer) and A1b (slower isomer) were separated by chiral preparative HPLC. The chiral separation conditions are shown below. The faster enantiomer was eluted at retention time of 6.4 min to give 185 mg of product. The slower enantiomer was eluted at retention time of 8.2 min to give 181 mg of product. $^1$H NMR (400 MHz, DMSO-$d_6$) δ 6.79 (dd, J=16.8, 10.4 Hz, 1H), 6.71 (s, 2H), 6.07 (dd, J=16.8, 2.4, Hz, 1H), 5.64 (dd, J=10.4, 2.4 Hz, 1H), 4.54-4.36 (m, 1H), 4.17-3.97 (m, 2H), 3.78 (s, 6H), 3.36-3.22 (m, 2H), 3.07-2.88 (m, 1H), 2.65-2.50 (m, 1H), 2.32-2.15 (m, 1H), 2.10-1.96 (m, 1H), 2.03 (s, 3H), 1.96-1.52 (m, 3H), 1.37-1.13 (m, 2H). MS (ESI, m/e) [M+1]$^+$ 453.8.

| Column | CHIRAL ART Cellulose-SB |
|---|---|
| Column size | 2 cm × 25 cm, 5 um |
| Injection | 0.5 mL |
| Mobile phase | Hex:EtOH = 50:50 |
| Flow rate | 20 ml/min |
| Wave length | UV 220 nm |
| Temperature | 25° C. |
| Sample solution | 45.6 mg/ml in MeOH:DCM = 1:1 |
| Prep-HPLC equipment | Prep-Gilson-HPLC |

The absolute stereochemistry of the more potent compound A1a was confirmed to be (S)-configuration on the chiral carbon atom by X-ray single crystal diffraction as shown in FIG. 3. Data collection were performed on a Bruker D8 VENTURE (Cα/Kα radiation, λ=1.54178 Å) diffractometer and analyzed with the APEX3 software package. The Flack parameter was refined to 0.00(4).

A1a

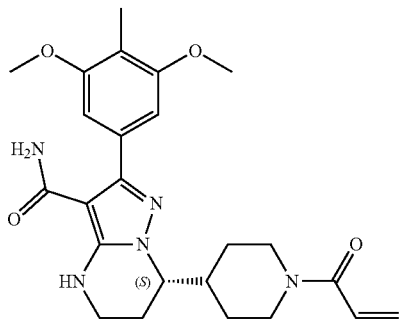

Accordingly the absolute stereochemistry of compound A1b was assigned to be (R)-configuration.

A1b

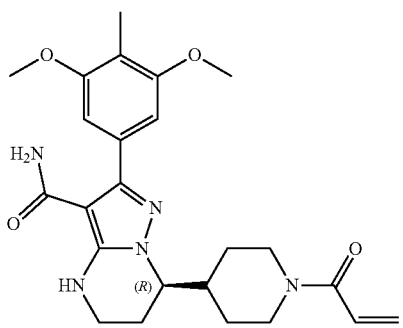

Example A2: 7-(1-acryloylpiperidin-4-yl)-2-(4-cyclopropyl-3,5-dimethoxyphenyl)-4,5,6,7-tetrahydropyrazolo[1,5-a]pyrimidine-3-carboxamide

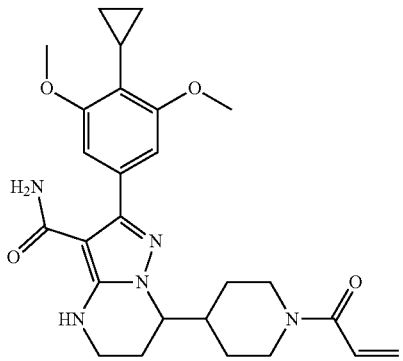 [SMILES: C=CC(=O)N1CCC(C2CCNc3c(C(N)=O)c(-c4cc(OC)c(C5CC5)c(OC)c4)nn32)CC1]

Step 1: methyl 4-bromo-3,5-dimethoxybenzoate

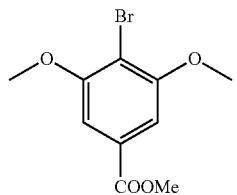

A mixture of methyl 4-bromo-3,5-dihydroxybenzoate (10 g, 40.5 mmol), CH$_3$I (14.2 g, 101.2 mmol), K$_2$CO$_3$ (16.8 g, 121.5 mmol) in 100 mL of DMF was heated at 50° C. for 16 h. After cooling down to RT the mixture was poured into 200 mL of water, extracted with EA (100 mL×3). The combined organic layers were washed with brine, dried over Na$_2$SO$_4$, concentrated to give the product as an off-white solid (10.5 g, 94.6%). MS (ESI) m/e [M+1]$^+$ 274.7 and 276.7.

Step 2: 4-bromo-3,5-dimethoxybenzoic Acid

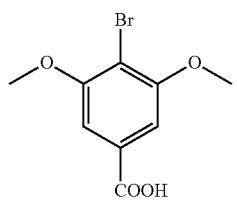

A mixture of methyl 4-bromo-3,5-dimethoxybenzoate (10.5 g, 38.2 mmol), LiOH.H$_2$O (4.8 g, 114.5 mmol) in THF (80 mL) and H$_2$O (80 mL) was heated to reflux for 16 h. The mixture was concentrated to remove the organic solvent under reduced pressure, the residue was adjusted to pH=1-2 with 6 N HCl, extracted with EA (10 mL×3). The combined organic layers were washed with brine, dried over Na$_2$SO$_4$, filtered and concentrated to give the product as yellow solid (8.2 g, 82.2%). MS (ESI) m/e [M+1]$^+$ 260.7 and 262.7.

Step 3: 2-((4-bromo-3,5-dimethoxyphenyl)(hydroxy)methylene)malononitrile

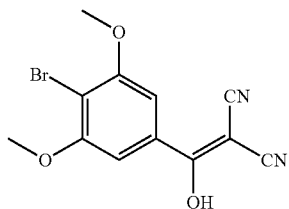 [SMILES: COc1cc(C(O)=C(C#N)C#N)cc(OC)c1Br]

A mixture of 4-bromo-3,5-dimethoxybenzoic acid (7.5 g, 28.7 mmol), propanedinitrile (1.89 g, 28.7 mmol), EDCI (5.51 g, 28.7 mmol), HOBT (3.87 g, 28.7 mmol) and TEA (5.80 g, 28.7 mmol) in EA (100 mL) was stirred at RT for 16 h. The mixture was then washed with 6 N HCl (100 mL). The organic layer was dried over $Na_2SO_4$, filtered and concentrated to give the product as a yellow solid (8.0 g, 90.3%). MS (ESI, m/e) $[M+1]^+$ 308.7 and 310.7.

Step 4: 2-((4-bromo-3,5-dimethoxyphenyl)(methoxy)methylene)malononitrile

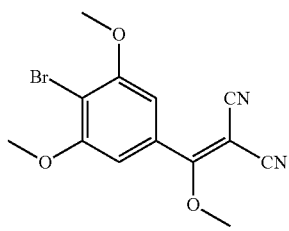 [SMILES: COC(=C(C#N)C#N)c1cc(OC)c(Br)c(OC)c1]

A solution of 2-((4-bromo-3,5-dimethoxyphenyl)(hydroxy)methylene)malononitrile (8.0 g, 25.9 mmol) in $CH(OMe)_3$ (100 mL) was heated to reflux for 4 h. Then the mixture was concentrated to give the crude product as brown oil (8.2 g, 98.1%). MS (ESI) m/e $[M+1]^+$ 312.7 and 314.7.

Step 5: 5-amino-3-(4-bromo-3,5-dimethoxyphenyl)-1H-pyrazole-4-carbonitrile

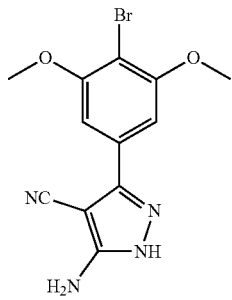

A mixture of 2-((4-bromo-3,5-dimethoxyphenyl)(methoxy)methylene)malononitrile (8.2 g, 25.4 mmol) and hydrazine hydrate (5.0 mL) in EtOH (50 mL) was stirred at RT for 2 h. Then the mixture was filtrated to give the product as a yellow solid (5.5 g, 67.1%).

Step 6: tert-butyl 4-(2-(4-bromo-3,5-dimethoxyphenyl)-3-cyanopyrazolo[1,5-a]pyrimidin-7-yl)piperidine-1-carboxylate

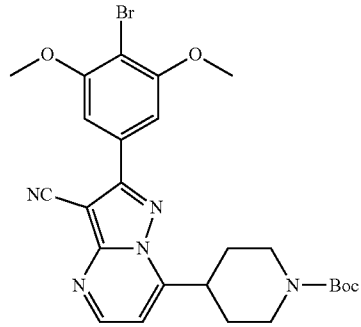 [SMILES: COc1cc(-c2nn3c(C4CCN(C(=O)OC(C)(C)C)CC4)ccnc3c2C#N)cc(OC)c1Br]

A mixture of 5-amino-3-(4-bromo-3,5-dimethoxyphenyl)-1H-pyrazole-4-carbonitrile (5.5 g, 17.0 mmol) and tert-butyl 4-(3-(dimethylamino)acryloyl) piperidine-1-carboxylate (ref: PCT/CN2016/095510, 4.8 g, 17.0 mmol) in HOAc (10 mL) and toluene (50 mL) was heated to 100° C. for 16 h. Then the mixture was filtered to give the product as a yellow solid (6.5 g, 70.3%). MS (ESI) m/e $[M+1]^+$ 542.2 and 544.1.

Step 7: tert-butyl 4-(3-cyano-2-(4-cyclopropyl-3,5-dimethoxyphenyl)pyrazolo[1,5-a]pyrimidin-7-yl)piperidine-1-carboxylate

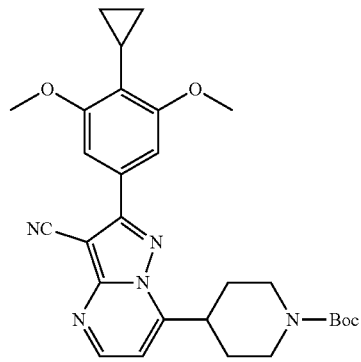 [SMILES: COc1cc(-c2nn3c(C4CCN(C(=O)OC(C)(C)C)CC4)ccnc3c2C#N)cc(OC)c1C1CC1]

A mixture of tert-butyl 4-(2-(4-bromo-3,5-dimethoxyphenyl)-3-cyanopyrazolo[1,5-a]pyrimidin-7-yl)piperidine-1-carboxylate (500 mg, 0.90 mmol), cyclopropylboronic acid (150 mg, 1.80 mmol), $Pd(dppf)Cl_2$ (100 mg, 0.90 mmol) and $K_3PO_4$ (570 mg, 2.70 mmol) in dioxane (50 mL) was heated to 100° C. for 16 h under $N_2$ atmosphere. The mixture was filtered, concentrated and purified by column chromatograph on silica gel using EA/PE (1/1) as eluent to afford the product as a yellow solid (150 mg, 33.0%). MS (ESI) m/e $[M+1]^+$ 504.3.

Step 8: tert-butyl 4-(3-cyano-2-(4-cyclopropyl-3,5-dimethoxyphenyl)-4,5,6,7-tetrahydropyrazolo[1,5-a]pyrimidin-7-yl)piperidine-1-carboxylate

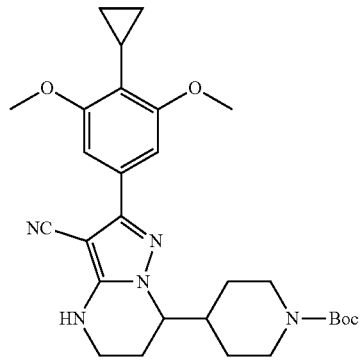 [SMILES: COc1cc(-c2nn3c(c2C#N)NCCC3C2CCN(C(=O)OC(C)(C)C)CC2)cc(OC)c1C1CC1]

A mixture of tert-butyl 4-(3-cyano-2-(4-cyclopropyl-3,5-dimethoxyphenyl)pyrazolo [1,5-a]pyrimidin-7-yl)piperidine-1-carboxylate (150 mg, 0.30 mmol), 10% w/w Pd/C (50 mg) in MeOH (20 mL) and DCM (20 mL) was stirred for 16 h under a balloon of $H_2$. The mixture was filtered, concentrated to give the product as a yellow solid (120 mg, 80%). MS (ESI, m/e) $[M+1]^+$ 508.3.

Step 9: tert-butyl 4-(3-carbamoyl-2-(4-cyclopropyl-3,5-dimethoxyphenyl)-4,5,6,7-tetrahydropyrazolo[1,5-a]pyrimidin-7-yl)piperidine-1-carboxylate

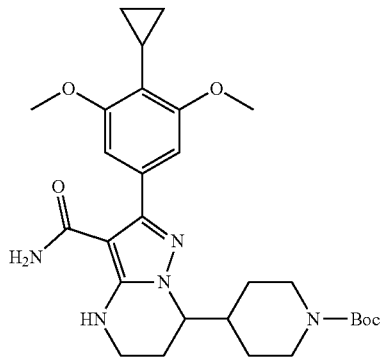 [SMILES: COc1cc(-c2nn3c(c2C(N)=O)NCCC3C2CCN(C(=O)OC(C)(C)C)CC2)cc(OC)c1C1CC1]

To a mixture of tert-butyl 4-(3-cyano-2-(4-cyclopropyl-3,5-dimethoxyphenyl)-4,5,6,7-tetrahydropyrazolo[1,5-a]pyrimidin-7-yl)piperidine-1-carboxylate (120 mg, 0.24 mmol), DMSO (2 mL), aqueous NaOH (3N, 2 mL) in EtOH (20 mL) was slowly added $H_2O_2$ (2 mL, 30% solution) at 65° C. The reaction mixture was stirred at 65° C. for 1 h, cooled to RT, concentrated to remove EtOH. The residue was partitioned between water (50 mL) and EA (50 mL). The aqueous phase was extracted with EA (50 mL×2). The combined organic layers were washed with brine, dried over $Na_2SO_4$ and concentrated to give the product as a yellow solid (80 mg, 63.5%). MS (ESI, m/e) $[M+1]^+$ 526.3.

Step 10: 2-(4-cyclopropyl-3,5-dimethoxyphenyl)-7-(piperidin-4-yl)-4,5,6,7-tetrahydropyrazolo[1,5-a]pyrimidine-3-carboxamide

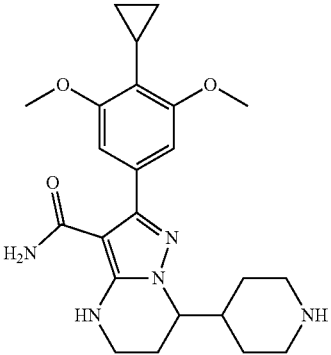 [SMILES: COc1cc(-c2nn3c(c2C(N)=O)NCCC3C2CCNCC2)cc(OC)c1C1CC1]

A solution of tert-butyl 4-(3-carbamoyl-2-(4-cyclopropyl-3,5-dimethoxyphenyl)-4,5,6,7-tetrahydropyrazolo[1,5-a]pyrimidin-7-yl)piperidine-1-carboxylate (80 mg, 0.15 mmol) in TFA/DCM (5 mL/15 mL) was stirred at RT for 16 h. The mixture was concentrated to remove the solvent and the residue was partitioned between aqueous $NaHCO_3$ solution (50 mL) and DCM (50 mL). The organic layer was dried over $Na_2SO_4$, concentrated to get the product as a yellow solid (55 mg, 85.9%). MS (ESI, m/e) $[M+1]^+$ 426.3.

Step 11: 7-(1-acryloylpiperidin-4-yl)-2-(4-cyclopropyl-3,5-dimethoxyphenyl)-4,5,6,7-tetrahydropyrazolo[1,5-a]pyrimidine-3-carboxamide

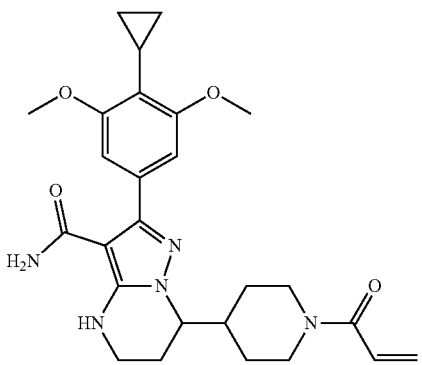 [SMILES: C=CC(=O)N1CCC(C2CCNc3c(C(N)=O)c(-c4cc(OC)c(C5CC5)c(OC)c4)nn32)CC1]

To a mixture of 2-(4-cyclopropyl-3,5-dimethoxyphenyl)-7-(piperidin-4-yl)-4,5,6,7-tetrahydropyrazolo[1,5-a]pyrimidine-3-carboxamide (55 mg, 0.13 mmol), $NaHCO_3$ (56 mg, 0.65 mmol) in DCM (10 mL) and $H_2O$ (10 mL) was added acryloyl chloride (14 mg, 0.16 mmol) at RT. After the reaction was completed, the organic layer was dried over $Na_2SO_4$, concentrated and further purified by Prep-TLC (DCM:MeOH=20:1) to afford the product (40 mg, 64.5%). $^1$H NMR (400 MHz, DMSO-$d_6$) δ 6.79 (dd, J=16.8, 10.8 Hz, 1H), 6.73 (br s, 1H), 6.68 (s, 2H), 6.07 (dd, J=16.8, 2.2 Hz, 1H), 5.64 (d, J=10.8 Hz, 1H), 4.54-4.40 (m, 1H), 4.15-3.97 (m, 2H), 3.75 (s, 6H), 3.50-3.20 (m, 3H), 3.05-2.90 (m, 1H), 2.63-2.52 (m, 1H), 2.30-2.15 (m, 1H), 2.10-1.81 (m, 3H), 1.77-1.10 (m, 3H), 1.02-0.90 (m, 2H), 0.82-0.68 (m, 2H). MS (ESI, m/e) $[M+1]^+$ 480.2.

Example A2a and A2b: (S or R)-7-(1-acryloylpiperidin-4-yl)-2-(4-cyclopropyl-3,5-dimethoxyphenyl)-4,5,6,7-tetrahydropyrazolo[1,5-a]pyrimidine-3-carboxamide and (R or S)-7-(1-acryloylpiperidin-4-yl)-2-(4-cyclopropyl-3,5-dimethoxyphenyl)-4,5,6,7-tetrahydropyrazolo[1,5-a]pyrimidine-3-carboxamide

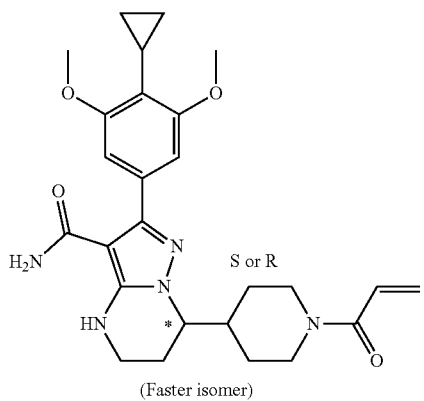

A2a
(Faster isomer)

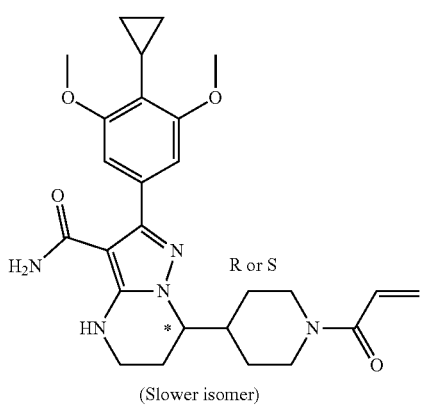

A2b
(Slower isomer)

Two enantiomers A2a (faster isomer) and A2b (slower isomer) were separated by chiral preparative HPLC. The chiral separation conditions are shown below. The faster enantiomer was eluted at retention time of 7.2 min to give 231 mg. The slower enantiomer was eluted at retention time of 10.0 min to give 236 mg.

| Column | CHIRAL ART Cellulose-SB |
|---|---|
| Column size | 2 cm × 25 cm, 5 um |
| Injection | 0.6 mL |
| Mobile phase | CO$_2$:MeOH = 50:50 |
| Flow rate | 40 ml/min |
| Wave length | UV 220 nm |
| Temperature | 25° C. |
| Sample solution | 24.3 mg/ml in MeOH |
| Prep-HPLC equipment | Prep-SFC80 |

A2a was assigned to (S)-configuration and A2b was assigned to (R)-configuration:

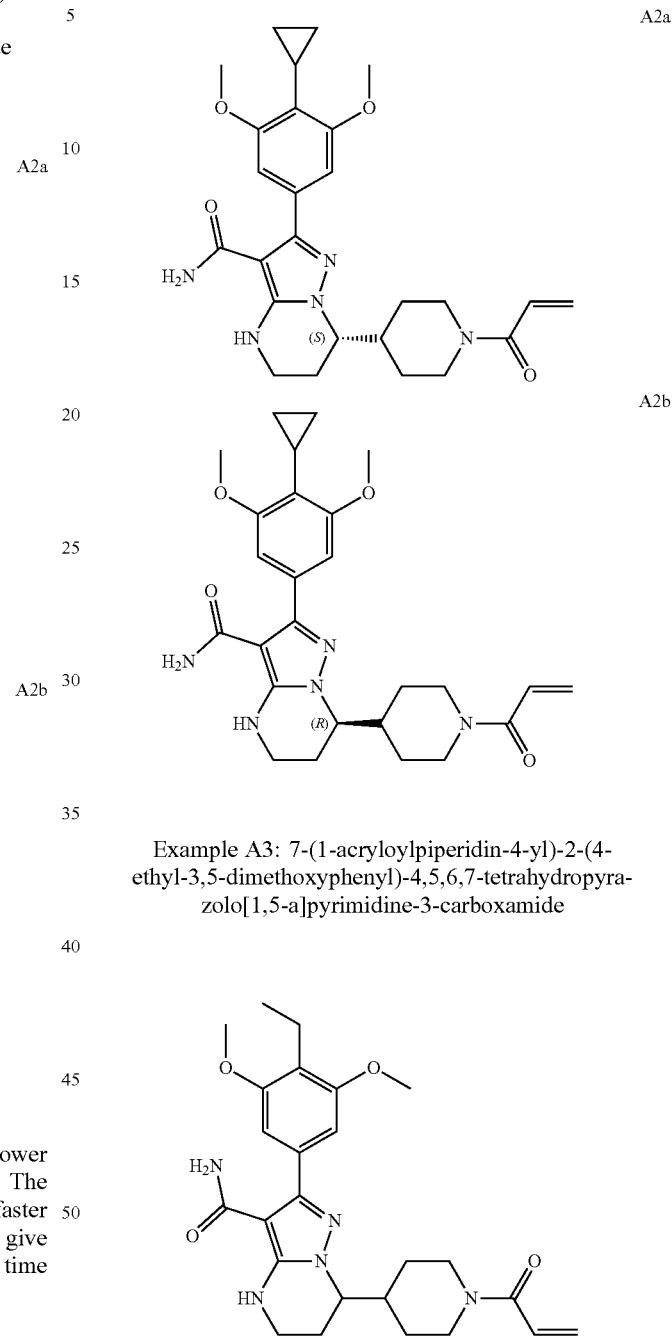

Example A3: 7-(1-acryloylpiperidin-4-yl)-2-(4-ethyl-3,5-dimethoxyphenyl)-4,5,6,7-tetrahydropyrazolo[1,5-a]pyrimidine-3-carboxamide Example A3 was synthesized from tert-butyl 4-(2-(4-bromo-3,5-dimethoxyphenyl)-3-cyanopyrazolo[1,5-a]pyrimidin-7-yl)piperidine-1-carboxylate and 4,4,5,5-tetramethyl-2-vinyl-1,3,2-dioxaborolane following the procedures similar to those in Example A2. $^1$H NMR (400 MHz, DMSO-d$_6$) δ 6.76 (dd, J=16.8, 10.2 Hz, 1H), 6.67 (s, 2H), 6.03 (dd, J=16.8, 2.2 Hz, 1H), 5.60 (d, J=10.2 Hz, 1H), 4.50-4.39 (m, 1H), 4.12-3.94 (m, 2H), 3.75 (s, 6H), 3.30-3.22 (m, 2H), 3.02-2.89 (m, 1H), 2.56 (q, J=7.4 Hz, 2H), 2.54-2.50 (m, 1H), 2.27-1.47 (m, 5H), 1.32-1.09 (m, 2H), 0.99 (t, J=7.4 Hz, 3H). MS (ESI, m/e) [M+1]$^+$ 468.2.

Example A4: 7-(1-acryloylpiperidin-4-yl)-2-(3,5-dimethoxy-4-propylphenyl)-4,5,6,7-tetrahydropyrazolo[1,5-a]pyrimidine-3-carboxamide

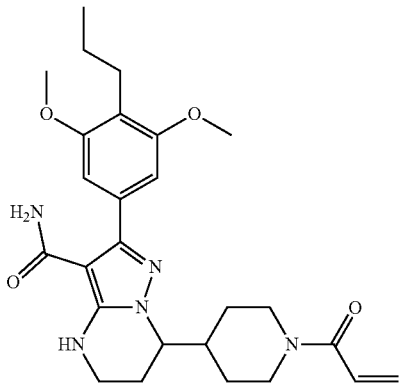 [SMILES: C=CC(=O)N1CCC(C2CCNc3c(C(N)=O)c(-c4cc(OC)c(CCC)c(OC)c4)nn32)CC1]

Example A4 was a byproduct when preparing A3 due to the impurity ((E)-4,4,5,5-tetramethyl-2-(prop-1-en-1-yl)-1,3,2-dioxaborolane) in 4,4,5,5-tetramethyl-2-vinyl-1,3,2-dioxaborolane. $^1$H NMR (400 MHz, DMSO-$d_6$) δ 6.76 (dd, J=16.8, 10.2 Hz, 1H), 6.67 (s, 2H), 6.03 (d, J=16.8 Hz, 1H), 5.60 (d, J=10.2 Hz, 1H), 4.52-4.36 (m, 1H), 4.12-3.94 (m, 2H), 3.74 (s, 6H), 3.34-3.20 (m, 2H), 3.04-2.85 (m, 1H), 2.60-2.50 (m, 3H), 2.28-1.48 (m, 5H), 1.47-1.34 (m, 2H), 1.32-1.08 (m, 2H), 0.85 (t, J=7.3 Hz, 3H). MS (ESI, m/e) [M+1]$^+$ 482.3.

Example A5: 7-(1-acryloylpiperidin-4-yl)-2-(4-isopropyl-3,5-dimethoxyphenyl)-4,5,6,7-tetrahydropyrazolo[1,5-a]pyrimidine-3-carboxamide

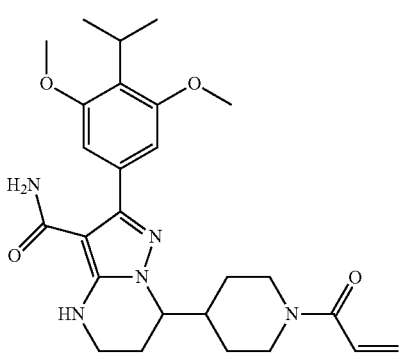 [SMILES: C=CC(=O)N1CCC(C2CCNc3c(C(N)=O)c(-c4cc(OC)c(C(C)C)c(OC)c4)nn32)CC1]

Example A5 was synthesized from tert-butyl 4-(2-(4-bromo-3,5-dimethoxyphenyl)-3-cyanopyrazolo[1,5-a]pyrimidin-7-yl)piperidine-1-carboxylate and 4,4,5,5-tetramethyl-2-(prop-1-en-2-yl)-1,3,2-dioxaborolane following the procedures similar to those in Example A2. $^1$H NMR (400 MHz, DMSO-$d_6$) δ 6.79 (dd, J=16.8, 10.4 Hz, 1H), 6.73 (s, 1H), 6.70 (s, 2H), 6.07 (dd, J=16.8, 2.0 Hz, 1H), 5.64 (d, J=10.4 Hz, 1H), 4.52-4.42 (m, 1H), 4.15-3.95 (m, 2H), 3.77 (s, 6H), 3.62-3.49 (m, 1H), 3.35-3.25 (m, 2H), 3.07-2.89 (m, 1H), 2.58-2.52 (m, 1H), 2.30-1.50 (m, 5H), 1.24 (d, J=6.8 Hz, 6H), 1.35-1.13 (m, 2H). MS (ESI, m/e) [M+1]$^+$ 482.2.

Example A6: 7-(1-acryloylpiperidin-4-yl)-2-(4-bromo-3,5-dimethoxyphenyl)-4,5,6,7-tetrahydropyrazolo[1,5-a]pyrimidine-3-carboxamide

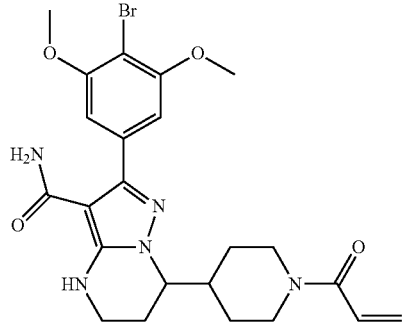 [SMILES: C=CC(=O)N1CCC(C2CCNc3c(C(N)=O)c(-c4cc(OC)c(Br)c(OC)c4)nn32)CC1]

Step 1: Tert-butyl 4-(2-(4-bromo-3,5-dimethoxyphenyl)-3-cyano-4,5,6,7-tetrahydropyrazolo[1,5-a]pyrimidin-7-yl)piperidine-1-carboxylate

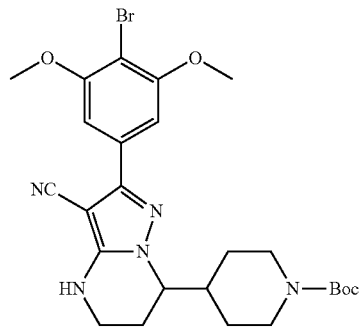 [SMILES: COc1cc(-c2nn3c(c2C#N)NCCC3C2CCN(C(=O)OC(C)(C)C)CC2)cc(OC)c1Br]

To a mixture solution of tert-butyl 4-(2-(4-bromo-3,5-dimethoxyphenyl)-3-cyanopyrazolo[1,5-a]pyrimidin-7-yl)piperidine-1-carboxylate (2.0 g, 3.70 mmol) in MeOH (100 mL) and DCM (100 mL) was added NaBH$_4$ (1.4 g, 37.0 mmol) in portions, then the mixture was stirred for 2 h at RT. The reaction was quenched with H$_2$O (100 mL), concentrated to remove organic solvent. The residue was extracted with EA (50 mL×3). The combined organic layers were washed with brine, dried over Na$_2$SO$_4$, concentrated to afford the product as a yellow solid (1.65 g, 81.7%). MS (ESI, m/e) [M+1]$^+$ 546.1 and 548.1.

Step 2: tert-butyl 4-(2-(4-bromo-3,5-dimethoxyphenyl)-3-carbamoyl-4,5,6,7-tetrahydropyrazolo[1,5-a]pyrimidin-7-yl)piperidine-1-carboxylate

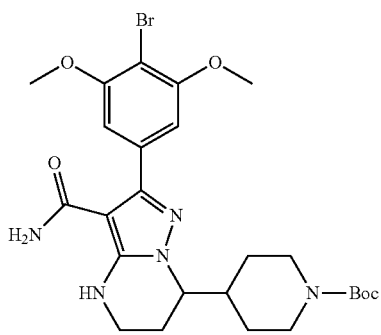 [SMILES: COc1cc(-c2nn3c(c2C(N)=O)NCCC3C2CCN(C(=O)OC(C)(C)C)CC2)cc(OC)c1Br]

To a solution of tert-butyl 4-(2-(4-bromo-3,5-dimethoxyphenyl)-3-cyano-4,5,6,7-tetrahydropyrazolo[1,5-a]pyrimidin-7-yl)piperidine-1-carboxylate (1.65 g, 3.02 mmol), DMSO (10 mL) and aq. NaOH (3 N, 10 mL) in EtOH (50 mL) was slowly added H$_2$O$_2$ (10 mL, 30% solution) at 65° C. The reaction mixture was stirred at 65° C. for 1 h. Then the mixture was concentrated to remove EtOH. The residue was partitioned between water (50 mL) and EA (50 mL), the aqueous phase was extracted with EA (50 mL×3). The combined organic layers were washed with brine, dried over Na$_2$SO$_4$ and concentrated to afford the crude product as a yellow solid (1.05 g, 61.8%). MS (ESI, m/e) [M+1]$^+$ 564.1 and 566.1.

Step 3: 2-(4-bromo-3,5-dimethoxyphenyl)-7-(piperidin-4-yl)-4,5,6,7-tetrahydropyrazolo[1,5-a]pyrimidine-3-carboxamide

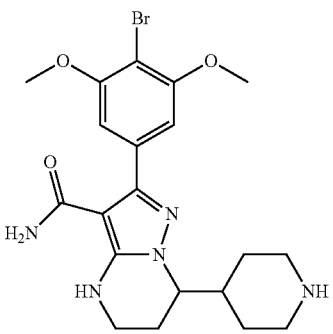 [SMILES: COc1cc(-c2nn3c(c2C(N)=O)NCCC3C2CCNCC2)cc(OC)c1Br]

A solution of tert-butyl 4-(2-(4-bromo-3,5-dimethoxyphenyl)-3-carbamoyl-4,5,6,7-tetrahydropyrazolo[1,5-a]pyrimidin-7-yl)piperidine-1-carboxylate (1.05 g, 1.86 mmol) in TFA/DCM (5 mL/50 mL) was stirred at RT for 16 h. The mixture was concentrated to remove solvent and the residue was partitioned between sat. NaHCO$_3$ (50 mL) and DCM (50 mL). The organic layer was dried over Na$_2$SO$_4$, filtered and concentrated to give the crude product as a yellow solid (680 mg, 82.6%). MS (ESI, m/e) [M+1]$^+$ 464.1 and 466.1.

Step 4: 7-(1-acryloylpiperidin-4-yl)-2-(4-bromo-3,5-dimethoxyphenyl)-4,5,6,7-tetrahydropyrazolo[1,5-a]pyrimidine-3-carboxamide

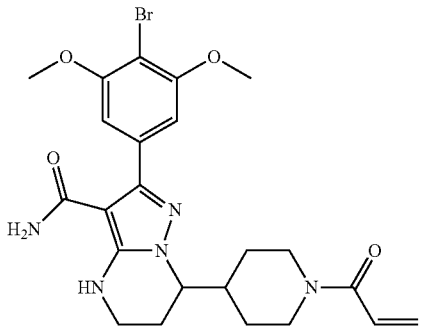 [SMILES: C=CC(=O)N1CCC(C2CCNc3c(C(N)=O)c(-c4cc(OC)c(Br)c(OC)c4)nn32)CC1]

To a solution of 2-(4-bromo-3,5-dimethoxyphenyl)-7-(piperidin-4-yl)-4,5,6,7-tetrahydropyrazolo[1,5-a]pyrimidine-3-carboxamide (680 mg, 1.47 mmol) in sat. NaHCO$_3$ (100 mL) and DCM (100 mL) was added acryloyl chloride (160 mg, 1.76 mmol) at ambient temperature, the reaction was stirred at ambient temperature for about 1 h. The aqueous phase was extracted with DCM (50 mL×3), the combined organic phases were washed with sat. NaCl (50 mL), dried over Na$_2$SO$_4$, concentrated and purified by column chromatograph on silica gel (100-200 mesh, eluent: MeOH:DCM=1:50) to afford the product (550 mg, 72.3%). $^1$H NMR (400 MHz, DMSO-d$_6$) δ 6.83 (s, 2H), 6.77 (dd, J=16.8, 10.4 Hz, 1H), 6.73 (s, 1H), 6.07 (dd, J=16.8, 2.2 Hz, 1H), 5.64 (dd, J=10.4, 2.2 Hz, 1H), 4.53-4.41 (m, 1H), 4.16-3.98 (m, 2H), 3.85 (s, 6H), 3.35-3.25 (m, 2H), 3.05-2.95 (m, 1H), 2.62-2.50 (m, 1H), 2.32-2.18 (m, 1H), 2.10-1.95 (m, 1H), 1.99-1.92 (m, 1H), 1.78-1.72 (m, 1H), 1.62-1.55 (m, 1H), 1.37-1.13 (m, 2H). MS (ESI, m/e) [M+1]$^+$ 518.1 and 520.1.

Example A6a and A6b: (S or R)-7-(1-acryloylpiperidin-4-yl)-2-(4-bromo-3,5-dimethoxyphenyl)-4,5,6,7-tetrahydropyrazolo[1,5-a]pyrimidine-3-carboxamide and (R or S)-7-(1-acryloylpiperidin-4-yl)-2-(4-bromo-3,5-dimethoxyphenyl)-4,5,6,7-tetrahydropyrazolo[1,5-a]pyrimidine-3-carboxamide

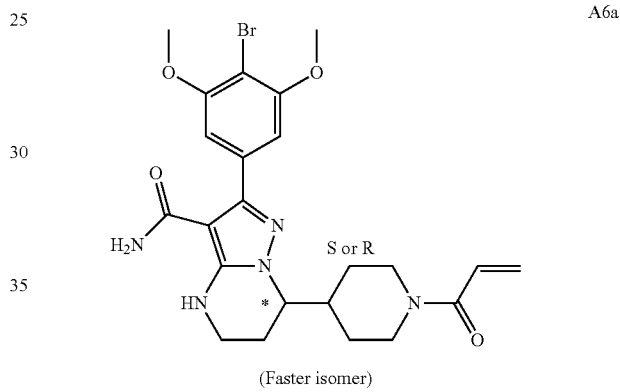

(Faster isomer)

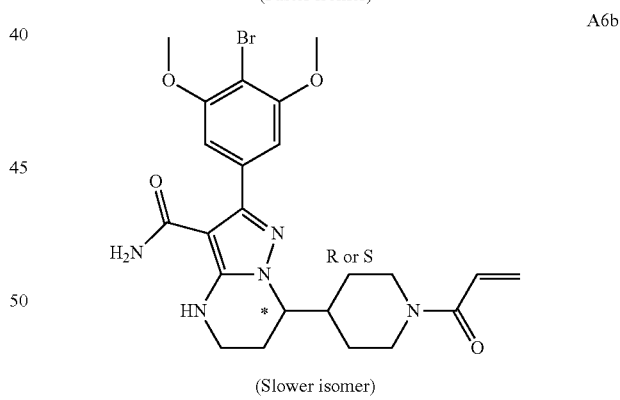

(Slower isomer)

Two enantiomers A6a (faster isomer) and A6b (slower isomer) were separated by chiral preparative HPLC. The chiral separation conditions are shown below. The faster enantiomer was eluted at retention time of 3.2 min to give 294 mg. The slower enantiomer was eluted at retention time of 4.0 min to give 310 mg.

| Column | CHIRAL ART Cellulose-SB |
|---|---|
| Column size | 2 cm × 25 cm, 5 um |
| Injection | 1.0 mL |

| Column | CHIRAL ART Cellulose-SB |
|---|---|
| Mobile phase | $CO_2$:MeOH = 50:50 |
| Flow rate | 45 ml/min |
| Wave length | UV 254 nm |
| Temperature | 25° C. |
| Sample solution | 24.5 mg/ml in MeOH |
| Prep-HPLC equipment | Prep-SFC80 |

A6a was assigned to (S)-configuration and A6b was assigned to (R)-configuration:

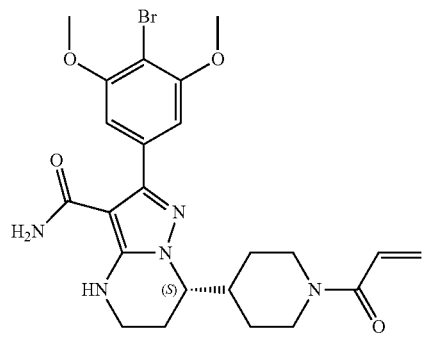

A6a

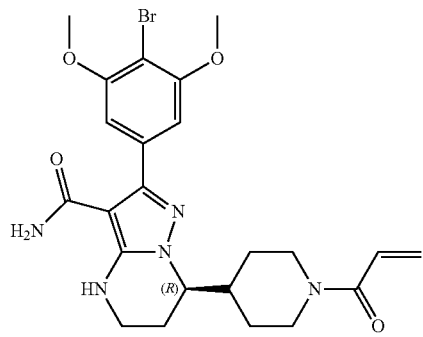

A6b

Example A7: 7-(1-acryloylpiperidin-4-yl)-2-(3,5-dichloro-4-methylphenyl)-4,5,6,7-tetrahydropyrazolo[1,5-a]pyrimidine-3-carboxamide

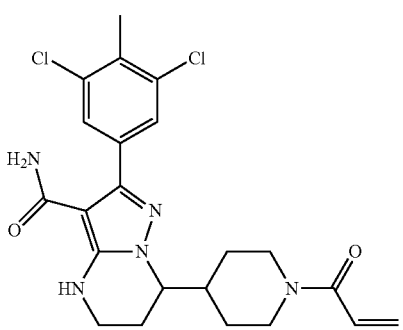 [SMILES: C=CC(=O)N1CCC(C2CCNc3c(C(N)=O)c(-c4cc(Cl)c(C)c(Cl)c4)nn32)CC1]

Example A7 was synthesized from 3,5-dichloro-4-methylbenzoic acid following the procedures similar to those in Example A2 without the Suzuki reaction step. $NaBH_4$ was used in the reduction step. $^1$H NMR (400 MHz, DMSO-$d_6$) δ 7.56 (s, 2H), 6.86-6.72 (m, 1H), 6.60 (s, 1H), 6.07 (dd, J=16.8, 2.2 Hz, 1H), 5.64 (dd, J=10.5, 2.2 Hz, 1H), 4.56-4.40 (m, 1H), 4.20-3.95 (m, 2H), 3.33-3.22 (m, 2H), 3.07-2.89 (m, 1H), 2.69-2.54 (m, 1H), 2.44 (s, 3H), 2.35-2.12 (m, 1H), 2.10-1.82 (m, 2H), 1.78-1.45 (m, 2H), 1.37-1.10 (m, 2H). MS (ESI, m/e) [M+1]$^+$ 462.1.

Example A8: 7-(1-acryloylpiperidin-4-yl)-2-(4-iodo-3,5-dimethoxyphenyl)-4,5,6,7-tetrahydropyrazolo[1,5-a]pyrimidine-3-carboxamide

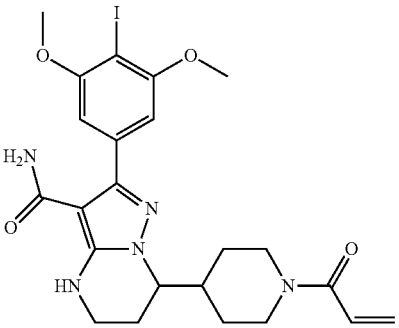 [SMILES: C=CC(=O)N1CCC(C2CCNc3c(C(N)=O)c(-c4cc(OC)c(I)c(OC)c4)nn32)CC1]

Example A8 was synthesized from 4-iodo-3,5-dimethoxybenzoic acid following the procedures similar to those in Example A2 without the Suzuki reaction step. $NaBH_4$ was used in the reduction step. $^1$H NMR (400 MHz, DMSO-$d_6$) δ 6.79 (dd, J=16.6, 10.4 Hz, 1H), 6.74 (s, 2H), 6.07 (dd, J=16.6, 2.2 Hz, 1H), 5.64 (dd, J=10.4, 2.2 Hz, 1H), 4.55-4.42 (m, 1H), 4.15-3.95 (m, 2H), 3.83 (s, 6H), 3.33-3.26 (m, 1H), 3.05-2.90 (m, 2H), 2.63-2.52 (m, 1H), 2.31-1.12 (m, 7H). MS (ESI, m/e) [M+1]$^+$ 565.0.

Example A9: 7-(1-acryloylpiperidin-4-yl)-2-(3,5-dimethoxyphenyl)-4,5,6,7-tetrahydropyrazolo[1,5-a]pyrimidine-3-carboxamide

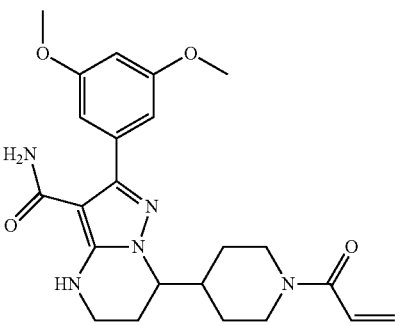 [SMILES: C=CC(=O)N1CCC(C2CCNc3c(C(N)=O)c(-c4cc(OC)cc(OC)c4)nn32)CC1]

Example A9 is a byproduct when preparing Example A8. $^1$H NMR (400 MHz, DMSO-$d_6$) δ 6.85-6.74 (m, 1H), 6.72 (br s, 1H), 6.63-6.58 (m, 2H), 6.57-6.54 (m, 1H), 6.06 (dd, J=16.6, 2.2 Hz, 1H), 5.64 (d, J=10.6 Hz, 1H), 4.52-4.42 (m, 1H), 4.17-3.95 (m, 2H), 3.76 (s, 6H), 3.33-3.26 (m, 2H), 3.07-2.87 (m, 1H), 2.64-2.54 (m, 1H), 2.35-2.15 (m, 1H), 2.10-1.84 (m, 2H), 1.78-1.66 (m, 1H), 1.63-1.48 (m, 1H), 1.35-1.12 (m, 2H). MS (ESI, m/e) [M+1]$^+$ 439.4.

Example A10: 7-(1-acryloylpiperidin-4-yl)-2-(2,6-dimethoxy-[1,1'-biphenyl]-4-yl)-4,5,6,7-tetrahydropyrazolo[1,5-a]pyrimidine-3-carboxamide

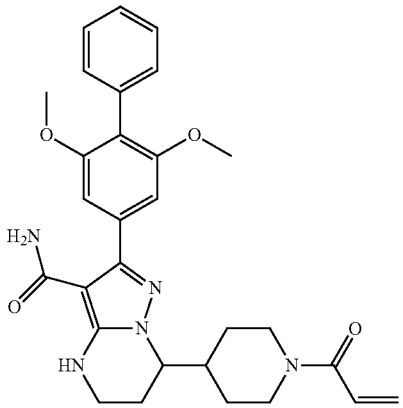 [SMILES: C=CC(=O)N1CCC(C2CCNc3c(C(N)=O)c(-c4cc(OC)c(-c5ccccc5)c(OC)c4)nn32)CC1]

Example A10 was synthesized from tert-butyl 4-(2-(4-bromo-3,5-dimethoxyphenyl)-3-cyanopyrazolo[1,5-a]pyrimidin-7-yl)piperidine-1-carboxylate and phenylboronic acid following the procedures similar to those in Example A2. NaBH$_4$ was used in the reduction step. $^1$H NMR (400 MHz, DMSO-d$_6$) δ 7.39-7.24 (m, 5H), 6.85 (s, 2H), 6.82-6.71 (m, 2H), 6.07 (d, J=16.8 Hz, 1H), 5.64 (d, J=10.4 Hz, 1H), 4.52-4.45 (m, 1H), 4.15-4.00 (m, 2H), 3.71 (s, 6H), 3.05-2.95 (m, 2H), 2.65-2.55 (m, 1H), 2.32-2.25 (m, 1H), 2.08-1.90 (m, 2H), 1.80-1.70 (m, 1H), 1.62-1.55 (m, 1H), 1.35-1.23 (m, 2H). MS (ESI, m/e) [M+1]$^+$ 516.2.

Example A11: 7-(1-acryloylpiperidin-4-yl)-2-(3,5-bis(methoxy-d3)-4-methylphenyl)-4,5,6,7-tetrahydropyrazolo[1,5-a]pyrimidine-3-carboxamide

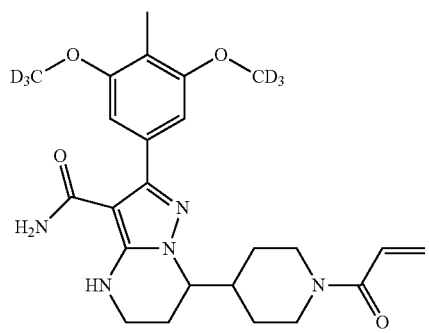 [SMILES: [2H]C([2H])([2H])Oc1cc(-c2nn3c(c2C(N)=O)NCCC3C2CCN(C(=O)C=C)CC2)cc(OC([2H])([2H])[2H])c1C]

Step 1: Methyl 3,5-dihydroxy-4-methylbenzoate

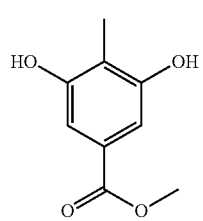

A mixture solution of 3,5-dihydroxy-4-methylbenzoic acid (4.7 g, 27.9 mmol) and H$_2$SO$_4$ (1.0 mL) in methanol (50 mL) was stirred at 60° C. for overnight. Then the mixture solution was concentrated and the residue was dissolved in EA (100 mL), washed with saturated NaHCO$_3$ solution (100 mL×3), dried over Na$_2$SO$_4$, filtered and concentrated to give the product (4.93 g, 96.8%). MS (ESI, m/e) [M+1]$^+$ 183.1.

Step 2: Methyl 3,5-bis(methoxy-d3)-4-methylbenzoate

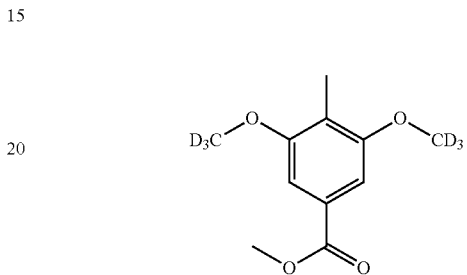

A mixture solution of methyl 3,5-dihydroxy-4-methylbenzoate (5.27 g, 28.9 mmol), CD$_3$I (9.24 g, 63.7 mmol) and K$_2$CO$_3$ (9.97 g, 72.3 mmol) in DMF (50 mL) was stirred at RT for 16 h. Then the mixture solution was concentrated and further purified by chromatography on silica gel eluting with EA/PE=1/5 to give the product (5.3 g, 84.8%) as a white solid. MS (ESI, m/e) [M+1]$^+$ 217.1.

Step 3: 3,5-bis(methoxy-d3)-4-methylbenzoic Acid

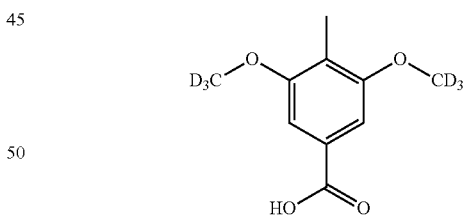

A mixture solution of methyl 3,5-bis(methoxy-d3)-4-methylbenzoate (5.3 g, 24.5 mmol) and NaOH solution (17 mL, 3N) in THF (17 mL) was stirred at 60° C. for 2 h. Then the mixture solution was concentrated. And the residue was adjusted to the pH value of 4-5, extracted with EA (20 mL×3). The combined organic layers were dried over Na$_2$SO$_4$, filtered and concentrated to give the product (4.9 g, 98.4%) as a yellow solid. MS (ESI, m/e) [M+1]$^+$ 203.1.

Step 4: 7-(1-acryloylpiperidin-4-yl)-2-(3,5-bis(methoxy-d3)-4-methylphenyl)-4,5,6,7-tetrahydropyrazolo[1,5-a]pyrimidine-3-carboxamide

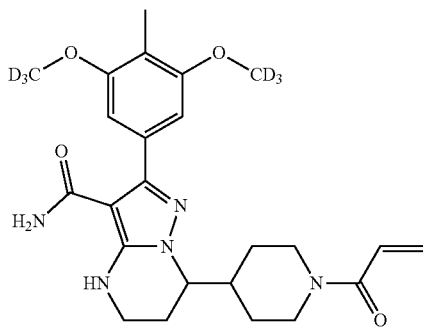 [SMILES: [2H]C([2H])([2H])Oc1cc(-c2nn3c(c2C(N)=O)NCCC3C2CCN(C(=O)C=C)CC2)cc(OC([2H])([2H])[2H])c1C]

Example A11 was then synthesized from 3,5-bis(methoxy-d3)-4-methylbenzoic acid following the procedures similar to those in Example A2 without the Suzuki reaction step. $^1$H NMR (400 MHz, DMSO-d$_6$) δ 6.86-6.72 (m, 2H), 6.70 (s, 2H), 6.06 (d, J=16.8 Hz, 1H), 5.64 (d, J=10.4 Hz, 1H), 4.55-4.40 (m, 1H), 4.18-3.96 (m, 2H), 3.33-3.22 (m, 2H), 3.07-2.89 (m, 1H), 2.70-2.54 (m, 1H), 2.32-2.16 (m, 1H), 2.10-1.96 (m, 1H), 2.03 (s, 3H), 1.95-1.50 (m, 3H), 1.35-1.14 (m, 2H).

Example A11a and A11b: (S or R)-7-(1-acryloylpiperidin-4-yl)-2-(3,5-bis(methoxy-d3)-4-methylphenyl)-4,5,6,7-tetrahydropyrazolo[1,5-a]pyrimidine-3-carboxamide and (R or S)-7-(1-acryloylpiperidin-4-yl)-2-(3,5-bis(methoxy-d3)-4-methylphenyl)-4,5,6,7-tetrahydropyrazolo[1,5-a]pyrimidine-3-carboxamide A11a

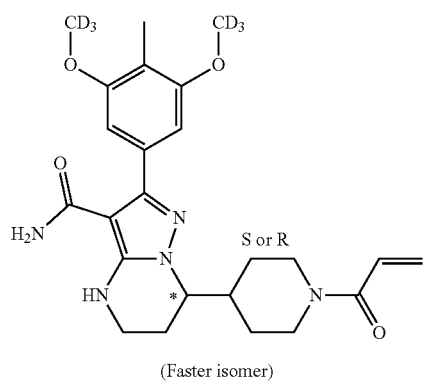

(Faster isomer)

A11b

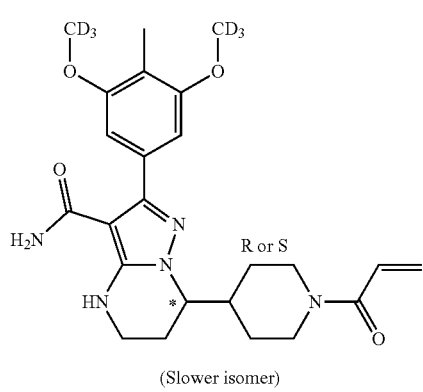

(Slower isomer)

Two enantiomers A11a (faster isomer) and A11b (slower isomer) were separated by chiral preparative HPLC. The chiral separation conditions are shown below. The faster enantiomer was eluted at retention time of around 2.0 min. The slower enantiomer was eluted at retention time of around 2.6 min.

| Column | CHIRALPAK ID |
|---|---|
| Column size | 2 cm × 5 cm, 5 um |
| Injection | 1 mL |
| Mobile phase | (Hex:DCM = 3:1):IPA = 50:50 |
| Flow rate | 16 ml/min |
| Wave length | UV 220 nm |
| Temperature | 25° C. |
| Sample solution | 26.25 mg/ml in EtOH:DCM = 3:1 |
| Prep-HPLC equipment | Prep-Gilson-HPLC |

A11a was assigned to (R)-configuration and A11b was assigned to (S)-configuration:

A11a

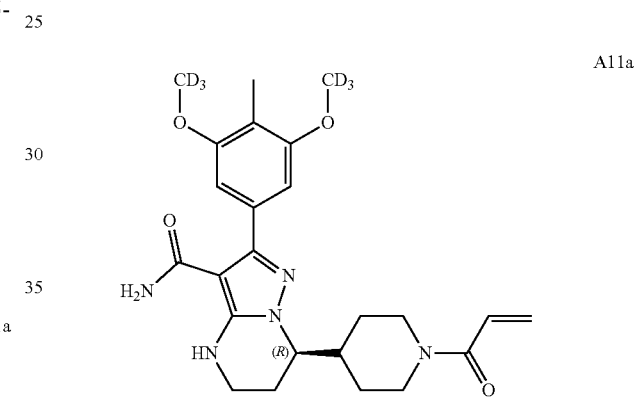

A11b

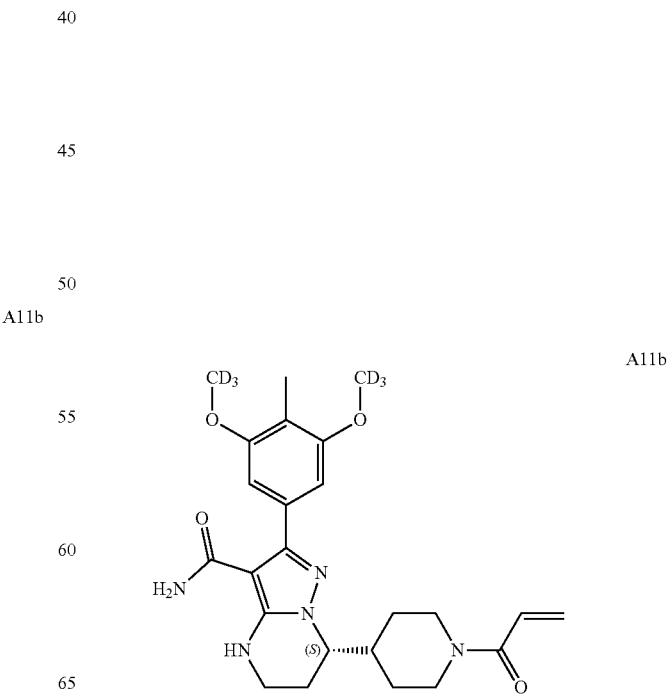

Example A12: 7-(1-acryloylpiperidin-4-yl)-2-(3-ethoxy-5-methoxy-4-methylphenyl)-4,5,6,7-tetrahydropyrazolo[1,5-a]pyrimidine-3-carboxamide

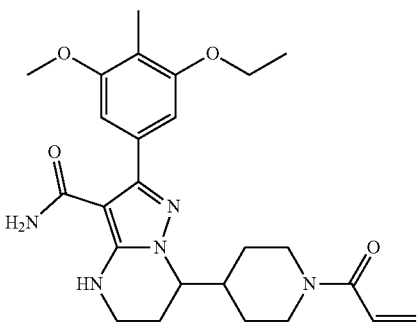 [SMILES: C=CC(=O)N1CCC(C2CCNc3c(C(N)=O)c(-c4cc(OC)c(C)c(OCC)c4)nn32)CC1]

Step 1: methyl 3-hydroxy-5-methoxy-4-methylbenzoate

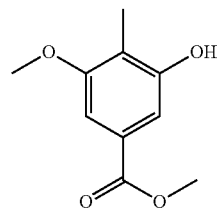

To a mixture solution of methyl 3,5-dihydroxy-4-methylbenzoate (3.0 g, 16.4 mmol) and K$_2$CO$_3$ (4.52 g, 32.8 mmol) in DMF (30 mL) was added CH$_3$I (2.45 g, 17.3 mmol). The mixture was then stirred at RT for 72 h, concentrated under reduced pressure. To the residue was added EA (100 mL), washed with water (100 mL×3), dried over Na$_2$SO$_4$, filtered, concentrated and purified by column chromatography on silica gel (200-300 mesh, eluent: PE:EA=5:1) to give the product as a white solid (1.1 g, 34%). MS (ESI, m/e) [M+1]$^+$ 197.1.

Step 2: methyl 3-ethoxy-5-methoxy-4-methylbenzoate

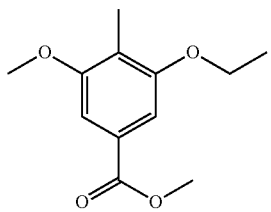 [SMILES: CCOc1cc(C(=O)OC)cc(OC)c1C]

To a mixture solution of methyl 3-hydroxy-5-methoxy-4-methylbenzoate (1.1 g, 5.6 mmol) and K$_2$CO$_3$ (1.05 g, 6.7 mmol) in DMF (30 mL) was added C$_2$H$_5$I (1.55 g, 11.2 mmol). Then the mixture was stirred at RT for 16 h, concentrated under reduced pressure. To the residue was added EA (100 mL), washed with water (20 mL×3), dried over Na$_2$SO$_4$, filtered and concentrated to give the product (1.2 g, 95.2%). MS (ESI, m/e) [M+1]$^+$ 225.1.

Step 3: 3-ethoxy-5-methoxy-4-methylbenzoic Acid

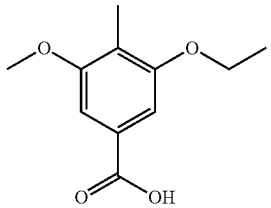

A mixture solution of methyl 3-ethoxy-5-methoxy-4-methylbenzoate (1.2 g, 5.4 mmol) and NaOH (3.6 mL, 3N) in THF (5 mL) and H$_2$O (1 mL) was stirred at RT for 16 h, and then heated to 60° C. for 2 h. Then the mixture solution was acidified with 6N HCl and extracted with EA (20 mL×3). The organic layers were combined, dried over Na$_2$SO$_4$, filtered and concentrated to give the product (1.1 g, 97.8%) as a yellow solid. MS (ESI, m/e) [M+1]$^+$ 211.1.

Step 4: 7-(1-acryloylpiperidin-4-yl)-2-(3-ethoxy-5-methoxy-4-methylphenyl)-4,5,6,7-tetrahydropyrazolo[1,5-a]pyrimidine-3-carboxamide

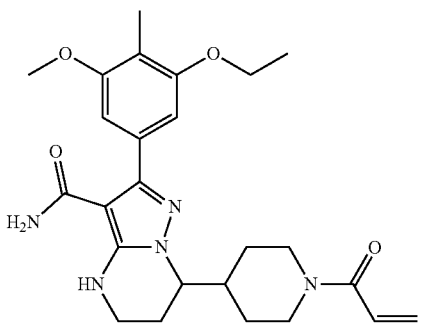 [SMILES: C=CC(=O)N1CCC(C2CCNc3c(C(N)=O)c(-c4cc(OC)c(C)c(OCC)c4)nn32)CC1]

Example A12 was then synthesized from 3-ethoxy-5-methoxy-4-methylbenzoic acid following the procedures similar to those in Example A2 without the Suzuki reaction step. $^1$H NMR (400 MHz, DMSO-d$_6$) δ 6.79 (dd, J=16.8, 10.6 Hz, 1H), 6.69 (s, 2H), 6.07 (d, J=16.8 Hz, 1H), 5.64 (d, J=10.6 Hz, 1H), 4.59-4.39 (m, 1H), 4.19-3.91 (m, 4H), 3.78 (s, 3H), 3.36-3.23 (m, 2H), 3.10-2.90 (m, 1H), 2.70-2.52 (m, 1H), 2.35-2.15 (m, 1H), 2.03 (s, 3H), 2.12-1.96 (m, 1H), 1.97-1.52 (m, 3H), 1.34 (t, J=6.8 Hz, 3H) 1.36-1.12 (m, 2H). MS (ESI, m/e) [M+1]$^+$ 468.2.

Example A13: 7-(1-acryloylpiperidin-4-yl)-2-(3,5-diethoxy-4-methylphenyl)-4,5,6,7-tetrahydropyrazolo[1,5-a]pyrimidine-3-carboxamide

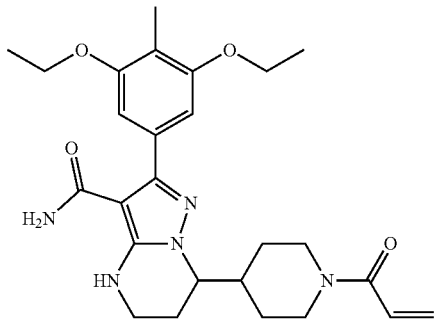 [SMILES: C=CC(=O)N1CCC(C2CCNc3c(C(N)=O)c(-c4cc(OCC)c(C)c(OCC)c4)nn32)CC1]

Example A13 was synthesized from methyl 3,5-dihydroxy-4-methylbenzoate following the procedures similar to those in Example A11. $^1$H NMR (400 MHz, DMSO-$d_6$) δ 6.79 (dd, J=16.6, 10.4 Hz, 1H), 6.72 (s, 1H), 6.66 (s, 2H), 6.07 (dd, J=16.6, 2.2 Hz, 1H), 5.64 (dd, J=10.4, 2.2 Hz, 1H), 4.55-4.39 (m, 1H), 4.15-3.96 (m, 6H), 3.33-3.25 (m, 2H), 3.08-2.90 (m, 1H), 2.54-2.52 (m, 1H), 2.31-2.15 (m, 1H), 2.04 (s, 3H), 2.10-1.96 (m, 1H), 1.96-1.51 (m, 3H), 1.36 (t, J=6.8 Hz, 6H), 1.41-1.09 (m, 2H).

Example A14: 7-(1-acryloylpiperidin-4-yl)-2-(3,4,5-trimethoxyphenyl)-4,5,6,7-tetrahydropyrazolo[1,5-a]pyrimidine-3-carboxamide

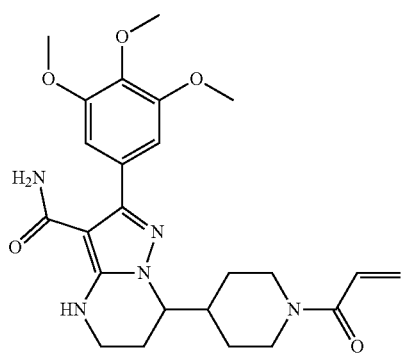 [SMILES: C=CC(=O)N1CCC(C2CCNc3c(C(N)=O)c(-c4cc(OC)c(OC)c(OC)c4)nn32)CC1]

Example A15 was synthesized from 3,4,5-trimethoxybenzoic acid following the procedures similar to those in Example A2 without the Suzuki reaction step. NaBH$_4$ was used in the reduction step. $^1$H NMR (400 MHz, DMSO-$d_6$) δ 6.79 (dd, J=16.8, 11.2 Hz, 1H), 6.76 (s, 2H), 6.73 (br s, 1H), 6.07 (dd, J=16.8, 2.4 Hz, 1H), 5.64 (dd, J=11.2, 2.4 Hz, 1H), 4.54-4.42 (m, 1H), 4.15-3.97 (m, 2H), 3.79 (s, 6H), 3.70 (s, 3H), 3.33-3.26 (m, 2H), 3.06-2.92 (m, 1H), 2.62-2.50 (m, 1H), 2.31-2.16 (m, 1H), 2.08-1.96 (m, 1H), 1.95-1.84 (m, 1H), 1.77-1.67 (m, 1H), 1.61-1.51 (m, 1H), 1.34-1.16 (m, 2H). MS (ESI) m/e [M+1]$^+$ 470.2.

Example A15: 7-(1-acryloylpiperidin-4-yl)-2-(3,5-dichloro-4-methoxyphenyl)-4,5,6,7-tetrahydropyrazolo[1,5-a]pyrimidine-3-carboxamide

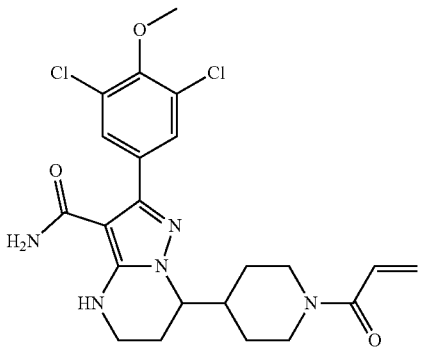 [SMILES: C=CC(=O)N1CCC(C2CCNc3c(C(N)=O)c(-c4cc(Cl)c(OC)c(Cl)c4)nn32)CC1]

Example A15 was synthesized from 3,5-dichloro-4-methoxybenzoic acid following the procedures similar to those in Example A2 without the Suzuki reaction step. NaBH$_4$ was used in the reduction step. $^1$H NMR (400 MHz, CDCl$_3$) δ 7.51 (s, 2H), 6.59 (dd, J=16.8, 10.6 Hz, 1H), 6.27 (dd, J=16.8, 1.8 Hz, 1H), 5.68 (dd, J=10.6, 1.8 Hz, 1H), 5.45 (br s, 2H), 4.88-4.64 (m, 1H), 4.14-4.04 (m, 2H), 3.94 (s, 3H), 3.50-3.40 (m, 2H), 3.17-2.92 (m, 1H), 2.75-2.26 (m, 2H), 2.25-2.00 (m, 2H), 1.85-1.73 (m, 1H), 1.72-1.56 (m, 1H), 1.54-1.41 (m, 1H), 1.40-1.24 (m, 1H). MS (ESI) m/e [M+1]$^+$ 478.1.

Example A16: 7-(1-acryloylpiperidin-4-yl)-2-(3,5-dibromo-4-methylphenyl)-4,5,6,7-tetrahydropyrazolo[1,5-a]pyrimidine-3-carboxamide

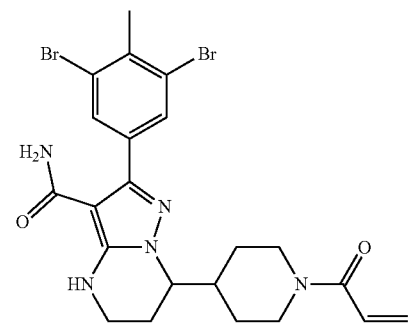 [SMILES: C=CC(=O)N1CCC(C2CCNc3c(C(N)=O)c(-c4cc(Br)c(C)c(Br)c4)nn32)CC1]

Example A16 was synthesized from 3,5-dibromo-4-methylbenzoic acid following the procedures similar to those in Example A1. $^1$H NMR (400 MHz, DMSO-$d_6$) δ 7.75 (s, 2H), 6.85-6.73 (m, 1H), 6.43 (br s, 2H), 6.07 (dd, J=16.8, 2.2 Hz, 1H), 5.64 (dd, J=10.4, 2.2 Hz, 1H), 4.54-4.41 (m, 1H), 4.15-3.93 (m, 2H), 3.33-3.23 (m, 2H), 3.07-2.92 (m, 1H), 2.64-2.54 (m, 1H), 2.53 (s, 3H), 2.34-2.17 (m, 1H), 2.08-1.96 (m, 1H), 1.95-1.83 (m, 1H), 1.75-1.63 (m, 1H), 1.60-1.47 (m, 1H), 1.35-1.10 (m, 2H). MS (ESI) m/e [M+1]$^+$ 552.0.

Example A17: 7-(1-acryloylpiperidin-4-yl)-2-(3,4,5-trichlorophenyl)-4,5,6,7-tetrahydropyrazolo[1,5-a]pyrimidine-3-carboxamide

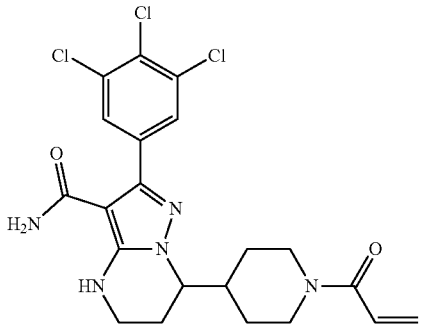

Example A17 was synthesized from 3,4,5-trichlorobenzoic acid following the procedures similar to those in Example A1. $^1$H NMR (400 MHz, DMSO-d$_6$) δ 7.73 (s, 2H), 6.87-6.73 (m, 1H), 6.62 (br s, 2H), 6.55 (br s, 1H), 6.08 (dd, J=16.6, 1.8 Hz, 1H), 5.64 (dd, J=10.4, 1.8 Hz, 1H), 4.55-4.41 (m, 1H), 4.7-3.96 (m, 2H), 3.35-3.20 (m, 2H), 3.08-2.92 (m, 1H), 2.69-2.50 (m, 1H), 2.34-2.17 (m, 1H), 2.10-1.96 (m, 1H), 1.96-1.82 (m, 1H), 1.77-1.64 (m, 1H), 1.62-1.49 (m, 1H), 1.36-1.12 (m, 2H). MS (ESI) m/e [M+1]$^+$ 482.1.

Example A18: 7-(1-acryloylpiperidin-4-yl)-2-(4-bromo-3,5-dichlorophenyl)-4,5,6,7-tetrahydropyrazolo[1,5-a]pyrimidine-3-carboxamide

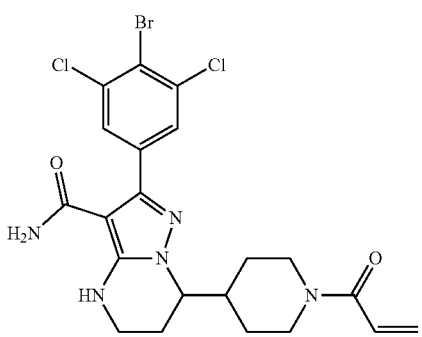 [SMILES: C=CC(=O)N1CCC(C2CCNc3c(C(N)=O)c(-c4cc(Cl)c(Cl)c(Cl)c4)nn32)CC1]

Example A18 was synthesized from 4-bromo-3,5-dichlorobenzoic acid following the procedures similar to those in Example A1. $^1$H NMR (400 MHz, DMSO-d$_6$) δ 7.70 (s, 2H), 6.96-6.73 (m, 1H), 6.62 (br s, 2H), 6.54 (br s, 1H), 6.07 (dd, J=16.8, 2.0 Hz, 1H), 5.64 (dd, J=10.4, 2.0 Hz, 1H), 4.55-4.42 (m, 1H), 4.16-3.98 (m, 2H), 3.33-3.23 (m, 2H), 3.07-2.92 (m, 1H), 2.69-2.52 (m, 1H), 2.35-2.16 (m, 1H), 2.10-1.96 (m, 1H), 1.96-1.83 (m, 1H), 1.77-1.64 (m, 1H), 1.62-1.47 (m, 1H), 1.35-1.10 (m, 2H). MS (ESI) m/e [M+1]$^+$ 526.4.

Example A19: 7-(1-acryloylpiperidin-4-yl)-2-(4-(furan-2-yl)-3,5-dimethoxyphenyl)-4,5,6,7-tetrahydropyrazolo[1,5-a]pyrimidine-3-carboxamide

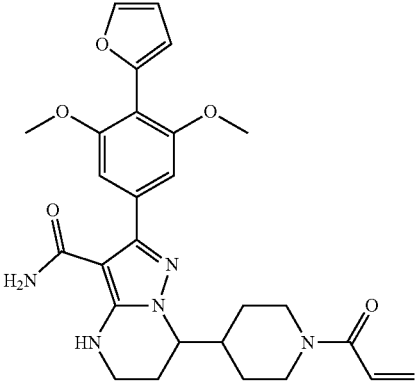 [SMILES: C=CC(=O)N1CCC(C2CCNc3c(C(N)=O)c(-c4cc(OC)c(-c5ccco5)c(OC)c4)nn32)CC1]

Example A19 was synthesized from tert-butyl 4-(2-(4-bromo-3,5-dimethoxyphenyl)-3-cyanopyrazolo[1,5-a]pyrimidin-7-yl)piperidine-1-carboxylate and furan-2-ylboronic acid following the procedures similar to those in Example A2. NaBH$_4$ was used in the reduction step. $^1$H NMR (400 MHz, DMSO-d$_6$) δ 7.70 (s, 1H), 6.87-6.84 (m, 1H), 6.85 (s, 2H), 6.80 (dd, J=16.8, 10.4 Hz, 1H), 6.56-6.53 (m, 1H), 6.50 (d, J=3.2 Hz, 1H), 6.07 (dd, J=16.8, 2.0 Hz, 1H), 5.64 (dd, J=10.4, 2.0 Hz, 1H), 4.92 (br s, 3H), 4.57-4.42 (m, 1H), 4.16-4.01 (m, 2H), 3.76 (s, 6H), 3.35-3.27 (m, 2H), 3.07-2.92 (m, 1H), 2.65-2.52 (m, 1H), 2.34-2.17 (m, 1H), 2.11-1.98 (m, 1H), 1.98-1.84 (m, 1H), 1.79-1.68 (m, 1H), 1.64-1.53 (m, 1H), 1.36-1.15 (m, 2H). MS (ESI) m/e [M+1]$^+$ 506.2.

Example A20: 7-(1-acryloylpiperidin-4-yl)-2-(4-bromo-3,5-dimethylphenyl)-4,5,6,7-tetrahydropyrazolo[1,5-a]pyrimidine-3-carboxamide

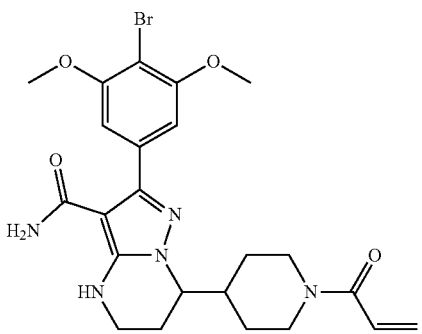 [SMILES: C=CC(=O)N1CCC(C2CCNc3c(C(N)=O)c(-c4cc(OC)c(Br)c(OC)c4)nn32)CC1]

Example A20 was synthesized from 4-bromo-3,5-dimethylbenzoic acid following the procedures similar to those in Example A1. $^1$H NMR (400 MHz, DMSO-d$_6$) δ 7.30 (s, 2H), 6.79 (dd, J=16.2, 10.6 Hz, 1H), 6.07 (dd, J=16.2, 1.6 Hz, 1H), 5.64 (dd, J=10.6, 1.6 Hz, 1H), 4.55-4.41 (m, 1H), 4.16-3.95 (m, 2H), 3.38-3.22 (m, 2H), 3.06-2.90 (m, 1H), 2.64-2.50 (m, 1H), 2.40 (s, 6H), 2.32-2.15 (m, 1H), 2.10-1.96 (m, 1H), 1.96-1.84 (m, 1H), 1.79-1.64 (m, 1H), 1.63-1.47 (m, 1H), 1.36-1.10 (m, 2H). MS (ESI) m/e [M+1]$^+$ 486.2.

Example A21: 7-(1-acryloylpiperidin-4-yl)-2-(3,5-dimethoxy-4-(1-methylcyclopropyl)phenyl)-4,5,6,7-tetrahydropyrazolo[1,5-a]pyrimidine-3-carboxamide

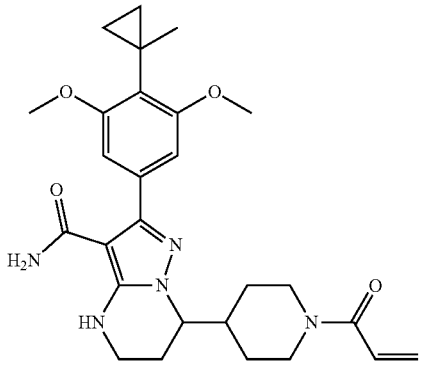 [SMILES: C=CC(=O)N1CCC(C2CCNc3c(C(N)=O)c(-c4cc(OC)c(C5(C)CC5)c(OC)c4)nn32)CC1]

Step 1: methyl 3,5-dimethoxy-4-(prop-1-en-2-yl)benzoate

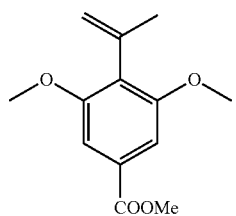

To a solution of methyl 4-bromo-3,5-dimethoxybenzoate (3.1 g, 11.3 mmol) in dioxane (50 mL) and sat. $K_2CO_3$ (50 mL) was added 4,4,5,5-tetramethyl-2-(prop-1-en-2-yl)-1,3,2-dioxaborolane (2.3 g, 13.5 mmol) and Pd(dppf)Cl$_2$ (830 mg, 1.13 mmol), the reaction atmosphere was exchanged with $N_2$ for three times, warmed to 90° C., stirred for about 16 h. Cooled to ambient temperature, the mixture was extracted with EA (30 mL×3), the combined organic phases were washed with sat. NaCl (20 mL), dried over anhydrous $Na_2SO_4$, filtered and concentrated to give the crude product (4.0 g) as a black oil which was purified by column chromatograph on silica gel (100-200 mesh, eluent: PE:EA=10:1) to afford the product as a white solid (2.6 g, 97.7%). MS (ESI, m/e) [M+1]$^+$ 237.1.

Step 2: methyl 3,5-dimethoxy-4-(1-methylcyclopropyl)benzoate

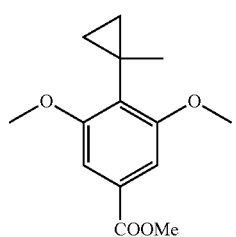

To a solution of methyl 3,5-dimethoxy-4-(prop-1-en-2-yl)benzoate (2.3 g, 9.75 mmol) in toluene (50 mL) was added CH$_2$I$_2$ (13.1 g, 48.7 mmol), the reaction was cooled to 0-5° C., stirred for about 15 min, ZnEt$_2$ (97.5 mL, 97.5 mmol, 1 M in n-hexane) was dropwisely added to the reaction, the reaction was slowly warmed to ambient temperature, stirred for about 16 h. CH$_2$I$_2$ (6.0 g, 22.4 mmol) was added to the reaction, the reaction was stirred at ambient temperature for about another 16 h. The reaction was concentrated under reduced pressure to remove solvent, the residue was portioned between EA (30 mL) and sat. NH$_4$Cl (30 mL), the aqueous phase was extracted EA (30 mL×3), the combined organic phases were washed with sat. NaCl (10 mL), dried over anhydrous Na$_2$SO$_4$, filtered, concentrated and purified by column chromatography of silica gel (200-300 mesh, eluent: PE:EA=10:1) to give the product as a yellow oil (1.8 g, 65.7%). MS (ESI, m/e) [M+1]$^+$ 251.1.

Step 3: 3,5-dimethoxy-4-(1-methylcyclopropyl)benzoic Acid

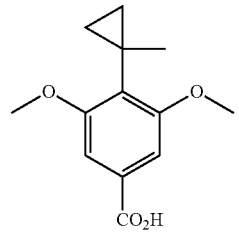

To a solution of methyl 3,5-dimethoxy-4-(1-methylcyclopropyl)benzoate (1.8 g, 7.20 mmol) in THF (30 mL) and H$_2$O (10 mL) was added LiOH.H$_2$O (1.52 g, 36.0 mmol), the reaction was warmed to 60° C. for about 6 h. The reaction was cooled to ambient temperature, concentrated under reduced pressure to remove THF, the residue was adjusted to the pH value of 2-3 with 3 N HCl, the aqueous phase was extracted with EA (30 mL×3), the combined organic phases were washed with sat. NaCl (20 mL), dried over anhydrous Na$_2$SO$_4$, filtered and concentrated to give the crude product as a yellow solid (1.5 g, 88.3%). MS (ESI, m/e) [M+1]$^+$ 237.1.

Step 4: 7-(1-acryloylpiperidin-4-yl)-2-(3,5-dimethoxy-4-(1-methylcyclopropyl)phenyl)-4,5,6,7-tetrahydropyrazolo[1,5-a]pyrimidine-3-carboxamide

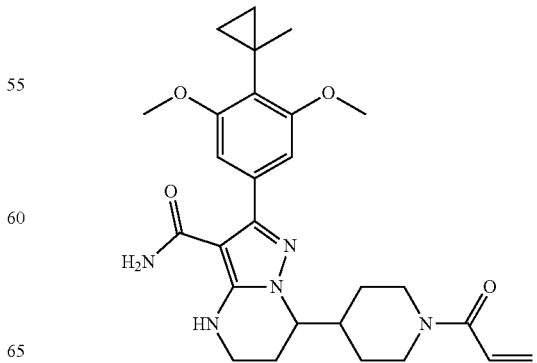

Example A21 was then synthesized from 3,5-dimethoxy-4-(1-methylcyclopropyl)benzoic acid following the procedures similar to those in Example A2 without the Suzuki reaction step. NaBH₄ was used in the reduction step. ¹H NMR (400 MHz, DMSO-d₆) δ 6.78 (dd, J=16.4, 10.4 Hz, 1H), 6.73 (br s, 1H), 6.69 (s, 2H), 6.06 (d, J=16.4 Hz, 1H), 5.63 (d, J=10.4 Hz, 1H), 4.53-4.42 (m, 1H), 4.15-3.97 (m, 2H), 3.79 (s, 6H), 3.32-3.25 (m, 2H), 3.05-2.90 (m, 1H), 2.64-2.50 (m, 1H), 2.34-2.15 (m, 1H), 2.10-1.96 (m, 1H), 1.96-1.83 (m, 1H), 1.77-1.66 (m, 1H), 1.61-1.50 (m, 1H), 1.35-1.19 (m, 1H), 1.18 (s, 3H), 0.68-0.59 (m, 4H). MS (ESI) m/e [M+1]⁺ 494.2.

Example 22: 7-(1-acryloylpiperidin-4-yl)-2-(4-chloro-3,5-dimethoxyphenyl)-4,5,6,7-tetrahydropyrazolo[1,5-a]pyrimidine-3-carboxamide

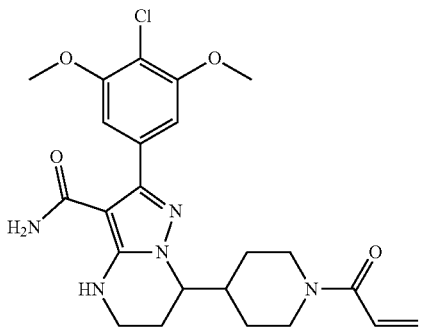

Step 1: 4-chloro-3,5-dimethoxyaniline

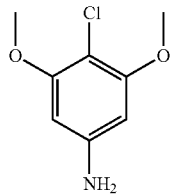

To a solution of 3,5-dimethoxyaniline (20.0 g, 130 mmol) in AcOH (50 mL) was added NCS (17.0 g, 130 mmol) in portions over 10 min. The mixture was stirred at RT for 16 h. The reaction was poured into DCM (200 mL) and H₂O (200 mL), the organic phase was washed with Sat. NaCl (100 mL), dried over anhydrous Na₂SO₄, filtered and evaporated to give a crude product which was purified by column chromatography on silica gel (PE:EA=12:1) to give desired product as a white solid (3.2 g, 13.1%). ¹H NMR (400 MHz, DMSO-d₆) δ 5.96 (s, 2H), 5.28 (s, 2H), 3.71 (s, 6H), MS (ESI, m/e) [M+1]⁺ 188.1.

Step 2: 2-chloro-5-iodo-1,3-dimethoxybenzene

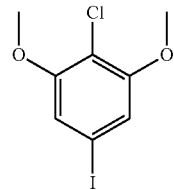

To a solution of 4-chloro-3,5-dimethoxyaniline (2.0 g, 10.70 mmol) in H₂O (30 mL) and con. H₂SO₄ (3.0 mL) was added the solution of NaNO₂ (1.11 g, 16.04 mmol) in water (6.0 mL) at 0-5° C., the reaction was stirred at 0-5° C. for about 30 min, the solution was added to the pre-warmed mixture of KI (7.11 g, 42.80 mmol) and I2 (1.36 g, 5.35 mmol) in H₂O (30 mL) and con. H₂SO₄ (3.0 mL) at 80° C., the resulting mixture was stirred at 80° C. for about 30 min. The reaction was allowed to cool to ambient temperature, sat. Na₂S₂O₃ (100 mL) was added to quench the reaction. The mixture was extracted with EA (30 mL×3), the combined organic phases were washed with sat. NaCl (20 mL), dried over anhydrous Na₂SO₄, filtered, concentrated and purified by column chromatography on silica gel (200-300 mesh, eluent: PE:EA=10:1) to give the product as a white solid (2.1 g, 65.9%). ¹H NMR (400 MHz, DMSO-d₆) δ 7.09 (s, 2H), 3.84 (s, 6H). MS (ESI) m/e [M+1]⁺ 298.9.

Step 3: 4-chloro-3,5-dimethoxybenzoic Acid

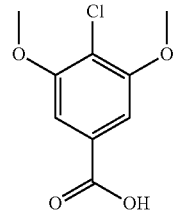

To a solution of 2-chloro-5-iodo-1,3-dimethoxybenzene (2.2 g, 7.38 mmol) in THF (50 mL) was added n-BuLi (5.5 mL, 8.86 mmol, 1.6 M in hexane) at −78° C., the reaction was stirred at −78° C. for about 30 min, CO₂ was bubbled into the reaction after drying over with anhydrous CaCl₂. The reaction was stirred at −78° C. for about 30 min, then warmed to ambient temperature, concentrated under reduced pressure to remove solvent, the residue was portioned between EA (50 mL) and water (20 mL), the aqueous phase was adjusted to the pH value of 2-3 with 3 N HCl and extracted with EA (30 mL×3). The combined organic phases were washed with sat. NaCl (15 mL), dried over anhydrous Na₂SO₄, filtered and concentrated to give the crude product as a pale yellow solid (2.0 g, 99.0%). MS (ESI) m/e [M+1]⁺ 217.1.

Step 4: 7-(1-acryloylpiperidin-4-yl)-2-(4-chloro-3,5-dimethoxyphenyl)-4,5,6,7-tetrahydropyrazolo[1,5-a]pyrimidine-3-carboxamide

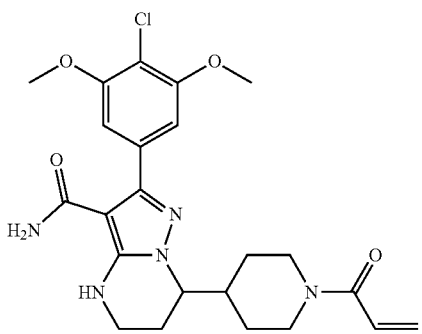

Example A22 was then synthesized from 4-chloro-3,5-dimethoxybenzoic acid following the procedures similar to those in Example A2 without the Suzuki reaction step. NaBH$_4$ was used in the reduction step. $^1$H NMR (400 MHz, DMSO-d$_6$) δ 6.87 (s, 2H), 6.79 (dd, J=16.4, 10.4 Hz, 1H), 6.73 (br s, 1H), 6.07 (dd, J=16.4, 2.0 Hz, 1H), 5.64 (d, J=10.4 Hz, 1H), 4.54-4.42 (m, 1H), 4.15-3.99 (m, 2H), 3.85 (s, 6H), 3.34-3.25 (m, 2H), 3.06-2.92 (m, 1H), 2.64-2.50 (m, 1H), 2.32-2.16 (m, 1H), 2.11-1.97 (m, 1H), 1.96-1.83 (m, 1H), 1.78-1.67 (m, 1H), 1.63-1.51 (m, 1H), 1.36-1.14 (m, 2H). MS (ESI) m/e [M+1]$^+$ 474.1.

Example A23: 7-(1-acryloylpiperidin-4-yl)-2-(4-bromo-3-chloro-5-methoxyphenyl)-4,5,6,7-tetrahydropyrazolo[1,5-a]pyrimidine-3-carboxamide

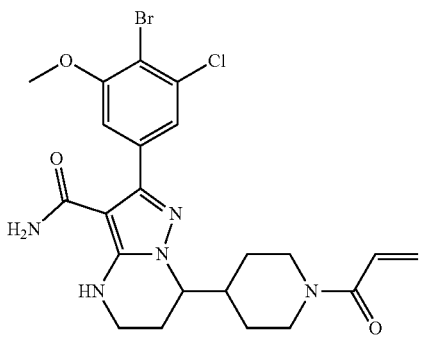 [SMILES: C=CC(=O)N1CCC(C2CCNc3c(C(N)=O)c(-c4cc(Cl)c(Br)c(OC)c4)nn32)CC1]

Step 1: Methyl 4-amino-3-chloro-5-methoxybenzoate

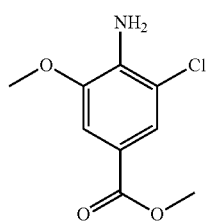

A mixture solution of methyl 4-amino-3-methoxybenzoate (9.06 g, 50 mmol) and NCS (7.34 g, 55 mmol) in CH$_3$CN (50 mL) was stirred at RT for 16 h. The mixture solution was washed with sat. NaHCO$_3$ (50 mL) and sat. NaCl (50 mL×2), dried over anhydrous Na$_2$SO$_4$, filtered and concentrated to give the crude product as a yellow solid (10.2 g, 94.4%). MS (ESI, m/e) [M+1]$^+$ 216.0.

Step 2: Methyl 4-bromo-3-chloro-5-methoxybenzoate

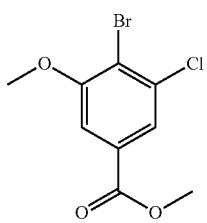

To a solution of methyl 4-amino-3-chloro-5-methoxybenzoate (2.16 g, 10.0 mmol) in CH$_3$CN (120 mL) and water (12 mL) was added CuBr$_2$ (3.04 g, 13.6 mmol) and tert-butyl nitrite (2.0 mL, 17.0 mmol). The resulting mixture solution was warmed to 60° C., stirred for about 1 h. The reaction mixture was cooled to ambient temperature and partitioned between EA (150 mL) and water (30 mL), the organic layer was washed with brine (60 mL), dried over anhydrous Na$_2$SO$_4$, filtered and concentrated to give a brown oil which was purified by column chromatography on silica gel (200-300 mesh, eluting: EA:PE=0-30%) to give the product as a white solid (5.3 g, 84.8%). MS (ESI, m/e) [M+1]$^+$ 278.9 and 280.9.

Step 2: 4-bromo-3-chloro-5-methoxybenzoic Acid

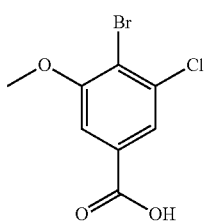

To a solution of Methyl 4-bromo-3-chloro-5-methoxybenzoate (2.5 g, 8.9 mmol) in EtOH (20 mL) was added NaOH (6.0 mL, 3 N), the reaction was stirred as reflux for about 2 h. The reaction was concentrated under reduced pressure to remove EtOH, the residue was adjusted to the pH value of 1-2 with 3 N HCl, the aqueous phase was extracted with EA (50 mL×3), the combined organic layers were dried over anhydrous Na$_2$SO$_4$, filtered and concentrated to give the crude product as white solid (2.16 g, 91.3%). MS (ESI, m/e) [M+1]$^+$ 264.9 and 266.9.

Step 3: 7-(1-acryloylpiperidin-4-yl)-2-(4-bromo-3-chloro-5-methoxyphenyl)-4,5,6,7-tetrahydropyrazolo[1,5-a]pyrimidine-3-carboxamide

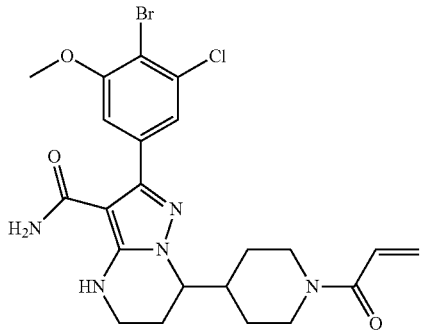

Example 23 was then synthesized from 4-bromo-3-chloro-5-methoxybenzoic acid following the procedures similar to those in Example A2 without the Suzuki reaction step. NaBH$_4$ was used in the reduction step. $^1$H NMR (400 MHz, DMSO-d$_6$) δ 7.31 (d, J=1.2 Hz, 1H), 7.19 (d, J=1.2 Hz, 1H), 6.85-6.74 (m, 1H), 6.36 (br s, 1H), 6.07 (dd, J=16.4, 1.8 Hz, 1H), 5.64 (dd, J=10.4, 1.8 Hz, 1H), 5.08 (br s, 2H), 4.54-4.42 (m, 1H), 4.16-3.98 (m, 2H), 3.89 (s, 3H), 3.34-3.24 (m, 2H), 3.06-2.92 (m, 1H), 2.64-2.51 (m, 1H), 2.35-2.16 (m, 1H), 2.10-1.96 (m, 1H), 1.96-1.82 (m, 1H), 1.78-1.65 (m, 1H), 1.62-1.50 (m, 1H), 1.37-1.12 (m, 2H). MS (ESI, m/e) [M+1]$^+$ 522.1 and 524.0.

Example A24: 7-(1-acryloylpiperidin-4-yl)-2-(3,5-dichloro-4-cyclopropylphenyl)-4,5,6,7-tetrahydropyrazolo[1,5-a]pyrimidine-3-carboxamide

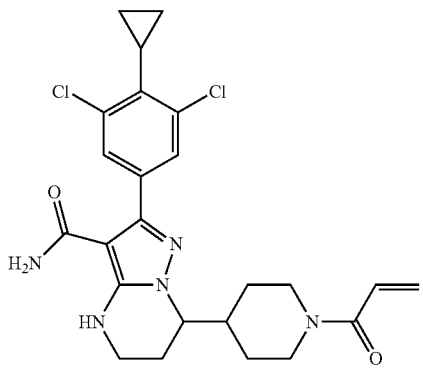 [SMILES: C=CC(=O)N1CCC(C2CCNc3c(C(N)=O)c(-c4cc(Cl)c(C5CC5)c(Cl)c4)nn32)CC1]

Example A24 was synthesized from tert-butyl 4-(2-(4-bromo-3,5-dichlorophenyl)-3-cyanopyrazolo[1,5-a]pyrimidin-7-yl)piperidine-1-carboxylate (one intermediate from A18) and cyclopropylboronic acid following the procedures similar to those in Example A2. NaBH$_4$ was used in the reduction step. $^1$H NMR (400 MHz, DMSO-d$_6$) δ 7.53 (s, 2H), 6.85-6.73 (m, 1H), 6.59 (br s, 1H), 6.07 (dd, J=16.6, 2.2 Hz, 1H), 5.64 (dd, J=10.6, 2.2 Hz, 1H), 4.54-4.42 (m, 1H), 4.15-3.97 (m, 2H), 3.33-3.26 (m, 2H), 3.06-2.92 (m, 1H), 2.64-2.50 (m, 1H), 2.34-2.16 (m, 1H), 2.08-1.96 (m, 1H), 1.95-1.84 (m, 1H), 1.84-1.79 (m, 1H), 1.75-1.64 (m, 1H), 1.59-1.48 (m, 1H), 1.32-1.18 (m, 2H), 1.19-1.10 (m, 2H), 0.76-0.69 (m, 2H). MS (ESI) m/e [M+1]$^+$ 488.1.

Example A25: 7-(1-acryloylpiperidin-4-yl)-2-(3,4,5-trimethylphenyl)-4,5,6,7-tetrahydropyrazolo[1,5-a]pyrimidine-3-carboxamide

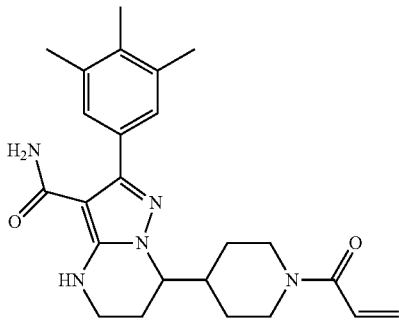 [SMILES: C=CC(=O)N1CCC(C2CCNc3c(C(N)=O)c(-c4cc(C)c(C)c(C)c4)nn32)CC1]

Step 1: 4-bromo-3,5-dimethylbenzoic Acid

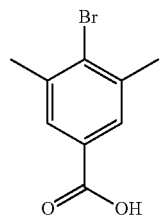

To a solution of NaOH (40 mL, 25% in H$_2$O) was added 4-bromo-3,5-dimethylbenzonitrile (2.0 g, 9.52 mmol), the reaction was warmed to 95° C., stirred for about 17 h. Cooled to ambient temperature, the solution was adjusted to the pH value of 1-2 with 12 N HCl, the solid was collected by filtration to give the crude product as a white solid (2.3 g, 99.0%). MS (ESI) m/e [M+1]$^+$ 228.3 and 230.3.

Step 2: 7-(1-acryloylpiperidin-4-yl)-2-(3,4,5-trimethylphenyl)-4,5,6,7-tetrahydropyrazolo[1,5-a]pyrimidine-3-carboxamide

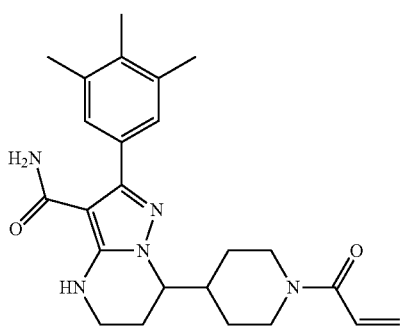 [SMILES: C=CC(=O)N1CCC(C2CCNc3c(C(N)=O)c(-c4cc(C)c(C)c(C)c4)nn32)CC1]

Example A25 was then synthesized from tert-butyl 4-(2-(4-bromo-3,5-dimethylphenyl)-3-cyanopyrazolo[1,5-a]pyrimidin-7-yl)piperidine-1-carboxylate (one intermediate from A20) and methylboronic acid following the procedures similar to those in Example A2. NaBH$_4$ was used in the reduction step. MsOH was used in the cyano hydrolysis step.

$^1$H NMR (400 MHz, CDCl$_3$) δ 7.15 (s, 2H), 6.66-6.49 (m, 2H), 6.25 (d, J=16.4 Hz, 1H), 5.66 (d, J=10.8 Hz, 1H), 5.55-5.00 (m, 2H), 4.84-4.67 (m, 1H), 4.19-3.96 (m, 2H), 3.47-3.38 (m, 2H), 3.14-2.94 (m, 1H), 2.65-2.50 (m, 1H), 2.31 (s, 6H), 2.20 (s, 3H), 2.12-2.02 (m, 1H), 1.90-1.75 (m, 2H), 1.73-1.55 (m, 1H), 1.54-1.40 (m, 1H), 1.35-1.22 (m, 2H). MS (ESI) m/e [M+1]$^+$ 422.2.

Example A26: 7-(1-acryloylpiperidin-4-yl)-2-(4-bromo-3-chloro-5-(trifluoromethoxy)phenyl)-4,5,6,7-tetrahydropyrazolo[1,5-a]pyrimidine-3-carboxamide

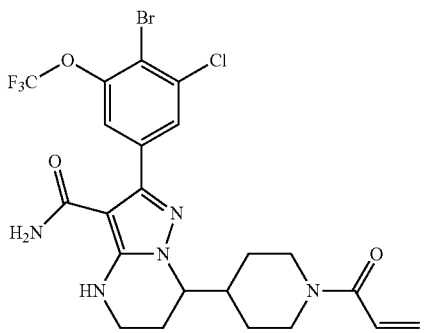 [SMILES: C=CC(=O)N1CCC(C2CCNc3c(C(N)=O)c(-c4cc(Cl)c(Br)c(OC(F)(F)F)c4)nn32)CC1]

Step 1: methyl 4-amino-3-(trifluoromethoxy)benzoate

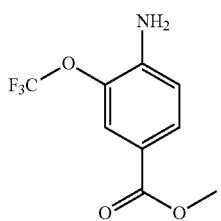 [SMILES: COC(=O)c1ccc(N)c(OC(F)(F)F)c1]

To a solution of 4-amino-3-(trifluoromethoxy)benzoic acid (10.0 g, 45.3 mmol) in MeOH (120 mL) was added SOCl$_2$ (10 mL) for dropwise, the reaction was stirred at 60° C. for about 16 h. The reaction was cooled to ambient temperature, concentrated under reduced pressure to remove solvent, the residue was partitioned between EA (80 mL) and H$_2$O (20 mL), the organic phase was washed with sat. NaHCO$_3$ (20 mL×2) and brine (20 mL), dried over anhydrous Na$_2$SO$_4$, filtered and concentrated to give the crude product as a brown solid (9.8 g, 92.2%). MS (ESI) m/e [M+1]$^+$ 236.0.

Step 2: methyl 4-amino-3-chloro-5-(trifluoromethoxy)benzoate

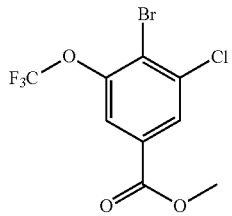 [SMILES: COC(=O)c1cc(Cl)c(Br)c(OC(F)(F)F)c1]

To a solution of methyl 4-amino-3-(trifluoromethoxy)benzoate (4.7 g, 20.0 mmol) in CH$_3$CN (100 mL) was added DMAC (10 mL) and NCS (2.94 g, 22.0 mmol), the reaction was warmed to 70° C., stirred for about 2 h. The reaction was cooled to ambient temperature, concentrated under reduced pressure to remove CH$_3$CN, the residue was diluted with EA (80 mL), the solution was washed with H$_2$O (20 mL×5) and brine (20 mL), dried over anhydrous Na$_2$SO$_4$, filtered, concentrated and purified by column chromatography on silica gel (200-300 mesh, eluent PE:EA=4:1) to give the product as a yellow solid (4.8 g, 89.0%). MS (ESI) m/e [M+1]$^+$ 270.0.

Step 3: methyl 4-bromo-3-chloro-5-(trifluoromethoxy)benzoate

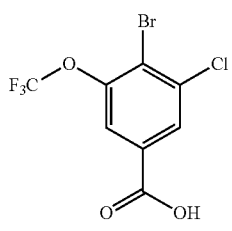 [SMILES: O=C(O)c1cc(Cl)c(Br)c(OC(F)(F)F)c1]

To a solution of methyl 4-amino-3-chloro-5-(trifluoromethoxy)benzoate (2.4 g, 8.92 mmol) in CH$_3$CN (50 mL) and H$_2$O (5 mL) was added CuBr$_2$ (2.79 g, 12.49 mmol), then tert-butyl nitrite (1.56 g, 15.2 mmol) was added to the reaction for dropwise at RT, the reaction was warmed to 60° C., stirred for about 2 h. The reaction was cooled to RT, concentrated under reduced pressure to remove most of the solvent, the residue mixture was extracted with DCM (20 mL×2), the combined organic layers were concentrated and purified by column chromatography on silica gel (100-200 mesh, eluent: EA:DCM=1:4) to give the product as yellow solid (2.5 g, 84.5%).

Step 4: 4-bromo-3-chloro-5-(trifluoromethoxy)benzoic Acid

To a solution of methyl 4-bromo-3-chloro-5-(trifluoromethoxy)benzoate (2.5 g, 8.9 mmol) in MeOH (30 mL) and THF (20 mL) was added NaOH (20 mL, 3 N in water), the reaction was stirred at RT for about 1 h. The reaction was concentrated under reduced pressure to remove organic solvent, the resulting solution was cooled to 0-5° C., adjusted to the pH value of 1-2 with 3N HCl, the solid was collected by filtration to give the product as a light pink solid (1.6 g, 62.6%. MS (ESI) m/e [M−1]⁻ 316.8 and 318.8.

Step 5: 7-(1-acryloylpiperidin-4-yl)-2-(4-bromo-3-chloro-5-(trifluoromethoxy)phenyl)-4,5,6,7-tetrahydropyrazolo[1,5-a]pyrimidine-3-carboxamide

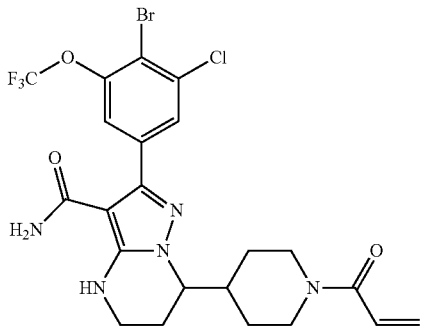 [SMILES: C=CC(=O)N1CCC(C2CCNc3c(C(N)=O)c(-c4cc(Cl)c(Br)c(OC(F)(F)F)c4)nn32)CC1]

Example A26 was then synthesized from 4-bromo-3-chloro-5-(trifluoromethoxy)benzoic acid following the procedures similar to those in Example A1. ¹H NMR (400 MHz, DMSO-d₆) δ 7.81 (d, J=1.6 Hz, 1H), 7.62 (s, 1H), 6.84-6.74 (m, 1H), 6.60 (br s, 3H), 6.07 (dd, J=16.7, 2.2 Hz, 1H), 5.64 (dd, J=10.5, 2.2 Hz, 1H), 4.55-4.40 (m, 1H), 4.15-3.97 (m, 2H), 3.30-3.25 (m, 2H), 3.06-2.92 (m, 1H), 2.68-2.52 (m, 1H), 2.34-2.16 (m, 1H), 2.10-1.97 (m, 1H), 1.97-1.83 (m, 1H), 1.76-1.64 (m, 1H), 1.62-1.50 (m, 1H), 1.35-1.15 (m, 2H). MS (ESI) m/e [M+1]⁺ 576.1 and 578.1.

Example A27: 7-(1-acryloylpiperidin-4-yl)-2-(3,5-dimethoxy-4-(1H-pyrazol-3-yl)phenyl)-4,5,6,7-tetrahydropyrazolo[1,5-a]pyrimidine-3-carboxamide

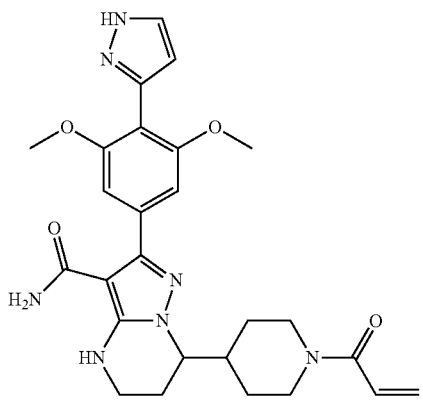 [SMILES: C=CC(=O)N1CCC(C2CCNc3c(C(N)=O)c(-c4cc(OC)c(-c5cc[nH]n5)c(OC)c4)nn32)CC1]

Example A27 was synthesized from tert-butyl 4-(2-(4-bromo-3,5-dimethoxyphenyl)-3-cyanopyrazolo[1,5-a]pyrimidin-7-yl)piperidine-1-carboxylate and 1-(tetrahydro-2H-pyran-2-yl)-5-(4,4,5,5-tetramethyl-1,3,2-dioxaborolan-2-yl)-1H-pyrazole following the procedures similar to those in Example A2. NaBH₄ was used in the reduction step. MsOH was used in the cyano hydrolysis step. ¹H NMR (400 MHz, DMSO-d₆) δ 7.53 (s, 1H), 6.87 (s, 2H), 6.80 (dd, J=17.0, 10.4 Hz, 1H), 6.75 (br s, 1H), 6.52 (s, 1H), 6.07 (dd, J=17.0, 2.4 Hz, 1H), 5.64 (d, J=10.4 Hz, 1H), 4.54-4.43 (m, 1H), 4.18-4.00 (m, 2H), 3.80 (s, 6H), 3.35-3.20 (m, 2H), 3.10-2.91 (m, 1H), 2.67-2.53 (m, 1H), 2.35-2.17 (m, 1H), 2.12-1.98 (m, 1H), 1.98-1.84 (m, 1H), 1.80-1.69 (m, 1H), 1.64-1.53 (m, 1H), 1.38-1.26 (m, 2H). MS (ESI) m/e [M+1]⁺ 506.2.

Example A28: 7-(1-acryloylpiperidin-4-yl)-2-(3,5-dimethoxy-4-(thiophen-3-yl)phenyl)-4,5,6,7-tetrahydropyrazolo[1,5-a]pyrimidine-3-carboxamide

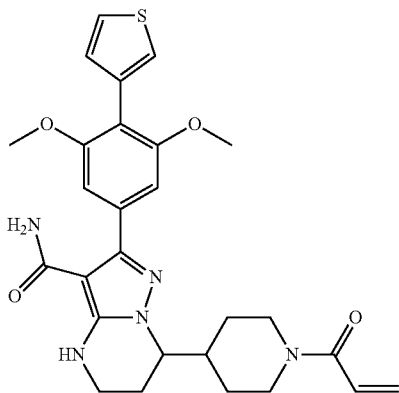 [SMILES: C=CC(=O)N1CCC(C2CCNc3c(C(N)=O)c(-c4cc(OC)c(-c5ccsc5)c(OC)c4)nn32)CC1]

Example A28 was synthesized from tert-butyl 4-(2-(4-bromo-3,5-dimethoxyphenyl)-3-cyanopyrazolo[1,5-a]pyrimidin-7-yl)piperidine-1-carboxylate and thiophen-3-ylboronic acid following the procedures similar to those in Example A2. NaBH₄ was used in the reduction step. ¹H NMR (400 MHz, DMSO-d₆) δ 7.51-7.44 (m, 2H), 7.19 (dd, J=4.8, 1.2 Hz, 1H), 6.84 (s, 2H), 6.83-6.73 (m, 2H), 6.07 (dd, J=16.8, 2.4 Hz, 1H), 5.64 (d, J=11.6 Hz, 1H), 4.57-4.42 (m, 1H), 4.18-4.01 (m, 2H), 3.73 (s, 6H), 3.33-3.27 (m, 2H), 3.08-2.92 (m, 1H), 2.65-2.52 (m, 1H), 2.35-2.17 (m, 1H), 2.10-1.86 (m, 2H), 1.82-1.68 (m, 1H), 1.64-1.53 (m, 1H), 1.36-1.25 (m, 2H). MS (ESI) m/e [M+1]⁺ 522.2.

Example A29: 7-(1-acryloylpiperidin-4-yl)-2-(4-cyclopropyl-3,5-dimethylphenyl)-4,5,6,7-tetrahydropyrazolo[1,5-a]pyrimidine-3-carboxamide

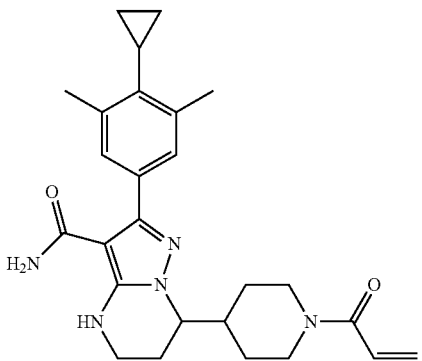 [SMILES: C=CC(=O)N1CCC(C2CCNc3c(C(N)=O)c(-c4cc(C)c(C5CC5)c(C)c4)nn32)CC1]

Example 29 was synthesized from tert-butyl 4-(2-(4-bromo-3,5-dimethylphenyl)-3-cyanopyrazolo[1,5-a]pyrimidin-7-yl)piperidine-1-carboxylate (one intermediate from A20) and cyclopropylboronic acid following the procedures similar to those in Example A2. NaBH$_4$ was used in the reduction step. MsOH was used in the cyano hydrolysis step. $^1$H NMR (400 MHz, CDCl$_3$) δ 7.22-7.10 (m, 2H), 6.56 (dd, J=16.8, 10.8 Hz, 1H), 6.38-6.20 (m, 2H), 5.93-5.59 (m, 3H), 4.84-4.68 (m, 1H), 4.20-3.96 (m, 2H), 3.60-3.32 (m, 2H), 3.14-2.94 (m, 1H), 2.90-2.42 (m, 3H), 2.35-2.20 (m, 6H), 2.17-2.00 (m, 2H), 1.93 (d, J=6.6 Hz, 2H), 1.87-1.57 (m, 2H), 1.46 (d, J=6.6 Hz, 2H), 1.38-1.23 (m, 2H). MS (ESI) m/e [M+1]$^+$ 448.2.

Example A30: 7-(1-acryloylpiperidin-4-yl)-2-(3,5-dimethylphenyl)-4,5,6,7-tetrahydropyrazolo[1,5-a]pyrimidine-3-carboxamide

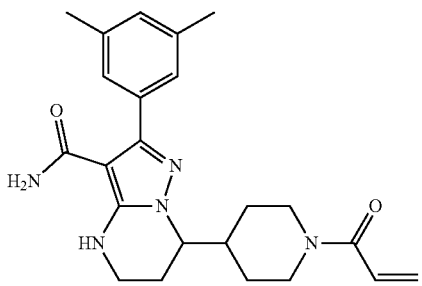 [SMILES: C=CC(=O)N1CCC(C2CCNc3c(C(N)=O)c(-c4cc(C)cc(C)c4)nn32)CC1]

Example A30 is a byproduct when preparing Example A29. $^1$H NMR (400 MHz, CDCl$_3$) δ 8.46 (br s, 2H), 7.20-7.00 (s, 4H), 6.56 (dd, J=16.8, 10.8 Hz, 1H), 6.26 (d, J=16.8 Hz, 1H), 5.83-5.58 (m, 2H), 4.88-4.65 (m, 1H), 4.22-3.96 (m, 2H), 3.56-3.38 (m, 2H), 3.14-2.99 (m, 1H), 2.74-2.58 (m, 1H), 2.36 (s, 6H), 2.35-2.24 (m, 1H), 2.22-1.99 (m, 2H), 1.91-1.59 (m, 2H), 1.57-1.42 (m, 1H), 1.41-1.22 (m, 1H). MS (ESI) m/e [M+1]$^+$ 408.2.

Example A31: 7-(1-acryloylpiperidin-4-yl)-2-(4-(3,5-dimethylisoxazol-4-yl)-3,5-dimethoxyphenyl)-4,5,6,7-tetrahydropyrazolo[1,5-a]pyrimidine-3-carboxamide

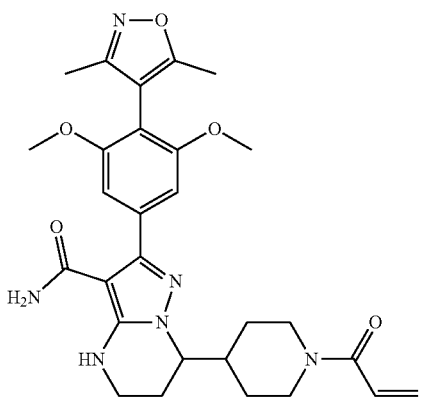 [SMILES: C=CC(=O)N1CCC(C2CCNc3c(C(N)=O)c(-c4cc(OC)c(-c5c(C)noc5C)c(OC)c4)nn32)CC1]

Example A31 was synthesized from tert-butyl 4-(2-(4-bromo-3,5-dimethoxyphenyl)-3-cyanopyrazolo[1,5-a]pyrimidin-7-yl)piperidine-1-carboxylate and (3,5-dimethylisoxazol-4-yl)boronic acid following the procedures similar to those in Example A2. NaBH$_4$ was used in the reduction step. $^1$H NMR (400 MHz, CDCl$_3$) δ 6.80 (s, 2H), 6.69 (br s, 1H), 6.57 (dd, J=16.8, 10.6 Hz, 1H), 6.27 (d, J=16.8 Hz, 1H), 5.68 (d, J=10.6 Hz, 1H), 5.35 (br s, 2H), 4.87-4.70 (m, 1H), 4.21-4.02 (m, 2H), 3.80 (s, 6H), 3.55-3.40 (m, 2H), 3.17-2.98 (m, 1H), 2.72-2.56 (m, 1H), 2.56-2.33 (m, 1H), 2.22 (s, 3H), 2.20-2.02 (m, 1H), 2.10 (s, 3H), 1.90-1.60 (m, 2H), 1.57-1.45 (m, 1H), 1.44-1.32 (m, 1H), 1.32-1.20 (m, 1H). MS (ESI) m/e [M+1]$^+$ 535.2.

Example A32: 7-(1-acryloylpiperidin-4-yl)-2-(3,5-dimethoxy-4-(tetrahydro-2H-pyran-4-yl)phenyl)-4,5,6,7-tetrahydropyrazolo[1,5-a]pyrimidine-3-carboxamide

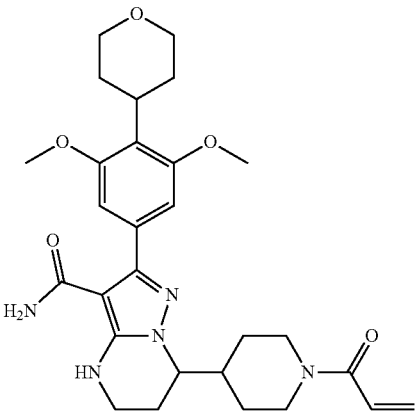 [SMILES: C=CC(=O)N1CCC(C2CCNc3c(C(N)=O)c(-c4cc(OC)c(C5CCOCC5)c(OC)c4)nn32)CC1]

Step 1: tert-butyl 4-(3-carbamoyl-2-(3,5-dimethoxy-4-(tetrahydro-2H-pyran-4-yl)phenyl)-4,5,6,7-tetrahydropyrazolo[1,5-a]pyrimidin-7-yl)piperidine-1-carboxylate

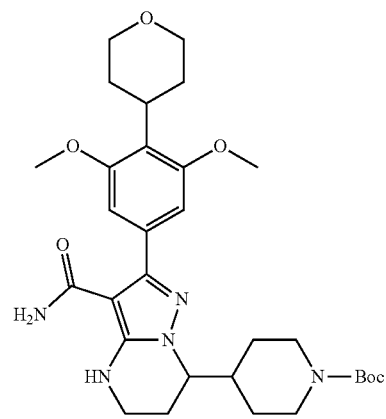 [SMILES: COc1cc(-c2nn3c(c2C(N)=O)NCCC3C2CCN(C(=O)OC(C)(C)C)CC2)cc(OC)c1C1CCOCC1]

To a solution of tert-butyl 4-(3-carbamoyl-2-(4-(3,6-dihydro-2H-pyran-4-yl)-3,5-dimethoxyphenyl)-4,5,6,7-tetrahydropyrazolo[1,5-a]pyrimidin-7-yl)piperidine-1-carboxylate (100 mg, 0.18 mmol, prepared from tert-butyl 4-(2-(4-bromo-3,5-dimethoxyphenyl)-3-cyanopyrazolo[1,5-a]pyrimidin-7-yl)piperidine-1-carboxylate and 2-(3,6-dihydro-2H-pyran-4-yl)-4,4,5,5-tetramethyl-1,3,2- dioxaborolane following the procedures similar to those in Example A2. NaBH₄ was used in the reduction step) in MeOH (10 mL) was added Pd(OH)₂/C (50 mg), the mixture was stirred RT under H₂ atmosphere for about 3 h. The reaction was then heated to 50° C., stirred for about 50 h. The solid was filtered and the filtrate was concentrated under reduced pressure to give the crude product as a brown solid (100 mg, 99.0%). MS (ESI) m/e [M+1]⁺ 570.2.

Example A32 was then synthesized from tert-butyl 4-(3-carbamoyl-2-(3,5-dimethoxy-4-(tetrahydro-2H-pyran-4-yl)phenyl)-4,5,6,7-tetrahydropyrazolo[1,5-a]pyrimidin-7-yl)piperidine-1-carboxylate following the procedures similar to those in Example A2. ¹H NMR (400 MHz, CDCl₃) δ 6.68 (s, 2H), 6.65 (br s, 1H), 6.56 (dd, J=16.6, 10.6 Hz, 1H), 6.25 (d, J=16.6 Hz, 1H), 5.66 (d, J=10.6 Hz, 1H), 5.34 (br s, 2H), 4.85-4.65 (m, 1H), 4.20-3.97 (m, 4H), 3.82 (s, 6H), 3.60-3.33 (m, 5H), 3.14-2.95 (m, 1H), 2.67-2.30 (m, 3H), 2.19-2.00 (m, 2H), 1.97-1.75 (m, 2H), 1.73-1.59 (m, 1H), 1.53-1.20 (m, 4H). MS (ESI) m/e [M+1]⁺ 524.2.

Example A33: 7-(1-acryloylpiperidin-4-yl)-2-(4-cyclopropyl-3-ethoxy-5-methoxyphenyl)-4,5,6,7-tetrahydropyrazolo[1,5-a]pyrimidine-3-carboxamide

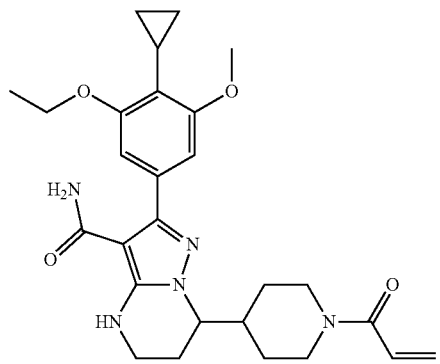 [SMILES: C=CC(=O)N1CCC(C2CCNc3c(C(N)=O)c(-c4cc(OC)c(C5CC5)c(OCC)c4)nn32)CC1]

Step 1: methyl 4-bromo-3,5-dihydroxybenzoate

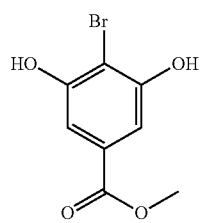

To a solution of 4-bromo-3,5-dihydroxybenzoic acid (50.0 g, 214.6 mmol) in methanol (500 mL) was added SOCl₂ (20 mL), the reaction mixture was stirred at 60° C. for about 3 h. The reaction mixture was concentrated under reduced pressure. The residue was poured into methanol (100 mL) and H₂O (100 mL), the solution was stirred at RT for about 1 h, the precipitate was filtered, collected and dried in vacuum to afford the product as a white solid (55.0 g, 99.0%). MS (ESI, m/e) [M+1]⁺ 246.9 and 248.9.

Step 2: methyl 4-bromo-3-ethoxy-5-hydroxybenzoate

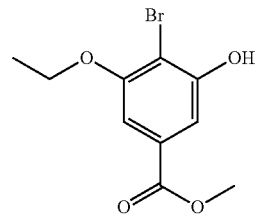

To a solution of methyl 4-bromo-3,5-dihydroxybenzoate (10.0 g, 40.5 mmol) in DMF (110 mL) was added K₂CO₃ (11.2 g, 81.0 mmol) and iodoethane (3.55 mL, 44.5 mmol), the reaction mixture was stirred at ambient temperature for about 16 h. EA (300 mL) was added, the mixture was washed with H₂O (100 mL×2) and sat. NaCl (100 mL), concentrated and purified by column chromatograph on silica gel (200-300 mesh, eluent: PE:EA=10:1) to afford the product as a white solid (2.3 g, 20.6%). MS (ESI, m/e) [M+1]⁺ 275.0 and 277.0.

Step 3: methyl 4-bromo-3-ethoxy-5-methoxybenzoate

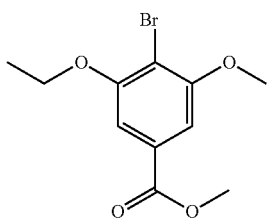 [SMILES: CCOc1cc(C(=O)OC)cc(OC)c1Br]

To a solution of methyl 4-bromo-3-ethoxy-5-hydroxybenzoate (2.3 g, 8.36 mmol) in DMF (40 mL) was added K₂CO₃ (2.3 g, 16.73 mmol) and iodomethane (1.78 g, 12.55 mmol), the reaction was stirred at ambient temperature for about 60 h. EA (50 mL) was added, the mixture was washed with H₂O (30 mL×3) and sat. NaCl (20 mL), dried over anhydrous Na₂SO₄, filtered and concentrated to afford the product as a white solid (2.4 g, 96.0%).

Step 4: methyl 4-cyclopropyl-3-ethoxy-5-methoxybenzoate

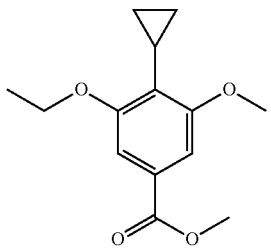 [SMILES: CCOc1cc(C(=O)OC)cc(OC)c1C1CC1]

To a solution of methyl 4-bromo-3-ethoxy-5-methoxybenzoate (2.3 g, 7.96 mmol) in 1,4-dioxane (30 mL) and H₂O (10 mL) was added cyclopropylboronic acid (2.15 g, 23.88 mmol), K₂CO₃ (4.4 g, 31.83 mmol) and Pd(dppf)Cl₂ (1.16 g, 1.59 mmol), the reaction atmosphere was exchanged with N₂ for three times, warmed to 80° C. and stirred for about 20 h. Cooled to ambient temperature, the mixture was filtered through a Celite pad and the filtrate was concentrated under reduced pressure to remove 1,4-dioxane. The resulting mixture was extracted with EA (30 mL×2). The combined organic phases were washed with H₂O (20 mL), concentrated and purified by column chromatograph on silica gel (100-200 mesh, eluent: PE:EA=2:1) to afford the product as a white solid (1.8 g, 90.5%). MS (ESI, m/e) [M+1]⁺ 251.1.

Step 5: 4-cyclopropyl-3-ethoxy-5-methoxybenzoic Acid

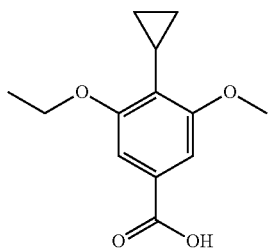 [SMILES: CCOc1cc(C(=O)O)cc(OC)c1C1CC1]

To a solution of methyl 4-cyclopropyl-3-ethoxy-5-methoxybenzoate (1.8 g, 7.20 mmol) in methanol (20 mL) was added 3N NaOH (10 mL), the mixture was stirred at ambient temperature for about 3 h. The mixture was concentrated under reduced pressure to remove methanol. The residue was adjusted to the pH value of 2-3 with 3 N HCl. The precipitate was collected by filtration and dried in vacuum to give the product as a white solid (1.0 g, 58.6%). MS (ESI, m/e) [M+1]⁺ 237.1.

Step 6: 7-(1-acryloylpiperidin-4-yl)-2-(4-cyclopropyl-3-ethoxy-5-methoxyphenyl)-4,5,6,7-tetrahydropyrazolo[1,5-a]pyrimidine-3-carboxamide

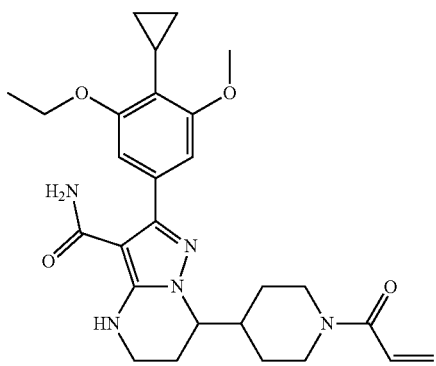 [SMILES: C=CC(=O)N1CCC(C2CCNc3c(C(N)=O)c(-c4cc(OC)c(C5CC5)c(OCC)c4)nn32)CC1]

Example A33 was then synthesized from 4-cyclopropyl-3-ethoxy-5-methoxybenzoic acid following the procedures similar to those in Example A2 without the Suzuki reaction step. NaBH₄ was used in the reduction step. ¹H NMR (400 MHz, DMSO-d₆) δ 6.78 (dd, J=16.8, 10.4 Hz, 1H), 6.72 (br s, 1H), 6.66 (s, 1H), 6.65 (s, 1H), 6.06 (dd, J=2.4, 16.8 Hz, 1H), 5.63 (dd, J=2.4, 10.4 Hz, 1H), 4.53-4.42 (m, 1H), 4.14-3.91 (m, 4H), 3.75 (s, 3H), 3.33-3.25 (m, 2H), 3.06-2.91 (m, 1H), 2.64-2.50 (m, 1H), 2.31-2.15 (m, 1H), 2.09-1.96 (m, 1H), 1.96-1.83 (m, 2H), 1.78-1.66 (m, 1H), 1.62-1.50 (m, 1H), 1.32 (t, J=6.8 Hz, 3H), 1.30-1.14 (m, 2H), 1.07-1.01 (m, 2H), 0.79-0.72 (m, 2H). MS (ESI) m/e [M+1]⁺ 494.2.

Example A34: 7-(1-acryloylpiperidin-4-yl)-2-(3-methoxy-4,5-dimethylphenyl)-4,5,6,7-tetrahydropyrazolo[1,5-a]pyrimidine-3-carboxamide

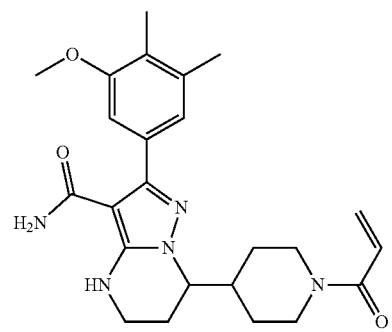 [SMILES: C=CC(=O)N1CCC(C2CCNc3c(C(N)=O)c(-c4cc(C)c(C)c(OC)c4)nn32)CC1]

Step 1: Methyl 3-bromo-5-methoxy-4-(((trifluoromethyl)sulfonyl)oxy)benzoate

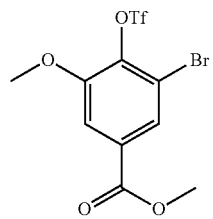

A mixture solution of methyl 3-bromo-4-hydroxy-5-methoxybenzoate (13.0 g, 50 mmol), 1,1,1-trifluoro-N-(4-methoxyphenyl)-N-(((trifluoromethyl)sulfonyl)methane sulfonamide (22 g, 60 mmol) and TEA (10.0 g, 100 mmol) in DCM (200 mL) was stirred at RT for 16 h. Then the mixture solution was concentrated and the residue was purified by column chromatography on silica gel (eluent: EA:PE=1: 10-1:5) to give the product as a white solid (18.7 g, 95.5%). MS (ESI, m/e) [M+1]⁺ 392.9 and 394.9.

Step 2: Methyl 3-methoxy-4,5-dimethylbenzoate

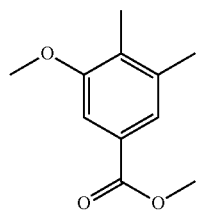

Under a nitrogen atmosphere, a mixture solution of methyl 3-bromo-5-methoxy-4-(((trifluoromethyl)sulfonyl)

oxy)benzoate (3.93 g, 10 mmol), methylboronic acid (3.0 g, 50 mmol), Pd(dppf)Cl₂ (731 mg, 1 mmol) and Cs₂CO₃ (6.5 g, 20 mmol) in 1,4-dioxane (100 mL) was stirred at 90° C. for 16 h, then the reaction mixture was concentrated and the residue was purified by column chromatography on silica gel (eluent: EA:PE=0-30%) to give the product as a white solid (1.5 g, 77.3%). MS (ESI, m/e) [M+1]⁺ 195.1.

Step 3: 3-methoxy-4,5-dimethylbenzoic Acid

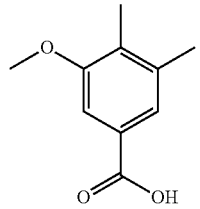

A mixture solution of methyl 3-methoxy-4,5-dimethylbenzoate (2.7 g, 13.9 mmol), and NaOH (3 N, 10 mL) in ethanol (30 mL) was stirred at 80° C. for 2 h. Then the ethanol was removed in vacuum, the residue was acidified by 2 N HCl, extracted with EA (20 mL×3), the combined organic layers were dried over Na₂SO₄, filtered and concentrated to give the product as a white solid (1.78 g, 70.4%). MS (ESI, m/e) [M+1]⁺ 181.1.

Step 4: 7-(1-acryloylpiperidin-4-yl)-2-(3-methoxy-4, 5-dimethylphenyl)-4,5,6,7-tetrahydropyrazolo[1,5-a] pyrimidine-3-carboxamide

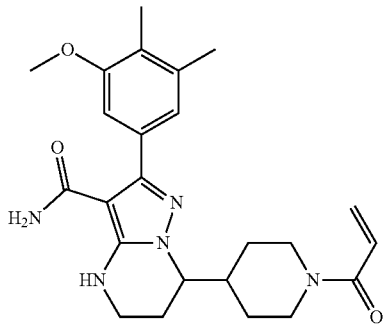 [SMILES: C=CC(=O)N1CCC(C2CCNc3c(C(N)=O)c(-c4cc(C)c(C)c(OC)c4)nn32)CC1]

Example A34 was then synthesized from 3-methoxy-4,5-dimethylbenzoic acid following the procedures similar to those in Example A1. Pd/C was used in the reduction step. ¹H NMR (400 MHz, CDCl₃) δ 6.91 (s, 1H), 6.81 (s, 1H), 6.56 (dd, J=16.0, 10.0 Hz, 1H), 6.26 (d, J=16.0 Hz, 1H), 5.71 (d, J=10.0 Hz, 1H), 4.86-4.68 (m, 1H), 4.22-3.99 (m, 2H), 3.84 (s, 3H), 3.54-3.41 (m, 2H), 3.16-2.98 (m, 1H), 2.74-2.58 (m, 1H), 2.56-2.34 (m, 1H), 2.30 (s, 3H), 2.17 (s, 3H), 2.16-2.02 (m, 2H), 1.90-1.75 (m, 1H), 1.74-1.59 (m, 1H), 1.57-1.43 (m, 1H), 1.42-1.28 (m, 1H). MS (ESI, m/e) [M+1]⁺ 438.2.

Example A35: 7-(1-acryloylpiperidin-4-yl)-2-(3-chloro-5-methoxy-4-methylphenyl)-4,5,6,7-tetrahydropyrazolo[1,5-a]pyrimidine-3-carboxamide

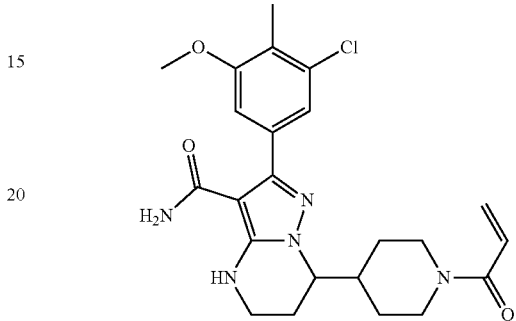

Step 1: tert-butyl 4-(3-carbamoyl-2-(3-chloro-5-methoxy-4-methylphenyl)-4,5,6,7-tetrahydropyrazolo[1,5-a]pyrimidin-7-yl)piperidine-1-carboxylate

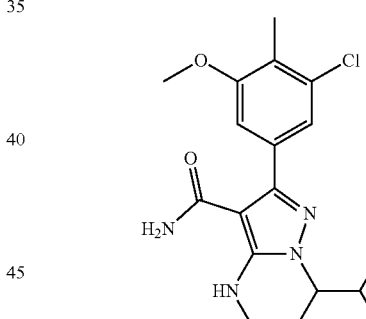

A mixture solution of tert-butyl 4-(2-(4-bromo-3-chloro-5-methoxyphenyl)-3-carbamoyl-4,5,6,7-tetrahydropyrazolo[1,5-a]pyrimidin-7-yl)piperidine-1-carboxylate (568 mg, 1.0 mmol, intermediate from Example A23), methylboronic acid (90 mg, 1.5 mmol), Pd(dppf)Cl₂ (73 mg, 0.1 mmol) and K₂CO₃ (276 mg, 2.0 mmol) in dioxane (10 mL) was stirred at 90° C. for 16 h under N₂ atmosphere. The reaction was cooled to ambient temperature and concentrated under reduced pressure to remove dioxane, the residue was dissolved in DCM (50 mL). The organic phase was washed with water (10 mL×2), dried over anhydrous Na₂SO₄, filtered and concentrated to give the product as a yellow solid (470 mg, 93.4%). MS (ESI, m/e) [M+1]⁺ 504.4.

Step 2: 7-(1-acryloylpiperidin-4-yl)-2-(3-chloro-5-methoxy-4-methylphenyl)-4,5,6,7-tetrahydropyrazolo[1,5-a]pyrimidine-3-carboxamide

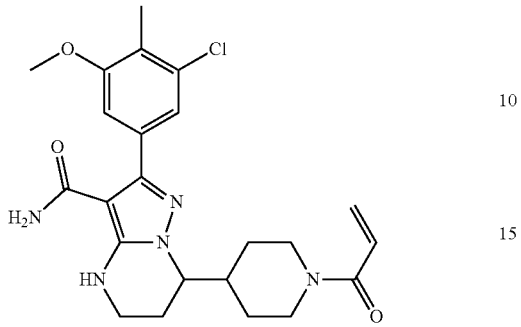

Example A35 was then synthesized from tert-butyl 4-(3-carbamoyl-2-(3-chloro-5-methoxy-4-methylphenyl)-4,5,6,7-tetrahydropyrazolo[1,5-a]pyrimidin-7-yl)piperidine-1-carboxylate following the procedures similar to those in Example A2. ¹H NMR (400 MHz, CDCl₃)) δ 7.15 (s, 1H), 6.88 (s, 1H), 6.57 (dd, J=16.6, 10.2 Hz, 1H), 6.26 (d, J=16.6 Hz, 1H), 5.70 (d, J=10.2 Hz, 1H), 4.85-4.69 (m, 1H), 4.18-4.00 (m, 2H), 3.86 (s, 3H), 3.51-3.41 (m, 2H), 3.15-2.98 (m, 1H), 2.75-2.57 (m, 1H), 2.57-2.32 (m, 1H), 2.31 (s, 3H), 2.24-2.00 (m, 2H), 1.88-1.75 (m, 1H), 1.74-1.58 (m, 1H), 1.56-1.42 (m, 1H), 1.42-1.28 (m, 1H). MS (ESI, m/e) [M+1]⁺ 458.1.

Example A36: 7-(1-acryloylpiperidin-4-yl)-2-(3-chloro-4-cyclopropyl-5-methoxyphenyl)-4,5,6,7-tetrahydropyrazolo[1,5-a]pyrimidine-3-carboxamide

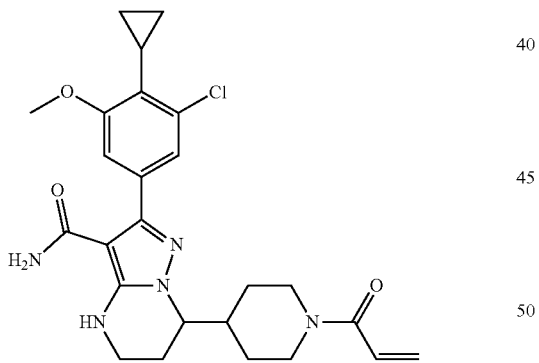

Example A36 was synthesized from tert-butyl 4-(2-(4-bromo-3-chloro-5-methoxyphenyl)-3-carbamoyl-4,5,6,7-tetrahydropyrazolo[1,5-a]pyrimidin-7-yl)piperidine-1-carboxylate (intermediate from Example A23) and cyclopropylboronic acid following the procedures similar to those in Example A35. ¹H NMR (400 MHz, DMSO-d₆)) δ 7.11 (d, J=0.8 Hz, 1H), 7.04 (d, J=0.8 Hz, 1H), 6.86-6.71 (m, 1H), 6.07 (dd, J=17.0, 2.2 Hz, 1H), 5.64 (dd, J=12.0, 2.2 Hz, 1H), 4.52-4.42 (m, 1H), 4.15-3.85 (m, 2H), 3.78 (s, 3H), 3.33-3.24 (m, 2H), 3.06-2.91 (m, 1H), 2.68-2.50 (m, 1H), 2.32-2.15 (m, 1H), 2.08-1.95 (m, 1H), 1.95-1.84 (m, 1H), 1.82-1.65 (m, 1H), 1.60-1.50 (m, 1H), 1.35-1.12 (m, 2H), 1.00-0.91 (m, 2H), 0.86-0.79 (m, 2H). MS (ESI, m/e) [M+1]⁺ 484.1.

Example A37: 7-(1-acryloylpiperidin-4-yl)-2-(4-cyclopentyl-3,5-dimethoxyphenyl)-4,5,6,7-tetrahydropyrazolo[1,5-a]pyrimidine-3-carboxamide

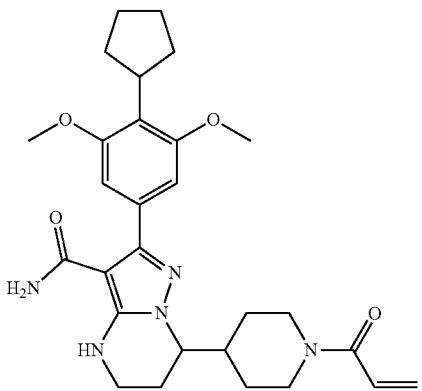 [SMILES: C=CC(=O)N1CCC(C2CCNc3c(C(N)=O)c(-c4cc(OC)c(C5CCCC5)c(OC)c4)nn32)CC1]

Step 1: methyl 4-(cyclopent-1-en-1-yl)-3,5-dimethoxybenzoate

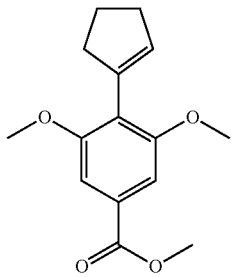

A mixture of methyl 4-bromo-3,5-dimethoxybenzoate (1.0 g, 3.64 mmol), cyclopent-1-en-1-ylboronic acid (1.24 g, 10.92 mmol), Pd(OAc)₂ (408 mg, 1.82 mmol), t-Bu₃P (10% in Hexane, 10 mL) and K₃PO₄ (2.32 g, 10.92 mmol) in dioxane (50 mL) was heated to 100° C. for two days under N₂. The mixture was filtered and the filtrate was concentrated to get crude product which was purified by column chromatograph on silica (eluent: EA:PE=1:10) to afford the product as a yellow solid (240 mg, 25.2%). MS (ESI) m/e [M+1]⁺ 263.2.

Step 2: methyl 4-cyclopentyl-3,5-dimethoxybenzoate

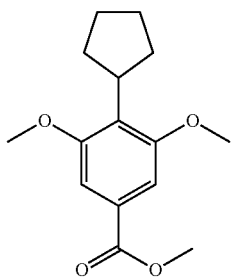

A mixture of methyl 4-(cyclopent-1-en-1-yl)-3,5-dimethoxybenzoate (240 mg, 0.92 mmol) and Pd(OH)$_2$/C (50 mg, 10% w/w) in MeOH (20 mL) and DCM (20 mL) was stirred at RT for 16 h under H$_2$ atmosphere. The mixture was filtered and the filtrate was concentrated to give the product as a yellow solid (180 mg, 75%). MS (ESI) m/e [M+1]$^+$ 265.2.

Step 3: 4-cyclopentyl-3,5-dimethoxybenzoic Acid

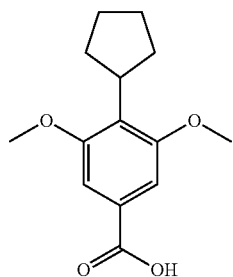

A mixture of methyl 4-cyclopentyl-3,5-dimethoxybenzoate (500 mg, 1.89 mmol) and LiOH.H$_2$O (398 mg, 9.47 mmol) in THF (10 mL) and H$_2$O (10 mL) was heated to reflux for 4 h. The mixture was cooled to ambient temperature and concentrated under reduced pressure, the residue was adjusted to the pH value of 1-2 with con. HCl and extracted with EA (20 mL×3). The combined organic layers were washed with brine, dried over Na$_2$SO$_4$, filtered and concentrated to give the product as a yellow solid (350 mg, 74.0%). MS (ESI) m/e [M+1]$^+$ 251.2.

Step 4: 7-(1-acryloylpiperidin-4-yl)-2-(4-cyclopentyl-3,5-dimethoxyphenyl)-4,5,6,7-tetrahydropyrazolo[1,5-a]pyrimidine-3-carboxamide

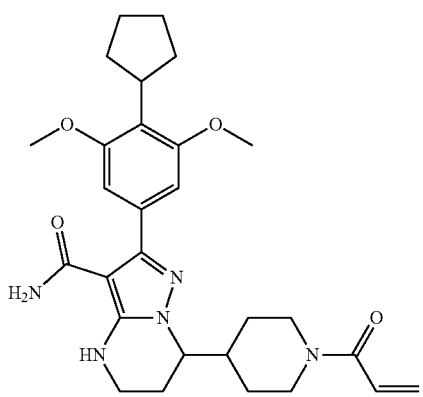 [SMILES: C=CC(=O)N1CCC(C2CCNc3c(C(N)=O)c(-c4cc(OC)c(C5CCCC5)c(OC)c4)nn32)CC1]

Example A37 was then synthesized from 4-cyclopentyl-3,5-dimethoxybenzoic acid following the procedures similar to those in Example A2 without the Suzuki reaction step. $^1$H NMR (400 MHz, DMSO-d$_6$) δ 6.79 (dd, J=16.6, 10.4 Hz, 1H), 6.73 (br s, 1H), 6.72 (s, 2H), 6.06 (dd, J=16.6, 2.0 Hz, 1H), 5.64 (dd, J=10.4 Hz, 1H), 4.52-4.42 (m, 1H), 4.15-3.98 (m, 2H), 3.76 (s, 6H), 3.65-3.55 (m, 1H), 3.33-3.24 (m, 2H), 3.05-2.90 (m, 1H), 2.60-2.50 (m, 1H), 2.30-2.15 (m, 1H), 2.10-1.95 (m, 1H), 1.95-1.64 (m, 8H), 1.62-1.50 (m, 3H), 1.35-1.12 (m, 2H). MS (ESI, m/e) [M+1]$^+$ 508.3.

Example A38: 7-(1-acryloylpiperidin-4-yl)-2-(3,5-dimethoxy-4-(trifluoromethyl)phenyl)-4,5,6,7-tetrahydropyrazolo[1,5-a]pyrimidine-3-carboxamide

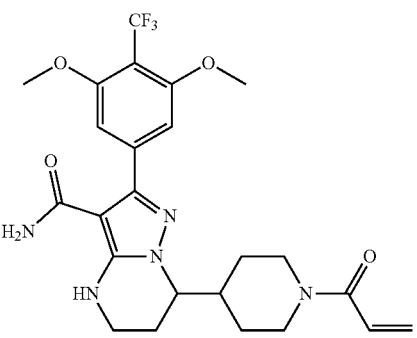 [SMILES: C=CC(=O)N1CCC(C2CCNc3c(C(N)=O)c(-c4cc(OC)c(C(F)(F)F)c(OC)c4)nn32)CC1]

Step 1: methyl 3,5-dimethoxy-4-(trifluoromethyl)benzoate

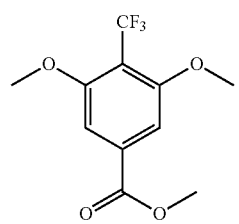

A mixture of methyl 4-bromo-3,5-dimethoxybenzoate (1.0 g, 3.64 mmol), methyl 2,2-difluoro-2-(fluorosulfonyl)acetate (2.3 mL, 18.2 mmol) and CuI (693 mg, 3.64 mmol) in DMF (10 mL) was heated to 100° C. for 16 h. The mixture was filtered and the filtrate was concentrated to give the crude product which was purified by column chromatograph on silica (eluent: EA:PE=1:10) to afford the product as an off-white solid (820 mg, 83.2%). MS (ESI) m/e [M+1]$^+$ 265.0.

Step 2: 3,5-dimethoxy-4-(trifluoromethyl)benzoic Acid

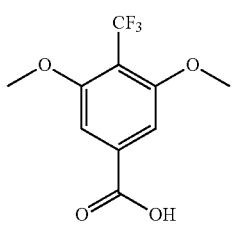

A mixture solution of methyl 3,5-dimethoxy-4-(trifluoromethyl)benzoate (1.5 g, 5.68 mmol) and LiOH.H$_2$O (1.2 g, 28.4 mmol) in THF (20 mL) and H$_2$O (20 mL) was heated to reflux for 4 h. The mixture was cooled to ambient temperature and removed THF under reduced pressure, the residue was adjusted to the pH value of 1-2 with con. HCl and extracted with EA (20 mL×3). The combined organic layers were washed with brine, dried over Na$_2$SO$_4$, filtered and concentrated to give the product as a yellow solid (1.2 g, 84.5%).

Step 3: 7-(1-acryloylpiperidin-4-yl)-2-(3,5-dimethoxy-4-(trifluoromethyl)phenyl)-4,5,6,7-tetrahydropyrazolo[1,5-a]pyrimidine-3-carboxamide

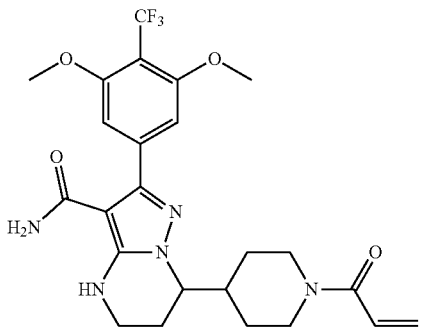

Example A38 was then synthesized from 3,5-dimethoxy-4-(trifluoromethyl)benzoic acid following the procedures similar to those in Example A2 without the Suzuki reaction step. $^1$H NMR (400 MHz, DMSO-d$_6$) δ 6.93 (s, 2H), 6.79 (dd, J=16.7, 11.2 Hz, 1H), 6.72 (br s, 1H), 6.07 (dd, J=16.7, 2.0 Hz, 1H), 5.64 (d, J=11.2 Hz, 1H), 4.55-4.45 (m, 1H), 4.15-4.02 (m, 2H), 3.84 (s, 6H), 3.32-3.25 (m, 2H), 3.08-2.95 (m, 1H), 2.64-2.53 (m, 1H), 2.30-2.15 (m, 1H), 2.10-1.98 (m, 1H), 1.95-1.85 (m, 1H), 1.75-1.66 (m, 1H), 1.62-1.50 (m, 1H), 1.35-1.20 (m, 2H). MS (ESI, m/e) [M+1]$^+$ 508.2.

Example A39: 7-(1-acryloylpiperidin-4-yl)-2-(4-cyclohexyl-3,5-dimethoxyphenyl)-4,5,6,7-tetrahydropyrazolo[1,5-a]pyrimidine-3-carboxamide

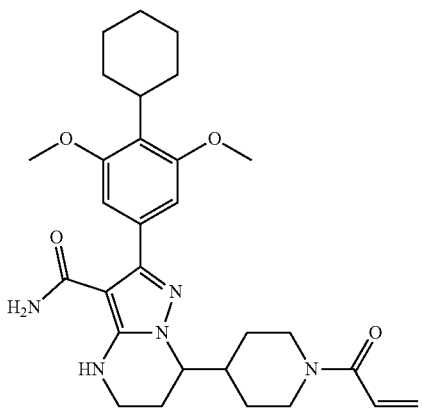 [SMILES: C=CC(=O)N1CCC(C2CCNc3c(C(N)=O)c(-c4cc(OC)c(C5CCCCC5)c(OC)c4)nn32)CC1]

Example A39 was synthesized from methyl 4-bromo-3,5-dimethoxybenzoate and cyclohex-1-en-1-ylboronic acid following the procedures similar to those in Example A37. $^1$H NMR (400 MHz, DMSO-d$_6$) δ 6.78 (dd, J=15.8, 10.6 Hz, 1H), 6.71 (br s, 1H), 6.70 (s, 2H), 6.06 (dd, J=15.8, 1.8 Hz, 1H), 5.63 (d, J=10.6 Hz, 1H), 4.52-4.40 (m, 1H), 4.15-3.97 (m, 2H), 3.76 (s, 6H), 3.32-3.28 (m, 2H), 3.25-3.12 (m, 2H), 3.05-2.92 (m, 1H), 2.60-2.50 (m, 1H), 2.34-2.15 (m, 1H), 2.11-1.95 (m, 3H), 1.95-1.85 (m, 1H), 1.80-1.62 (m, 3H), 1.60-1.50 (m, 1H), 1.49-1.40 (m, 2H), 1.38-1.13 (m, 5H). MS (ESI, m/e) [M+1]$^+$ 522.2.

Example A40: 7-(1-acryloylpiperidin-4-yl)-2-(2,6-dimethoxy-2',3',4',5'-tetrahydro-[1,1'-biphenyl]-4-yl)-4,5,6,7-tetrahydropyrazolo[1,5-a]pyrimidine-3-carboxamide

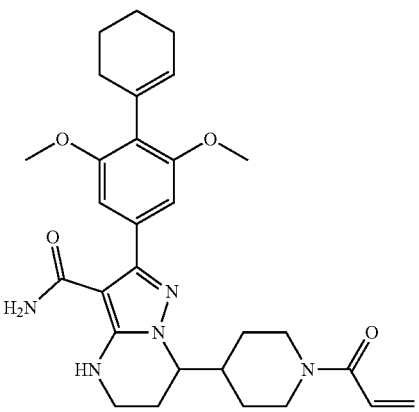 [SMILES: C=CC(=O)N1CCC(C2CCNc3c(C(N)=O)c(-c4cc(OC)c(C5=CCCCC5)c(OC)c4)nn32)CC1]

Example A40 was synthesized from 2,6-dimethoxy-2',3',4',5'-tetrahydro-[1,1'-biphenyl]-4-carboxylic acid (intermediate prepared from methyl 4-bromo-3,5-dimethoxybenzoate and cyclohex-1-en-1-ylboronic acid without the Pd(OH)$_2$/C reduction step) following the procedures similar to those in Example A2 without the Suzuki reaction step. NaBH$_4$ was used in the reduction step. $^1$H NMR (400 MHz, DMSO-d$_6$) δ 6.79 (dd, J=16.6, 10.4 Hz, 1H), 6.72 (s, 2H), 6.06 (d, J=16.6 Hz, 1H), 5.63 (d, J=10.6 Hz, 1H), 5.45-5.40 (m, 1H), 4.52-4.40 (m, 1H), 4.15-3.92 (m, 2H), 3.71 (s, 6H), 3.35-3.25 (m, 2H), 3.05-2.92 (m, 2H), 2.60-2.52 (m, 1H), 2.32-2.16 (m, 1H), 2.15-1.97 (m, 4H), 1.95-1.85 (m, 1H), 1.80-1.50 (m, 5H), 1.35-1.15 (m, 3H). MS (ESI, m/e) [M+1]$^+$ 520.2.

Example A41: (E)-7-(1-acryloylpiperidin-4-yl)-2-(3,5-dimethoxy-4-styrylphenyl)-4,5,6,7-tetrahydropyrazolo[1,5-a]pyrimidine-3-carboxamide

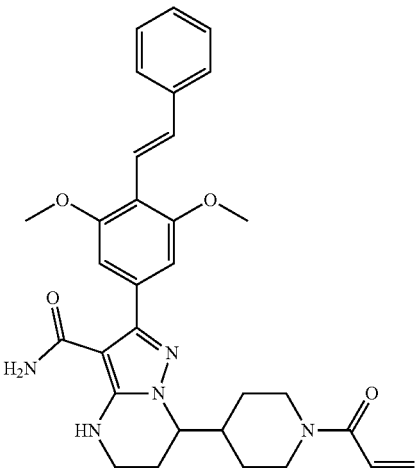 [SMILES: C=CC(=O)N1CCC(C2CCNc3c(C(N)=O)c(-c4cc(OC)c(/C=C/c5ccccc5)c(OC)c4)nn32)CC1]

Example A41 was synthesized from tert-butyl 4-(2-(4-bromo-3,5-dimethoxyphenyl)-3-cyanopyrazolo[1,5-a]pyrimidin-7-yl)piperidine-1-carboxylate and (E)-4,4,5,5-tetramethyl-2-styryl-1,3,2-dioxaborolane following the procedures similar to those in Example A2. NaBH₄ was used in the reduction step. ¹H NMR (DMSO-d₆) δ 7.58-7.48 (m, 3H), 7.42-7.34 (m, 3H), 7.28-7.22 (m, 1H), 6.83 (s, 2H) 6.82-6.72 (m, 2H), 6.07 (dd, J=16.4, 2.0 Hz, 1H), 5.64 (d, J=10.8 Hz, 1H), 4.54-4.44 (m, 1H), 4.17-4.01 (m, 2H), 3.88 (s, 6H), 3.31-3.25 (m, 2H), 3.07-2.93 (m, 1H), 2.69-2.52 (m, 1H), 2.32-2.19 (m, 1H), 2.11-1.96 (m, 1H), 1.96-1.85 (m, 1H), 1.79-1.69 (m, 1H), 1.63-1.54 (m, 1H), 1.37-1.18 (m, 2H). MS (ESI) m/e [M+1]⁺ 542.2.

Example A42: 7-(1-acryloylpiperidin-4-yl)-2-(3,5-dimethoxy-4-phenethylphenyl)-4,5,6,7-tetrahydropyrazolo[1,5-a]pyrimidine-3-carboxamide Step 1: tert-butyl 4-(3-carbamoyl-2-(3,5-dimethoxy-4-phenethylphenyl)-4,5,6,7-tetrahydropyrazolo[1,5-a]pyrimidin-7-yl)piperidine-1-carboxylate

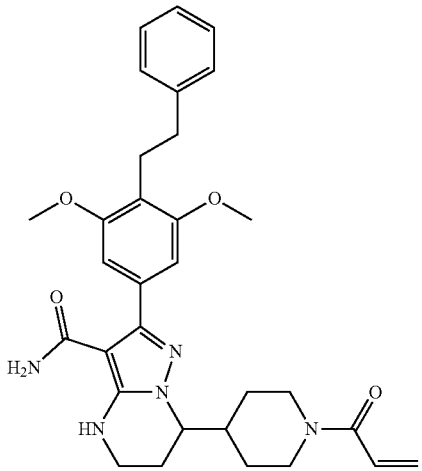 [SMILES: C=CC(=O)N1CCC(C2CCNc3c(C(N)=O)c(-c4cc(OC)c(CCc5ccccc5)c(OC)c4)nn32)CC1]

To a solution of tert-butyl (E)-4-(3-carbamoyl-2-(3,5-dimethoxy-4-styrylphenyl)-4,5,6,7-tetrahydropyrazolo[1,5-a]pyrimidin-7-yl)piperidine-1-carboxylate (intermediate from Example 41, 130 mg, 0.22 mmol) in ethanol (15 mL) was added Pd/C (50 mg), the reaction mixture was exchanged with H₂ for three times, warmed to 65° C., stirred for about 4 h. A filtration was performed, the filtrate was concentrated in vacuum to afford the product as a colorless oil (100 mg, 76.7%). MS (ESI, m/e) [M+1]⁺ 590.3.

Step 2: 7-(1-acryloylpiperidin-4-yl)-2-(3,5-dimethoxy-4-phenethylphenyl)-4,5,6,7-tetrahydropyrazolo[1,5-a]pyrimidine-3-carboxamide

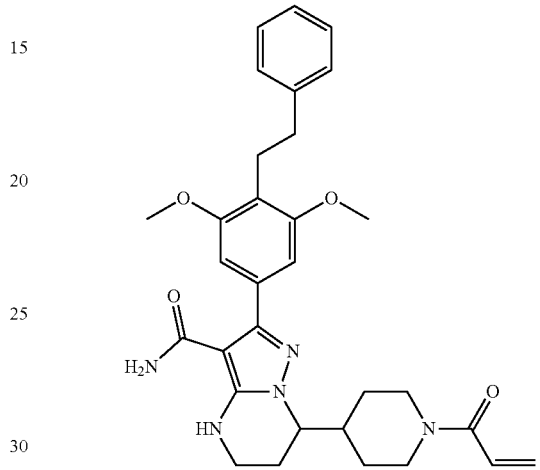

Example A42 was then synthesized from tert-butyl 4-(3-carbamoyl-2-(3,5-dimethoxy-4-phenethylphenyl)-4,5,6,7-tetrahydropyrazolo[1,5-a]pyrimidin-7-yl)piperidine-1-carboxylate following the procedures similar to those in Example A2. ¹H NMR (DMSO-d₆) δ 7.30-7.24 (m, 2H), 7.20-7.13 (m, 3H), 6.84-6.72 (m, 2H), 6.70 (m, 2H), 6.07 (dd, J=16.8, 2.4 Hz, 1H), 5.64 (d, J=10.8 Hz, 1H), 4.54-4.43 (m, 1H), 4.15-3.99 (m, 2H), 3.75 (s, 6H), 3.31-3.26 (m, 2H), 3.07-2.93 (m, 1H), 2.90-2.82 (m, 2H), 2.74-2.66 (m, 2H), 2.64-2.53 (m, 1H), 2.32-2.17 (m, 1H), 2.12-1.97 (m, 1H), 1.97-1.84 (m, 1H), 1.79-1.67 (m, 1H), 1.63-1.52 (m, 1H), 1.36-1.13 (m, 2H). MS (ESI) m/e [M+1]⁺ 544.2.

Example A43: 7-(1-acryloylpiperidin-4-yl)-2-(3,5-dimethoxy-4-(1-phenylvinyl)phenyl)-4,5,6,7-tetrahydropyrazolo[1,5-a]pyrimidine-3-carboxamide

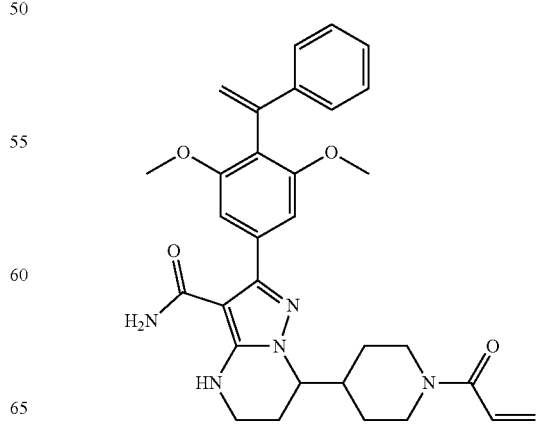

Example A43 was synthesized from tert-butyl 4-(2-(4-bromo-3,5-dimethoxyphenyl)-3-cyanopyrazolo[1,5-a]pyrimidin-7-yl)piperidine-1-carboxylate and 4,4,5,5-tetramethyl-2-(1-phenylvinyl)-1,3,2-dioxaborolane following the procedures similar to those in Example A2. NaBH$_4$ was used in the reduction step. $^1$H NMR (DMSO-d$_6$) δ 7.31-7.19 (m, 5H), 6.83 (s, 2H), 6.82-6.77 (m, 1H), 6.76 (br s, 1H), 6.07 (d, J=16.8 Hz, 1H), 5.95 (s, 1H), 5.64 (d, J=10.8 Hz, 1H), 5.11 (s, 1H), 4.56-4.43 (m, 1H), 4.18-4.01 (m, 2H), 3.65 (s, 6H), 3.33-3.25 (m, 2H), 3.08-2.92 (m, 1H), 2.65-2.52 (m, 1H), 2.36-2.19 (m, 1H), 2.12-1.86 (m, 2H), 1.81-1.69 (m, 1H), 1.66-1.52 (m, 1H), 1.38-1.16 (m, 2H). MS (ESI) m/e [M+1]$^+$ 542.2.

Example A44: 7-(1-acryloylpiperidin-4-yl)-2-(3,5-dimethoxy-4-(1-phenylethyl)phenyl)-4,5,6,7-tetrahydropyrazolo[1,5-a]pyrimidine-3-carboxamide

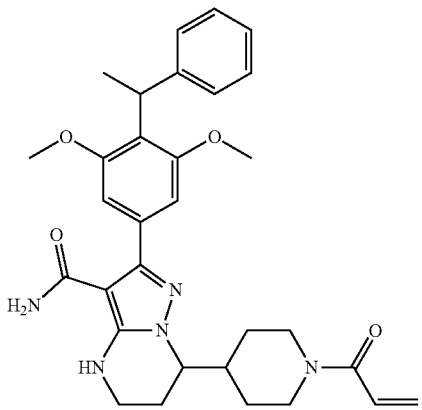 [SMILES: C=CC(=O)N1CCC(C2CCNc3c(C(N)=O)c(-c4cc(OC)c(C(C)c5ccccc5)c(OC)c4)nn32)CC1]

Example A44 was synthesized from tert-butyl 4-(3-carbamoyl-2-(3,5-dimethoxy-4-(1-phenylvinyl)phenyl)-4,5,6,7-tetrahydropyrazolo[1,5-a]pyrimidin-7-yl)piperidine-1-carboxylate following the procedures similar to those in Example A42. $^1$H NMR (DMSO-d$_6$) δ 7.26-7.18 (m, 4H), 7.14-7.07 (m, 1H), 6.83-6.69 (m, 4H), 6.06 (d, J=16.4 Hz, 1H), 5.63 (d, J=10.0 Hz, 1H), 4.76 (q, J=7.2 Hz, 1H), 4.54-4.41 (m, 1H), 4.15-3.97 (m, 2H), 3.70 (s, 6H), 3.32-3.26 (m, 2H), 3.05-2.91 (m, 1H), 2.63-2.52 (m, 1H), 2.33-2.16 (m, 1H), 2.10-1.84 (m, 2H), 1.62 (d, J=7.2 Hz, 1H), 1.60-1.50 (m, 5H), 1.35-1.13 (m, 2H). MS (ESI) m/e [M+1]$^+$ 544.2.

Example A45: 7-(1-acryloylpiperidin-4-yl)-2-(4-cyclopropyl-3-isopropoxy-5-methoxyphenyl)-4,5,6,7-tetrahydropyrazolo[1,5-a]pyrimidine-3-carboxamide

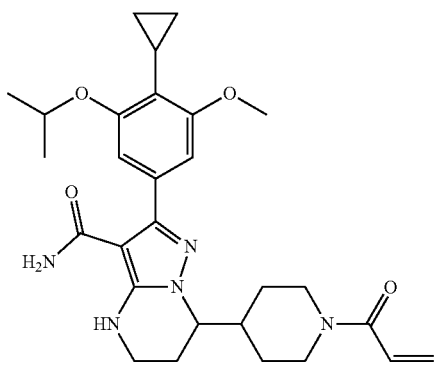 [SMILES: C=CC(=O)N1CCC(C2CCNc3c(C(N)=O)c(-c4cc(OC)c(C5CC5)c(OC(C)C)c4)nn32)CC1]

Step 1: methyl 4-bromo-3-hydroxy-5-methoxybenzoate

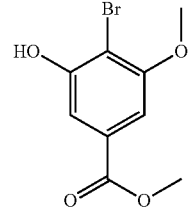

To a solution of 4-bromo-3,5-dihydroxybenzoic acid (11.6 g, 50.0 mmol) in DMF (150 mL) was added CH$_3$I (14.2 g, 100.0 mmol) and K$_2$CO$_3$ (20.7 g, 150.0 mmol), the reaction was stirred at ambient temperature for about 60 h. The reaction was quenched by water (500 mL), the mixture was extracted with EA (200 mL). The organic layer was washed with water (100 mL×2), concentrated and purified by column chromatography on silica gel (100-200 mesh, eluent: PE:EA=5:1) to give the product as a white solid (1.7 g, 13.1%). MS (ESI) m/e [M+1]$^+$ 260.9 and 262.9.

Step 2: methyl 4-bromo-3-isopropoxy-5-methoxybenzoate

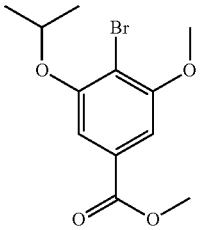 [SMILES: COC(=O)c1cc(OC)c(Br)c(OC(C)C)c1]

To a solution of methyl 4-bromo-3-hydroxy-5-methoxybenzoate (800 mg, 3.07 mmol) in DMF (20 mL) was added 2-chloropropane (585 mg, 6.15 mmol), K$_2$CO$_3$ (2.13 g, 15.38 mmol) and KI (100 mg, 0.60 mmol), the mixture was heated to 70° C., stirred for about 16 h. The reaction was cooled to ambient temperature and portioned with EA (80 mL) and H$_2$O (50 mL). The organic layer was washed with water (30 mL×2) and brine (20 mL), concentrated to give the crude product as a light yellow oil (800 mg, 86.1%).

Step 3: 7-(1-acryloylpiperidin-4-yl)-2-(4-cyclopropyl-3-isopropoxy-5-methoxyphenyl)-4,5,6,7-tetrahydropyrazolo[1,5-a]pyrimidine-3-carboxamide

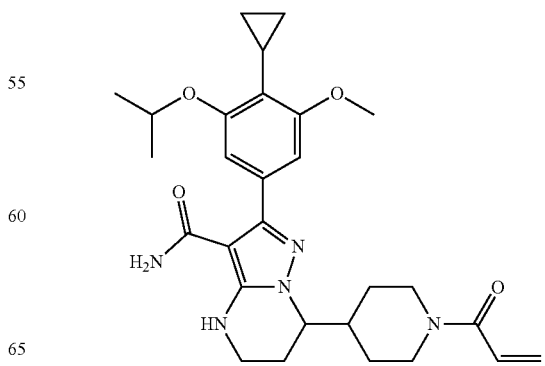

Example 45 was then synthesized from methyl 4-bromo-3-isopropoxy-5-methoxybenzoate following the procedures similar to those in Example A33. $^1$H NMR (DMSO-d$_6$) δ 6.79 (dd, J=16.4, 10.6 Hz, 1H), 6.71 (br s, 1H), 6.65 (s, 1H), 6.64 (s, 1H), 6.07 (dd, J=16.4, 2.2 Hz, 1H), 5.64 (d, J=10.6 Hz, 1H), 4.59-4.43 (m, 2H), 4.15-3.98 (m, 2H), 3.74 (s, 3H), 3.31-3.25 (m, 2H), 3.05-2.91 (m, 1H), 2.63-2.53 (m, 1H), 2.30-2.16 (m, 1H), 2.08-1.96 (m, 1H), 1.96-1.84 (m, 2H), 1.77-1.67 (m, 1H), 1.61-1.51 (m, 1H), 1.34-1.15 (m, 8H), 1.06-1.00 (m, 2H), 0.78-0.70 (m, 2H). MS (ESI) m/e [M+1]$^+$ 508.3.

Example A46: 7-(1-acryloylpiperidin-4-yl)-2-(4-(1-hydroxyethyl)-3,5-dimethoxyphenyl)-4,5,6,7-tetrahydropyrazolo[1,5-a]pyrimidine-3-carboxamide

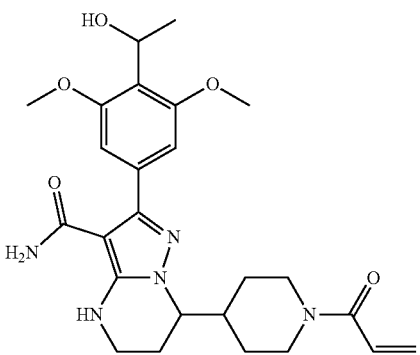 [SMILES: C=CC(=O)N1CCC(C2CCNc3c(C(N)=O)c(-c4cc(OC)c(C(C)O)c(OC)c4)nn32)CC1]

Example A46 was synthesized as a byproduct (hydroxyl group was introduced from hydrolysis step of nitrile group) from tert-butyl 4-(2-(4-bromo-3,5-dimethoxyphenyl)-3-cyanopyrazolo[1,5-a]pyrimidin-7-yl)piperidine-1-carboxylate and 4,4,5,5-tetramethyl-2-vinyl-1,3,2-dioxaborolane following the procedures similar to those in Example A2. NaBH$_4$ was used in the reduction step. $^1$H NMR (DMSO-d$_6$) δ 6.79 (dd, J=16.4, 10.6, Hz, 1H)), 6.74 (br s, 1H), 6.73 (s, 2H), 6.06 (dd, J=16.4, 2.0 Hz, 1H), 5.64 (d, J=10.6 Hz, 1H), 5.25-5.15 (m, 1H), 4.53-4.42 (m, 1H), 4.32 (dd, J=8.8, 1.6 Hz, 1H), 4.15-3.98 (m, 2H), 3.78 (s, 6H), 3.31-3.25 (m, 2H), 3.06-2.91 (m, 1H), 2.64-2.53 (m, 1H), 2.31-2.15 (m, 1H), 2.10-1.84 (m, 2H), 1.78-1.67 (m, 1H), 1.62-1.51 (m, 1H), 1.41 (d, J=6.4 Hz, 3H), 1.35-1.14 (m, 2H). MS (ESI) m/e [M–17]$^+$ 466.2.

Example A47: 7-(1-acryloylpiperidin-4-yl)-2-(4-bromo-3-chloro-5-ethoxyphenyl)-4,5,6,7-tetrahydropyrazolo[1,5-a]pyrimidine-3-carboxamide

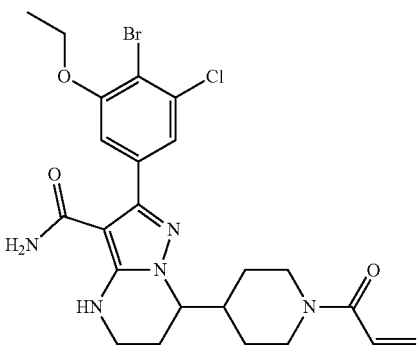 [SMILES: C=CC(=O)N1CCC(C2CCNc3c(C(N)=O)c(-c4cc(Cl)c(Br)c(OCC)c4)nn32)CC1]

Step 1: methyl 3-ethoxy-4-nitrobenzoate

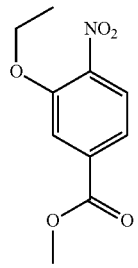

To a solution of methyl 3-hydroxy-4-nitrobenzoate (19.7 g, 100 mmol) and potassium carbonate (41.4 g, 300 mmol) in DMF (500 mL) was added iodoethane (15.5 g, 100 mmol). The mixture was stirred at RT for 16 h. The solvent was removed, H$_2$O (100 mL) was added to the residue. The solid was collected by filtration and evaporated to give a gray solid (19.0 g, 84.4%). MS (ESI, m/e) [M+1]$^+$ 226.1.

Step 2: methyl 4-amino-3-ethoxybenzoate

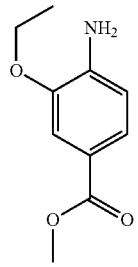

To a solution of methyl 3-ethoxy-4-nitrobenzoate (10.0 g, 44.4 mmol) in MeOH (100 mL) was added Pd/C (3.0 g). The mixture was stirred at RT for 16 h under the protection of Hydrogen. The solid was removed by filtration and the filtrate was evaporated to give the product as a colorless oil. (8.0 g, 93.2%). MS (ESI, m/e) [M+1]$^+$ 196.1.

Step 3: 7-(1-acryloylpiperidin-4-yl)-2-(4-bromo-3-chloro-5-ethoxyphenyl)-4,5,6,7-tetrahydropyrazolo[1,5-a]pyrimidine-3-carboxamide

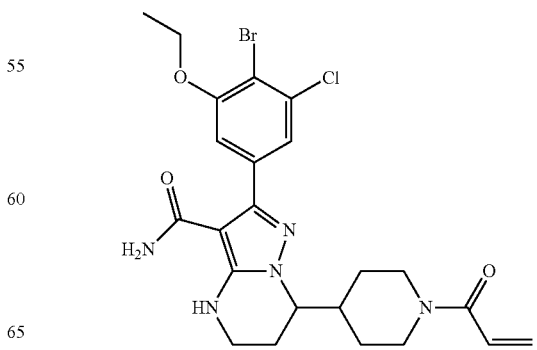

Example A47 was then synthesized from methyl 4-amino-3-ethoxybenzoate following the procedures similar to those in Example A23. $^1$H NMR (DMSO-d$_6$) δ 7.30 (s, 1H), 7.17 (s, 1H), 6.85-6.73 (m, 1H), 6.07 (d, J=16.7 Hz, 1H), 5.64 (d, J=10.5 Hz, 1H), 4.57-4.37 (m, 1H), 4.14 (q, J=7.0 Hz, 2H), 4.05-3.98 (m, 2H), 3.33-3.22 (m, 2H), 3.06-2.90 (m, 1H), 2.70-2.50 (m, 1H), 2.30-2.17 (m, 1H), 2.07-1.96 (m, 1H), 1.95-1.83 (m, 1H), 1.76-1.64 (m, 1H), 1.63-1.50 (m, 1H), 1.38 (t, J=7.0 Hz, 3H), 1.32-1.14 (m, 2H). MS (ESI) m/e [M+1]$^+$ 536.1.

Example A48: 7-(1-acryloylpiperidin-4-yl)-2-(3-chloro-4-cyclopropyl-5-ethoxyphenyl)-4,5,6,7-tetrahydropyrazolo[1,5-a]pyrimidine-3-carboxamide

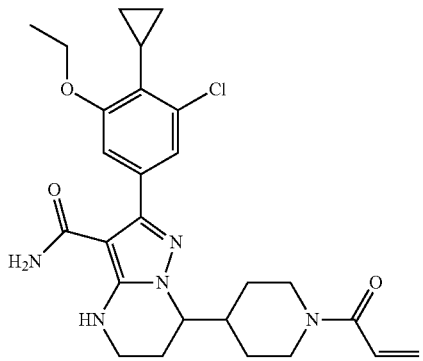 [SMILES: C=CC(=O)N1CCC(C2CCNc3c(C(N)=O)c(-c4cc(Cl)c(C5CC5)c(OCC)c4)nn32)CC1]

Step 1: tert-butyl 4-(2-(3-chloro-4-cyclopropyl-5-ethoxyphenyl)-3-cyano-4,5,6,7-tetrahydropyrazolo[1,5-a]pyrimidin-7-yl)piperidine-1-carboxylate

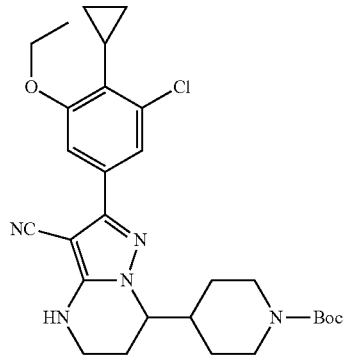 [SMILES: CCOc1cc(-c2nn3c(c2C#N)NCCC3C2CCN(C(=O)OC(C)(C)C)CC2)cc(Cl)c1C1CC1]

To a solution of tert-butyl 4-(2-(4-bromo-3-chloro-5-ethoxyphenyl)-3-cyano-4,5,6,7-tetrahydropyrazolo[1,5-a]pyrimidin-7-yl)piperidine-1-carboxylate (300 mg, 0.53 mmol, intermediate from Example A47), cyclopropylboronic acid (55 mg, 63.6 mmol) and K$_3$PO$_4$ (374 mg, 1.76 mmol) in 1,4-dioxane (100 mL) was added Pd(dppf)Cl$_2$ (30 mg, 0.04 mmol). The mixture was stirred at 90° C. for 16 h. The reaction was quenched with EA (100 ml) and H$_2$O (100 ml), the organic phase was washed with sat. NH$_4$Cl (50 mL) and sat. NaCl (100 ml), dried over anhydrous Na$_2$SO$_4$ and evaporated to give the crude product as a black solid (200 mg, 72.2%). MS (ESI, m/e) [M+1]$^+$ 526.2.

Step 2: 7-(1-acryloylpiperidin-4-yl)-2-(3-chloro-4-cyclopropyl-5-ethoxyphenyl)-4,5,6,7-tetrahydropyrazolo[1,5-a]pyrimidine-3-carboxamide

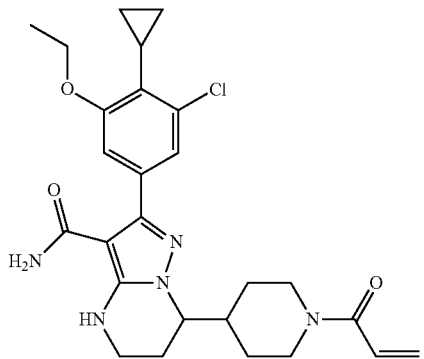 [SMILES: C=CC(=O)N1CCC(C2CCNc3c(C(N)=O)c(-c4cc(Cl)c(C5CC5)c(OCC)c4)nn32)CC1]

Example A48 was then synthesized from tert-butyl 4-(2-(3-chloro-4-cyclopropyl-5-ethoxyphenyl)-3-cyano-4,5,6,7-tetrahydropyrazolo[1,5-a]pyrimidin-7-yl)piperidine-1-carboxylate following the procedures similar to those in Example A2, NaBH$_4$ was used in the reduction step. $^1$H NMR (CDCl$_3$) δ 7.14 (s, 1H), 6.86 (s, 1H), 6.63-6.52 (m, 1H), 6.26 (d, J=16.6 Hz, 1H), 5.68 (d, J=10.3 Hz, 1H), 5.63-5.43 (br s, 1H), 4.86-4.66 (m, 1H), 4.20-3.99 (m, 3H), 3.61-3.36 (m, 2H), 3.13-2.95 (m, 1H), 2.72-2.44 (m, 2H), 2.31-2.25 (m, 1H), 2.17-1.96 (m, 4H), 1.51-1.38 (m, 3H), 1.38-1.16 (m, 4H), 1.04-0.90 (m, 4H). MS (ESI) m/e [M+1]$^+$ 498.2.

Example A49: 7-(1-acryloylpiperidin-4-yl)-2-(3-chloro-5-ethoxy-4-methylphenyl)-4,5,6,7-tetrahydropyrazolo[1,5-a]pyrimidine-3-carboxamide

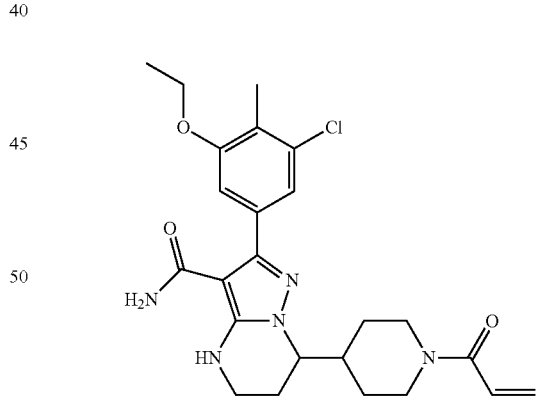

Example A49 was synthesized from tert-butyl 4-(2-(4-bromo-3-chloro-5-ethoxyphenyl)-3-cyano-4,5,6,7-tetrahydropyrazolo[1,5-a]pyrimidin-7-yl)piperidine-1-carboxylate and methylboronic acid following the procedures similar to those in Example A48. $^1$H NMR (CDCl$_3$) δ 7.14 (s, 1H), 6.87 (s, 1H), 6.66-6.53 (m, 2H), 6.27 (d, J=16.7 Hz, 1H), 5.68 (d, J=10.7 Hz, 1H), 4.86-4.66 (m, 1H), 4.20-3.95 (m, 3H), 3.64-3.36 (m, 2H), 3.10-2.97 (m, 1H), 2.72-2.44 (m, 2H), 2.31 (s, 3H), 2.14-2.02 (m, 2H), 1.87-1.73 (m, 1H), 1.7-1.58 (m, 1H), 1.44 (d, J=6.8 Hz, 3H) 1.38-1.16 (m, 4H). MS (ESI) m/e [M+1]$^+$ 472.2.

Example A50: 2-(3,5-dimethoxy-4-methylphenyl)-7-(1-propioloylpiperidin-4-yl)-4,5,6,7-tetrahydropyrazolo[1,5-a]pyrimidine-3-carboxamide

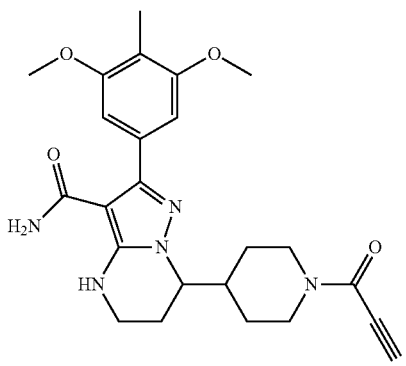 [SMILES: C#CC(=O)N1CCC(C2CCNc3c(C(N)=O)c(-c4cc(OC)c(C)c(OC)c4)nn32)CC1]

To a solution of propiolic acid (175 mg, 2.5 mmol) in DCM (30 mL) was dropwisely added oxalyl dichloride (1.0 mL) at 0° C., the solution was stirred at 0° C. for 2 h. The solvent was removed and the residue was dissolved in DCM (2.0 mL), the solution was added to the mixture of 2-(3,5-dimethoxy-4-methylphenyl)-7-(piperidin-4-yl)-4,5,6,7-tetrahydropyrazolo[1,5-a]pyrimidine-3-carboxamide (200 mg, 0.5 mmol, Intermediate from Example A1) and TEA (150 mg, 1.5 mmol) in DCM (30 mL), the reaction was stirred at RT for 3 h. The organic phase was washed with sat. NaHCO$_3$ (100 mL) and sat. NaCl (100 mL), dried over anhydrous Na$_2$SO$_4$, filtered and concentrated, the residue was purified by pre-TLC (DCM:MeOH=50:1) to afford the product (5 mg, 2.3%). $^1$H NMR (DMSO-d$_6$) δ 6.71 (s, 2H), 4.52-4.46 (m, 1H), 4.40-4.31 (m, 1H), 4.31-4.22 (m, 1H), 4.17-4.01 (m, 1H), 3.78 (s, 6H), 3.33-3.25 (m, 2H), 3.16-3.09 (m, 1H), 2.71-2.57 (m, 1H), 2.31-2.16 (m, 1H), 2.03 (s, 3H), 2.03-1.96 (m, 1H), 1.95-1.86 (m, 1H), 1.84-1.70 (m, 1H), 1.67-1.53 (m, 1H), 1.40-1.18 (m, 2H). MS (ESI) m/e [M+1]$^+$ 452.2.

Example A51: 7-(1-acryloylpiperidin-4-yl)-2-(3,5-dimethoxy-4-vinylphenyl)-4,5,6,7-tetrahydropyrazolo[1,5-a]pyrimidine-3-carboxamide

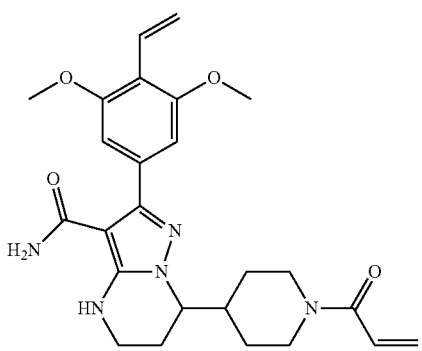 [SMILES: C=CC(=O)N1CCC(C2CCNc3c(C(N)=O)c(-c4cc(OC)c(C=C)c(OC)c4)nn32)CC1]

To a solution of 7-(1-acryloylpiperidin-4-yl)-2-(4-bromo-3,5-dimethoxyphenyl)-4,5,6,7-tetrahydropyrazolo[1,5-a]pyrimidine-3-carboxamide (250 mg, 0.48 mmol, Intermediate from Example 6) in dioxane (5 mL) and 1 M K$_2$CO$_3$ (2.5 mL) was added 4,4,5,5-tetramethyl-2-vinyl-1,3,2-dioxaborolane (149 mg, 0.96 mmol) and Pd(dppf)Cl$_2$ (37 mg, 0.05 mmol), the reaction atmosphere was exchanged with N$_2$ for three times, warmed to 90° C. and stirred for about 17 h. Cooled to ambient temperature, the mixture was concentrated and purified by column chromatograph on silica gel (100-200 mesh, eluent: DCM:MeOH=30:1) to give the crude product (100 mg) which was further purified by pre-HPLC to afford the product (50 mg, 22.3%). $^1$H NMR (DMSO-d$_6$) δ 6.89 (dd, J=18.0, 12.0 Hz, 1H), 6.84-6.66 (m, 4H), 6.12-6.07 (m, 2H), 5.64 (d, J=11.2 Hz, 1H), 5.39 (dd, J=12.0, 2.8 Hz, 1H), 4.55-4.40 (m, 1H), 4.15-3.97 (m, 2H), 3.82 (s, 6H), 3.32-3.25 (m, 2H), 3.08-2.90 (m, 1H), 2.65-2.52 (m, 1H), 2.33-2.16 (m, 1H), 2.10-1.85 (m, 2H), 1.80-1.67 (m, 1H), 1.64-1.51 (m, 1H), 1.37-1.14 (m, 2H). MS (ESI) m/e [M+1]$^+$ 466.2.

Example A52: 7-(1-acryloylpiperidin-4-yl)-2-(4-cyclopropyl-3,5-bis(methoxy-d3)phenyl)-4,5,6,7-tetrahydropyrazolo[1,5-a]pyrimidine-3-carboxamide

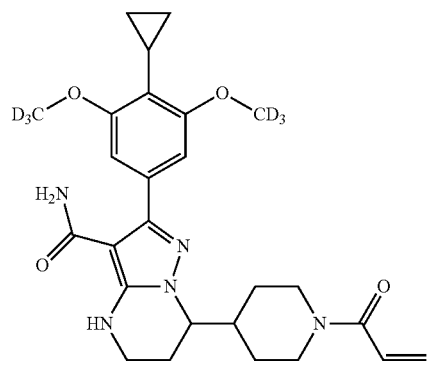 [SMILES: [2H]C([2H])([2H])Oc1cc(-c2nn3c(c2C(N)=O)NCCC3C2CCN(C(=O)C=C)CC2)cc(OC([2H])([2H])[2H])c1C1CC1]

Example A52 was synthesized from methyl 4-bromo-3,5-dihydroxybenzoate and CD$_3$I following the procedures similar to those in Example A2. $^1$H NMR (400 MHz, DMSO-d$_6$) δ 6.78 (dd, J=16.8, 10.8 Hz, 1H), 6.73 (br s, 1H), 6.67 (s, 2H), 6.06 (dd, J=16.8, 2.2 Hz, 1H), 5.64 (d, J=10.8 Hz, 1H), 4.54-4.40 (m, 1H), 4.15-3.97 (m, 2H), 3.50-3.20 (m, 3H), 3.05-2.90 (m, 1H), 2.63-2.52 (m, 1H), 2.30-2.15 (m, 1H), 2.10-1.81 (m, 3H), 1.77-1.10 (m, 3H), 1.02-0.90 (m, 2H), 0.82-0.68 (m, 2H). MS (ESI, m/e) [M+1]$^+$ 486.2.

Example A52a and A52b: (S or R)-7-(1-acryloylpiperidin-4-yl)-2-(4-cyclopropyl-3,5-bis(methoxy-d3)phenyl)-4,5,6,7-tetrahydropyrazolo[1,5-a]pyrimidine-3-carboxamide and (R or S)-7-(1-acryloylpiperidin-4-yl)-2-(4-cyclopropyl-3,5-bis(methoxy-d3)phenyl)-4,5,6,7-tetrahydropyrazolo[1,5-a]pyrimidine-3-carboxamide A52a

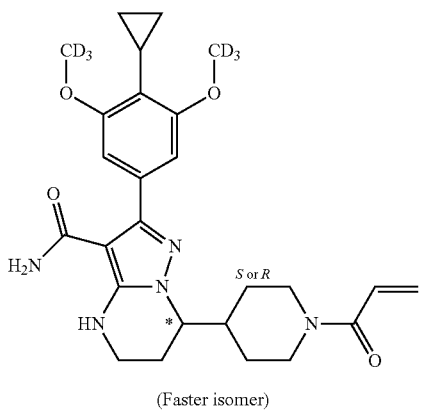

(Faster isomer)

-continued

A52b

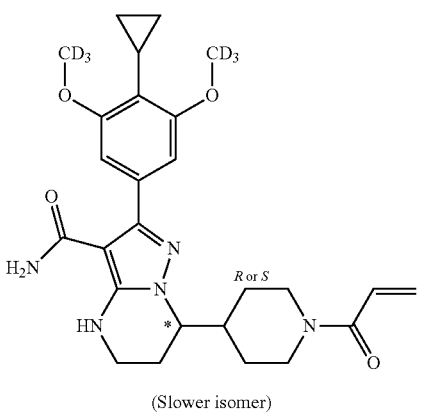

(Slower isomer)

Two enantiomers A52a (faster isomer) and A52b (slower isomer) were separated by chiral preparative HPLC. The chiral separation conditions are shown below. The faster enantiomer was eluted at retention time of around 4.2 min. The slower enantiomer was eluted at retention time of around 5.5 min.

| Column | CHIRAL ART Cellulose-SB |
|---|---|
| Column size | 2 cm × 25 cm, 5 um |
| Injection | 0.5 mL |
| Mobile phase | Hex:EtOH = 50:50 |
| Flow rate | 20 ml/min |
| Wave length | UV 220 nm |
| Temperature | 25° C. |
| Sample solution | 11.7 mg/mL in EtOH:DCM = 3:1 |
| Prep-HPLC equipment | Prep-Gilson-HPLC |

A52a was assigned to (S)-configuraton and A52b was assigned to (R)-configuration:

A52a

A52b

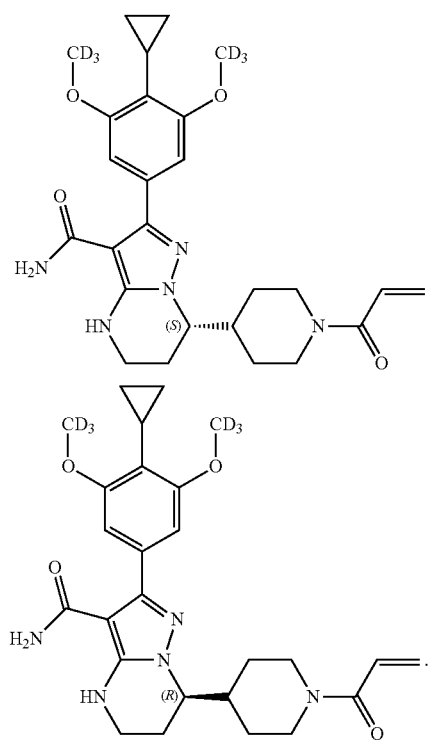

Example B1: 7-(1-acryloylazetidin-3-yl)-2-(3,5-dichloro-4-methylphenyl)-4,5,6,7-tetrahydropyrazolo[1,5-a]pyrimidine-3-carboxamide

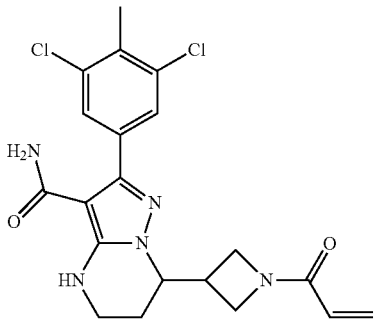 [SMILES: C=CC(=O)N1CC(C2CCNc3c(C(N)=O)c(-c4cc(Cl)c(C)c(Cl)c4)nn32)C1]

Example B1 was synthesized from 5-amino-3-(3,5-dichloro-4-methylphenyl)-1H-pyrazole-4-carbonitrile (intermediate from Example A7) and tert-butyl 3-(3-(dimethylamino)acryloyl)azetidine-1-carboxylate (ref: WO2014173289A1) following the procedures similar to those in Example A2 without the Suzuki reaction step. NaBH$_4$ was used in the reduction step. $^1$H NMR (400 MHz, DMSO-d$_6$) δ 7.56 (s, 2H), 6.62 (s, 1H), 6.39-6.24 (m, 1H), 6.14-6.03 (m, 1H), 5.68-5.58 (m, 1H), 4.45-4.35 (m, 2H), 4.34-3.80 (m, 3H), 3.33-3.20 (m, 1H), 3.08-2.88 (m, 2H), 2.44 (s, 3H), 2.14-2.00 (m, 1H), 1.81-1.66 (m, 1H). MS (ESI, m/e) [M+1]$^+$ 434.1.

Example B2: 7-(1-acryloylazetidin-3-yl)-2-(4-bromo-3,5-dimethoxyphenyl)-4,5,6,7-tetrahydropyrazolo[1,5-a]pyrimidine-3-carboxamide

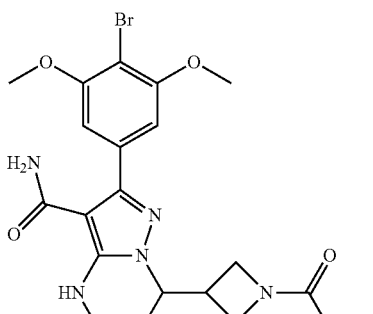

Example B2 was synthesized from 5-amino-3-(4-bromo-3,5-dimethoxyphenyl)-1H-pyrazole-4-carbonitrile (intermediate from Example A2) following the procedures similar to those in Example B1. $^1$H NMR (400 MHz, DMSO-d$_6$) δ 6.84 (s, 1H), 6.83 (s, 1H), 6.75 (br s, 1H), 6.36-6.27 (m, 1H), 6.10-6.05 (m, 1H), 5.67-5.60 (m, 1H), 4.45-3.95 (m, 5H), 3.85 (s, 3H), 3.84 (s, 3H), 3.32-3.25 (m, 2H), 3.05-2.95 (m, 1H), 2.15-2.07 (m, 1H), 1.84-1.67 (m, 1H). MS (ESI, m/e) [M+1]$^+$ 490.1 and 492.1.

Example B3: 7-(1-acryloylazetidin-3-yl)-2-(3,5-dimethoxy-4-methylphenyl)-4,5,6,7-tetrahydropyrazolo[1,5-a]pyrimidine-3-carboxamide

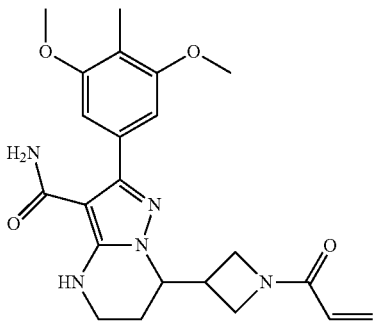 [SMILES: C=CC(=O)N1CC(C2CCNc3c(C(N)=O)c(-c4cc(OC)c(C)c(OC)c4)nn32)C1]

Example B3 was synthesized from 5-amino-3-(3,5-dimethoxy-4-methylphenyl)-1H-pyrazole-4-carbonitrile (intermediate from Example A1) following the procedures similar to those in Example B1. $^1$H NMR (400 MHz, DMSO-$d_6$) δ 6.76 (br s, 1H), 6.70 (s, 2H), 6.37-6.26 (m, 1H), 6.11-6.03 (m, 1H), 5.68-5.59 (m, 1H), 4.42-4.33 (m, 1H), 4.32-4.25 (m, 0.5H), 4.20-4.14 (m, 0.5H), 4.12-4.06 (m, 0.5H), 4.04-3.95 (m, 1H), 3.90-3.84 (m, 0.5H), 3.78 (s, 6H), 3.33-3.25 (m, 2H), 3.05-2.90 (m, 1H), 2.36-2.23 (m, 1H), 2.15-2.05 (m, 1H), 2.03 (s, 3H), 1.83-1.69 (m, 1H). MS (ESI) m/e [M+1]$^+$ 426.2.

Example C1: 7-acryloyl-2-(3,5-dimethoxy-4-methylphenyl)-5,5a,6,7,8,8a-hexahydro-4H-pyrazolo[1,5-a]pyrrolo[3,4-e]pyrimidine-3-carboxamide Example C1 was synthesized from 5-amino-3-(3,5-dimethoxy-4-methylphenyl)-1H-pyrazole-4-carbonitrile (intermediate from Example A1) and tert-butyl-3-((dimethylamino)methylene)-4-oxopyrrolidine-1-carboxylate (ref: WO2014173289) following the procedures similar to those in Example A1. $^1$H NMR (400 MHz, DMSO-$d_6$) δ 6.87-6.79 (m, 1H), 6.73 (s, 2H), 6.63-6.52 (m, 1H), 6.20-6.05 (m, 1H), 5.72-5.60 (m, 1H), 4.75-4.60 (m, 1H), 4.25-4.05 (m, 1H), 4.02-3.85 (m, 1H), 3.78 (s, 6H), 3.75-3.65 (m, 1H), 3.55- 3.45 (m, 2H), 3.17-3.06 (m, 1H), 3.05-2.92 (m, 1H), 2.03 (s, 3H). MS (ESI) m/e [M+1]$^+$ 411.9.

Example C2: 7-acryloyl-2-(3,4,5-trimethoxyphenyl)-5,5a,6,7,8,8a-hexahydro-4H-pyrazolo[1,5-a]pyrrolo[3,4-e]pyrimidine-3-carboxamide Example C2 was synthesized from 3,4,5-trimethoxybenzoic acid following the procedures similar to those in Example A2 and C1. $^1$H NMR (400 MHz, DMSO-$d_6$) δ 6.78 (s, 2H), 6.56 (dd, J=16.8, 10.4 Hz, 1H), 6.15-6.06 (m, 1H), 5.70-5.61 (m, 1H), 4.71-4.60 (m, 1H), 4.22-4.06 (m, 1H), 4.00-3.75 (m, 7H), 3.69 (s, 3H), 3.52-3.43 (m, 1H), 3.42-3.34 (m, 1H), 3.33-3.24 (m, 1H), 3.15-3.04 (m, 1H), 3.03-2.90 (m, 1H). MS (ESI) m/e [M+1]$^+$ 427.8.

Example D1: 7-acryloyl-2-(3,5-dimethoxy-4-methylphenyl)-4,5,5a,6,7,8,9,9a-octahydropyrazolo[1,5-a]pyrido[3,4-e]pyrimidine-3-carboxamide Example D1 was synthesized from 5-amino-3-(3,5-dimethoxy-4-methylphenyl)-1H-pyrazole-4-carbonitrile (intermediate from Example A1) and tert-butyl-3-((dimethylamino)methylene)-4-oxopiperidine-1-carboxylate (ref: WO2014173289) following the procedures similar to those in example A2 without the Suzuki reaction step. NaBH$_4$ was used in the reduction step. $^1$H NMR (DMSO-d$_6$) δ 6.94-6.77 (m, 1H), 6.72 (s, 2H), 6.20-6.06 (m, 1H), 5.75-5.64 (m, 1H), 4.46-4.37 (m, 1H), 3.79 (s, 6H), 3.76-3.63 (m, 3H), 3.35-3.26 (m, 2H), 3.24-3.15 (m, 1H), 2.40-2.39 (m, 1H), 2.16-2.06 (m, 1H), 2.03 (s, 3H), 2.00-1.94 (m, 1H). MS (ESI) m/e [M+1]$^+$ 426.2.

Example D2: 7-acryloyl-2-(3,5-dimethoxy-4-methylphenyl)-4,4a,5,6,7,8,8a,9-octahydropyrazolo[1,5-a]pyrido[4,3-d]pyrimidine-3-carboxamide

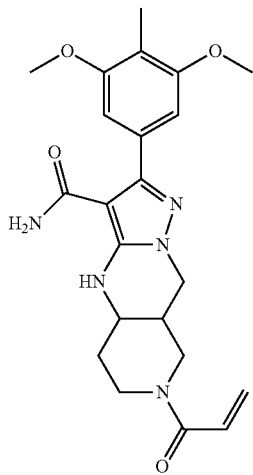

Example D2 is a byproduct when preparing Example D1. $^1$H NMR (DMSO-d$_6$) δ 6.88 (dd, J=16.5, 10.6 Hz, 1H), 6.73 (s, 2H), 6.55 (br s, 1H), 6.13 (dd, J=16.5, 2.0 Hz, 1H), 5.71 (d, J=10.6 Hz, 1H), 4.73-4.53 (m, 1H), 4.33-4.11 (m, 2H), 3.78 (s, 6H), 3.70-3.59 (m, 1.5H), 3.31-3.18 (m, 1H), 3.18-3.07 (m, 0.5H), 2.99-2.84 (m, 0.5H), 2.77-2.63 (m, 0.5H), 2.30-2.16 (m, 1H), 2.03 (s, 3H), 1.92-1.73 (m, 1H), 1.49-1.27 (m, 1H). MS (ESI) m/e [M+1]$^+$ 426.2.

Example E1: 7-(acrylamidomethyl)-2-(3,5-dimethoxy-4-methylphenyl)-4,5,6,7-tetrahydropyrazolo[1,5-a]pyrimidine-3-carboxamide

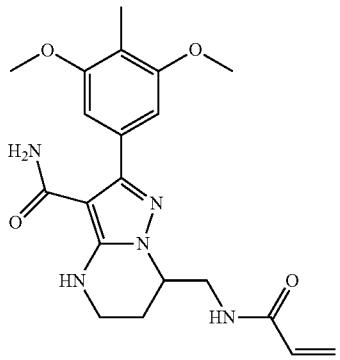 [SMILES: C=CC(=O)NCC1CCNc2c(C(N)=O)c(-c3cc(OC)c(C)c(OC)c3)nn21]

Step 1: 2-(2-oxopropyl)isoindoline-1,3-dione

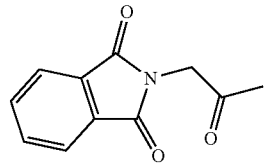

To a solution of potassium 1,3-dioxoisoindolin-2-ide (125.0 g, 678.1 mmol) in DMF (500 mL) was added 1-chloropropan-2-one (57 g, 594.0 mmol), the reaction mixture was stirred at ambient temperature for about 60 h. The reaction mixture was poured into ice water (1.0 L), the resulting mixture was stirred for about 1 h. The precipitate was collected by filtration and dried in vacuum to afford the product as a white solid (101.2 g, 81.3%). MS (ESI, m/e) [M+1]$^+$ 203.9.

Step 2: 2-(4-(dimethylamino)-2-oxobut-3-en-1-yl)isoindoline-1,3-dione

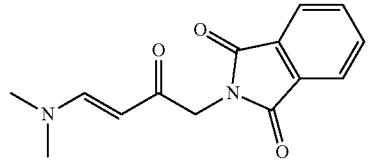 [SMILES: CN(C)/C=C/C(=O)CN1C(=O)c2ccccc2C1=O]

A solution of 2-(2-oxopropyl)isoindoline-1,3-dione (101.0 g, 500.0 mmol) in 1,1-dimethoxy-N,N-dimethylmethanamine (400 mL) was heated at 70° C. for about 16 h. Cooled to ambient temperature, PE (200 mL) was added, the mixture was stirred at ambient temperature for 1 h. The precipitate was collected by filtration. The solids were placed into a 500 ml round-bottom flask, HOAc (120 mL) was added, the mixture was stirred at ambient temperature for 40 min and filtrated, the filtrate was concentrated to remove HOAc. The residue was recrystallized from EA (150 mL) to give the product as a yellow solid (18 g, 14.0%). MS (ESI, m/e) [M+1]$^+$ 258.9.

Step 3: 2-(3,5-dimethoxy-4-methylphenyl)-7-((1,3-dioxoisoindolin-2-yl)methyl) pyrazolo[1,5-a]pyrimidine-3-carbonitrile

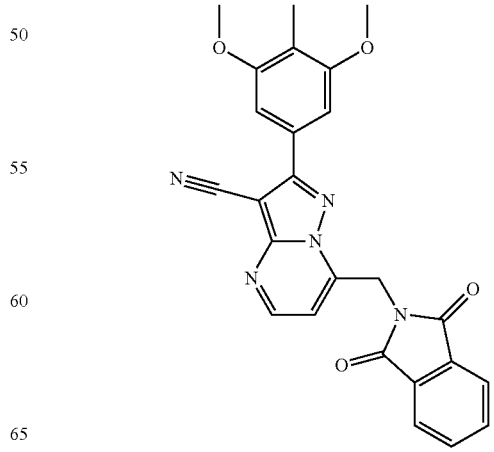

To a solution of 2-(4-(dimethylamino)-2-oxobut-3-en-1-yl)isoindoline-1,3-dione (1.0 g, 4.0 mmol) in toluene (30 mL) was added 5-amino-3-(3,5-dimethoxy-4-methylphenyl)-1H-pyrazole-4-carbonitrile (1.0 g, 4.0 mmol, intermediate from Example A1) and HOAc (2.0 mL), the reaction was stirred at 95° C. for about 16 h. The reaction mixture was cooled to ambient temperature and concentrated under reduced pressure. The residue was recrystallized from EA (25 mL) to afford the product as a brown solid (1.15 g, 65.5%). MS (ESI, m/e) [M+1]$^+$ 454.1.

Step 4: 7-(aminomethyl)-2-(3,5-dimethoxy-4-methylphenyl)-4,5,6,7-tetrahydropyrazolo[1,5-a]pyrimidine-3-carbonitrile

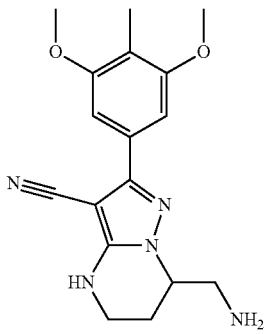 [SMILES: COc1cc(-c2nn3c(c2C#N)NCCC3CN)cc(OC)c1C]

To a solution of 2-(3,5-dimethoxy-4-methylphenyl)-7-((1,3-dioxoisoindolin-2-yl)methyl)pyrazolo[1,5-a]pyrimidine-3-carbonitrile (1.1 g, 2.43 mmol) in DCM (20 mL) and methanol (10 mL) was added NaBH$_4$ (460 mg, 12.13 mmol) in portions, the reaction was stirred at ambient temperature for 1 h. EtOH (30 mL) and Hydrazine hydrate (20 mL) was added into above solution, then heated at 90° C. for about 16 h. Cooled to ambient temperature, the mixture was concentrated to remove organic solvent, then EtOH (20 mL) and Hydrazine hydrate (10 mL) was added, the resulting mixture was heated at 105° C. for about 6 h. Cooled to ambient temperature, concentrated to remove EtOH, the resulting mixture was extracted with EA (50 mL×2). The combined organic phases were concentrated and purified by column chromatograph on silica gel (100-200 mesh, eluent: DCM:MeOH=20:1) to afford the product as a white solid (300 g, 37.8%). MS (ESI, m/e) [M+1]$^+$ 327.3.

Step 5: N-((3-cyano-2-(3,5-dimethoxy-4-methylphenyl)-4,5,6,7-tetrahydropyrazolo[1,5-a]pyrimidin-7-yl)methyl)acrylamide

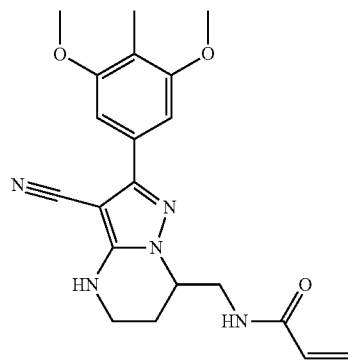 [SMILES: C=CC(=O)NCC1CCNc2c(C#N)c(-c3cc(OC)c(C)c(OC)c3)nn21]

To a solution of 7-(aminomethyl)-2-(3,5-dimethoxy-4-methylphenyl)-4,5,6,7-tetrahydropyrazolo[1,5-a]pyrimidine-3-carbonitrile (150 mg, 0.46 mmol) in DCM (10 mL) was added TEA (230 mg, 2.30 mmol) and acryloyl chloride (83 mg, 0.92 mmol), the mixture was stirred at ambient temperature for about 20 min. The mixture was diluted with DCM (20 mL), washed with H$_2$O (10 mL×2) and sat. NaCl (10 mL), dried over anhydrous Na$_2$SO$_4$, filtered and concentrated to give the crude product as a yellow solid (150 mg, 85.8%).

Step 5: 7-(acrylamidomethyl)-2-(3,5-dimethoxy-4-methylphenyl)-4,5,6,7-tetrahydropyrazolo[1,5-a]pyrimidine-3-carboxamide

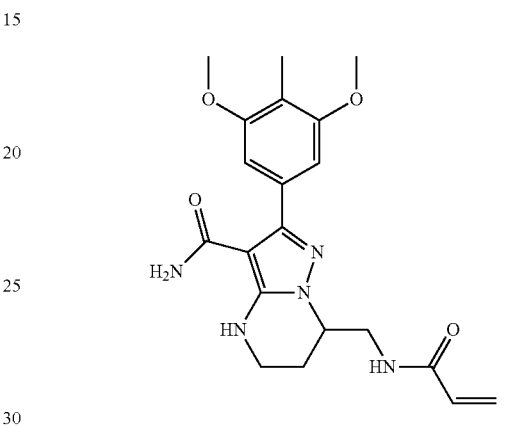

N-((3-cyano-2-(3,5-dimethoxy-4-methylphenyl)-4,5,6,7-tetrahydropyrazolo[1,5-a]pyrimidin-7-yl)methyl)acrylamide (150 mg, 0.39 mmol) was dissolved in MsOH (5.0 mL), the solution was stirred at 80° C. for about 2.5 h. Cooled to about 0° C., the pH of the mixture was adjusted to around 14 with 3 N NaOH, the resulting mixture was extracted with DCM (20 mL×3). The combined organic phases were washed with sat. NaCl (10 mL), dried over anhydrous Na$_2$SO$_4$, filtered and concentrated to give the crude product (180 mg) which was purified by pre-TLC (DCM:MeOH=25:1) to give the product (70 mg, 44.5%). $^1$H NMR (400 MHz, DMSO-d$_6$) δ 8.35 (t, J=5.8 Hz, 1H), 6.76 (br s, 1H), 6.74 (s, 2H), 6.28 (dd, J=17.0, 10.2 Hz, 1H), 6.12 (d, J=17.0 Hz, 1H), 5.63 (d, J=10.2 Hz, 1H), 4.25-4.15 (m, 1H), 3.83-3.74 (m, 1H), 3.79 (s, 6H), 3.45-3.37 (m 1H), 3.36-3.26 (m, 2H), 2.08-1.90 (m, 2H), 2.03 (s, 3H). MS (ESI) m/e [M+1]$^+$ 400.2.

Example F1: 7-(7-acryloyl-7-azaspiro[3.5]nonan-2-yl)-2-(3,5-dimethoxy-4-methylphenyl)-4,5,6,7-tetrahydropyrazolo[1,5-a]pyrimidine-3-carboxamide

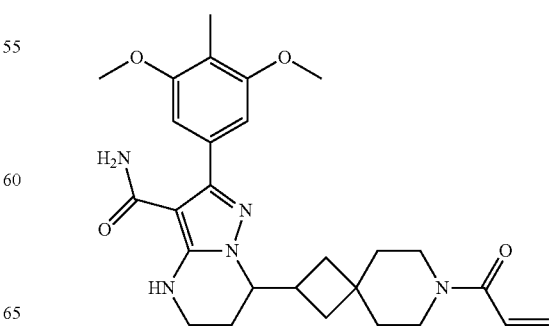

Example F1 was synthesized from 5-amino-3-(3,5-dimethoxy-4-methylphenyl)-1H-pyrazole-4-carbonitrile (intermediate from Example A1) and tert-butyl 2-(3-(dimethylamino)acryloyl)-7-azaspiro[3.5]nonane-7-carboxylate (ref: WO2014173289) following the procedures similar to those in example A2 without the Suzuki reaction step. $^1$H NMR (400 MHz, DMSO-$d_6$) δ 6.83-6.72 (m, 1H), 6.70 (br s, 1H), 6.69 (s, 2H), 6.04 (dd, J=16.8, 2.3 Hz, 1H), 5.62 (dd, J=10.6, 2.3 Hz, 1H), 4.14-4.04 (m, 1H), 3.78 (s, 6H), 3.50-3.42 (m, 2H), 3.40-3.35 (m, 2H), 3.27-3.20 (m, 2H), 2.63-2.53 (m, 1H), 2.03 (s, 3H), 2.00-1.76 (m, 5H), 1.75-1.65 (m, 1H), 1.60-1.50 (m, 2H), 1.45-1.35 (m, 2H). MS (ESI, m/e) [M+1]$^+$ 494.3.

Example G1: 7-(3-acryloyl-3-azabicyclo[3.2.1]octan-8-yl)-2-(3,5-dimethoxy-4-methylphenyl)-4,5,6,7-tetrahydropyrazolo[1,5-a]pyrimidine-3-carboxamide

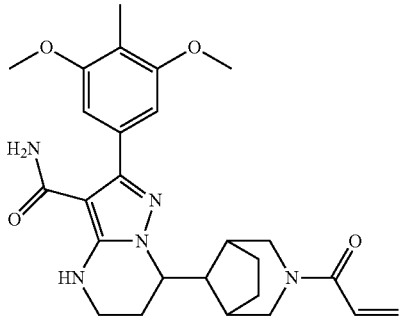 [SMILES: C=CC(=O)N1CC2CCC(C1)C2C1CCNc2c(C(N)=O)c(-c3cc(OC)c(C)c(OC)c3)nn21]

Example G1 was synthesized from 5-amino-3-(3,5-dimethoxy-4-methylphenyl)-1H-pyrazole-4-carbonitrile (intermediate from Example A1) and tert-butyl 8-(3-(dimethylamino)acryloyl)-3-azabicyclo[3.2.1]octane-3-carboxylate (ref: WO2014173289) following the procedures similar to those in example A2 without the Suzuki reaction step. NaBH$_4$ was used in the reduction step. $^1$H NMR (400 MHz, DMSO-$d_6$) δ 6.84-6.73 (m, 1H), 6.71 (s, 2H), 6.06 (d, J=16.4 Hz, 1H), 5.63 (d, J=10.8 Hz, 1H), 4.32-4.16 (m, 1H), 3.95-3.80 (m, 3H), 3.78 (s, 6H), 3.45-3.30 (m, 2H), 3.20-3.00 (m, 1H), 2.77-2.56 (m, 1H), 2.30-2.20 (m, 1H), 2.15-2.05 (m, 1H), 2.03 (s, 3H), 2.02-1.95 (m 2H), 1.93-1.69 (m, 2H), 1.40-1.30 (m, 2H). MS (ESI, m/e) [M+1]$^+$ 508.2.

Example H1: 7-(2-acryloyl-2-azaspiro[3.3]heptan-6-yl)-2-(3,5-dimethoxy-4-methylphenyl)-4,5,6,7-tetrahydropyrazolo[1,5-a]pyrimidine-3-carboxamide

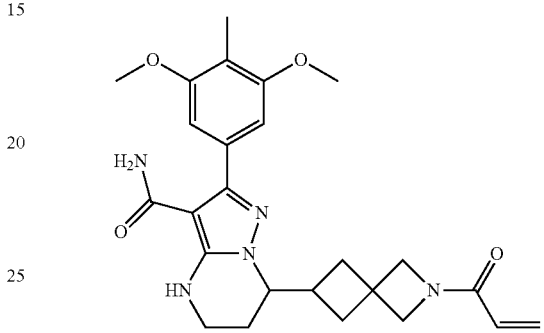

Example H1 was synthesized from 5-amino-3-(3,5-dimethoxy-4-methylphenyl)-1H-pyrazole-4-carbonitrile (intermediate from Example A1) and tert-butyl 6-(3-(dimethylamino)acryloyl)-2-azaspiro[3.3]heptane-2-carboxylate (ref: WO2014173289) following the procedures similar to those in example A2 without the Suzuki reaction step. NaBH$_4$ was used in the reduction step. $^1$H NMR (400 MHz, DMSO-$d_6$) δ 6.71 (s 1H), 6.70 (s 1H), 6.55 (br s, 1H), 6.32-6.18 (m, 1H), 6.10-6.00 (m, 1H), 5.68-5.58 (m, 1H), 4.28-4.23 (m, 1H), 4.15-4.10 (m, 0.5H), 4.08-4.00 (m, 1H), 4.00-3.92 (m, 2H), 3.88-3.82 (m, 0.5H), 3.78 (s, 6H), 3.30-3.17 (m, 2H), 2.32-2.20 (m, 3H), 2.15-2.05 (m, 1H), 2.00-1.90 (m, 2H), 1.80-1.70 (m, 1H). MS (ESI, m/e) [M+1]$^+$ 466.2.

Some compounds in WO2014173289A1 are listed in the Table I.

| Compounds in WO2014173289A1 | Structure | Description |
|---|---|---|
| 167# | ![structure] | No |

-continued

| Compounds in WO2014173289A1 | Structure | Description |
| --- | --- | --- |
| 167* (faster isomer) 167$ (slower isomer) | | Separated from compound 167 in WO2014173289A1 using chiral HPLC |
| 174 | 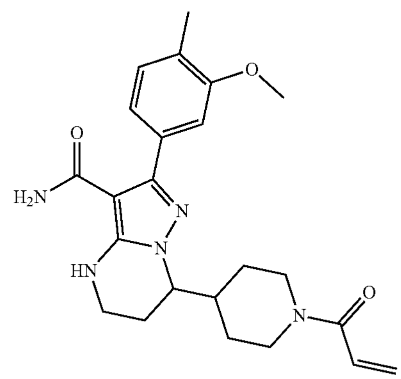 [SMILES: C=CC(=O)N1CCC(C2CCNc3c(C(N)=O)c(-c4ccc(C)c(OC)c4)nn32)CC1] | No |
| Compound in WO2014173289A1 | 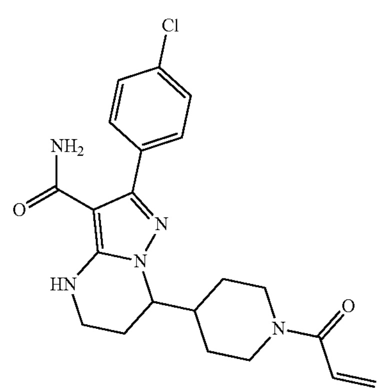 [SMILES: C=CC(=O)N1CCC(C2CCNc3c(C(N)=O)c(-c4ccc(Cl)cc4)nn32)CC1] | No |
| 144 | 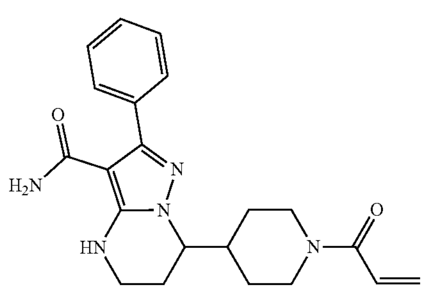 [SMILES: C=CC(=O)N1CCC(C2CCNc3c(C(N)=O)c(-c4ccccc4)nn32)CC1] | No |

-continued
| Compounds in WO2014173289A1 | Structure | Description |
|---|---|---|
| 158 | 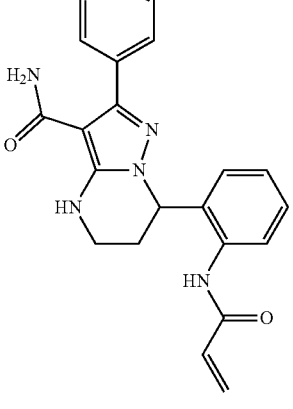 | No |
| 169# | 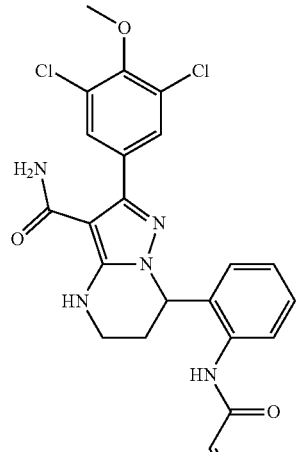 | No |
| 169* (faster isomer) 169$ (slower isomer) | 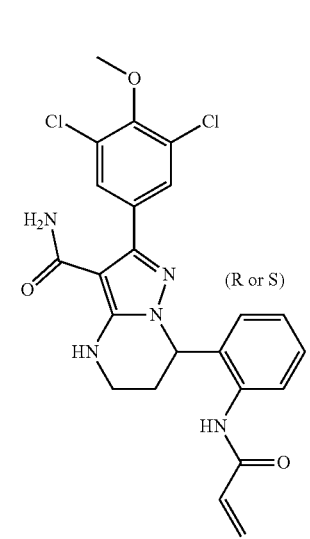 [SMILES: C=CC(=O)Nc1ccccc1C1CCNc2c(C(N)=O)c(-c3cc(Cl)c(OC)c(Cl)c3)nn21] | Separated from compound 169 in WO2014173289A1 using chiral HPLC |

| Compounds in WO2014173289A1 | Structure | Description |
|---|---|---|
| 176 | 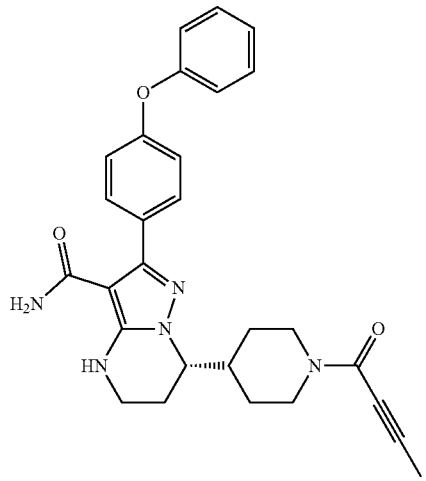 [SMILES: CC#CC(=O)N1CCC([C@@H]2CCNc3c(C(N)=O)c(-c4ccc(Oc5ccccc5)cc4)nn32)CC1] | No |

Btk Kinase Enzymatic Assays

Compounds disclosed herein were tested for inhibition of Btk kinase (aa2-659, Carna Biosciences) in assays based on the time-resolved fluorescence-resonance energy transfer (TR-FRET) methodology. The assays were carried out in 384-well low volume black plates in a reaction mixture containing Btk kinase, 30 μM ATP, 0.4 μM peptide substrate and serially diluted compound in buffer containing 50 mM Tris pH7.4, 10 mM $MgCl_2$, 2 mM $MnCl_2$, 0.1 mM EDTA, 1 mM DTT, 0.005% Tween-20, 20 nM SEB and 0.01% BSA. The kinase was incubated with compound for 60 minutes at room temperature and the reaction was initiated by the addition of ATP and peptide substrate. After reaction at room temperature for 60 minutes, an equal volume of stop/detection solution was added according to the manufacture's instruction (CisBio Bioassays). The stop/detection solution contained $Eu^{3+}$ cryptate-conjugated mouse monoclonal antibody (PT66) anti-phosphotyrosine and XL665-conjugated streptavidin in buffer containing 50 mM HEPES pHn7.0, 800 mM KF, 20 mM EDTA, and 0.1% BSA. Plates were sealed and incubated at room temperature for 1 hour, and the TR-FRET signals (ratio of fluorescence emission at 665 nm over emission at 620 nm with excitation at 337 nm wavelength) were recorded on a PHERAstar FS plate reader (BMG Labtech). Phosphorylation of peptide substrate led to the binding of anti-phosphotyrosine antibody to the biotinylated peptide substrate, which places fluorescent donor ($Eu^{3+}$ crypate) in close proximity to the accepter (Streptavidin-XL665), thus resulting in a high degree of fluorescence resonance energy transfer from the donor fluorophore (at 620 nm) to the acceptor fluorophore (at 665 nm). Inhibition of Btk kinase activity resulted in decrease of the TR-FRET signal. The $IC_{50}$ for each compound was derived from fitting the data to the four-parameter logistic equation by Graphpad Prism software.

Biochemical Kinase Selectivity $IC_{50}$ determination of Tec: The protocol of Tec assay is similar to Btk assay except for the following modifications: 1) 280 μM ATP and 0.083 ug/ml Poly-GT substrate were used in the kinase reaction; 2) the reaction buffer doesn't contain SEB.

$IC_{50}$ determination of EGFR: The protocol of EGFR assay is similar to Btk assay except for the following modifications: 1) 20 μM ATP, 0.72 μM TK substrate-biotin (one universal substrate for tyrosine kinases) and serially diluted compound (the final concentration of 4.76% DMSO) were used in the kinase reaction; 2) the reaction buffer contains 50 mM HEPES pH7.5, 10 mM $MgCl_2$, 1 mM EGTA, 0.01% Brij-35, 2.5 mM DTT and 0.1% BSA; 3) the stop/detection solution buffer contains 25 mM HEPES pH7.38, 400 mM KF, 50 mM EDTA, 0.01% Triton-X100 and 0.1% BSA.

Btk pY223 Cellular Assay

Btk pY223 cellular assay is an HTRF based assay intended to determine the endogenous levels of phosphorylated Btk at Tyr223. Auto-phosphorylation of Tyr223 is necessary for full activation of Btk. The assay is performed using Ramos cells (CRL-1596, ATCC) with a Btk pY223 assay kit (63ADKPEG, Cisbio).

Briefly, Ramos cells were serum starved in 0.5% FBS-containing RPMI1640 overnight. The cells were then incubated with interested compounds at various concentrations in a $CO_2$ incubator for 3 hours. After the incubation, cells were stimulated with 1 mM pervanadate (PV) or $Na_3VO_4$ (OV) for 20 min. Then, the cells were collected and lysed with 1× lysis buffer at RT for 10 min (4× lysis buffer supplied in the kit). 1× antibody mix was prepared by diluting anti-Btk-d2 and anti-pBtk-K in detection buffer (supplied in the kit). 18 μl of cell lysates was transferred to the OptiPlate-384 assay plate (6005620, Perkin Elmer) pre-loaded with 2 μl/well of 1× antibody mixture. After mixing gently and spinning briefly, the plate was sealed up and kept in dark at RT for 18 hours. The fluorescence emission was measured at two different wavelengths (665 nm and 620 nm) on a compatible HTRF reader (PHERAstar FS, BMG). The potency of compounds was calculated based on the inhibition of ratio between signal intensities at 665 nm and 620 nm. IC50 values were calculated with GraphPad Prism software using the sigmoidal dose-response function.

Effects of Compounds on Tumor Cell Proliferation in Rec-1 Haematological Cancer Line MCL cell line (Rec-1) was used in this study. Cells were reinstated from frozen stocks that were laid down within 30 passages from the original purchase. Cells were maintained in RPMI-1640 supplemented with 10% fetal bovine serum/FBS (Thermo Scientific); 100 units/ml penicillin (Gibco) and 0.1 mg/ml streptomycin (Gibco) at 37° C. in a humidified atmosphere of 5% $CO_2$.

The growth-inhibitory activity of compounds in Rec-1 cells was determined using CellTiter-Glo luminescent cell viability assay (Promega). The number of cells seeded per well of a 96-well plate was optimized to ensure logarithmic growth over 6 days treatment period. Cells were treated in triplicate with a 10-point dilution series. Following a 6-day exposure to the compound, 100 ul of cell media were removed and 30 ul of CellTiter-Glo reagent was added into the cell culture. Mixture was agitated on an orbital shaker for 2 minutes to ensure cell lysis, followed by 10 minutes incubation at RT to allow development and stabilization of luminescent signals, which corresponded to quantity of ATP and thus the quantity of metabolically active cells. Luminescent signals were measured using PHERAstar FS reader (BMG). Mean $IC_{50}$ values for cell viability were determined with GraphPad Prism software.

Cellular Btk Occupation Assay

Cellular Btk occupation assay is an ELISA based assay intended to determine the occupation of inhibitor to endogenous Btk. Occupied Btk protein loses its kinase activity and the occupation prevents other inhibitors from binding to the kinase site. The assay was performed using Z-138 cells (CRL-3001, ATCC). The detection probe is developed in-house.

Briefly, Z-138 cells ($1\times10^6$ cells/well) were treated with increasing concentrations of each compound for 3 hours, washed, lysed, and loaded to ELISA plate pre-immobilized with the detection probe. After overnight incubation, the plate was washed with PBST for 3 times. Probe conjugated Btk protein was detected by a Btk antibody (611116, BD) followed by a secondary antibody (w4021, Promega). The potency of compounds was calculated based on the inhibition of ratio between signal intensities at OD450 nm and OD550 nm. IC50 values were calculated with GraphPad Prism software using the sigmoidal dose-response function.

Representative compounds as disclosed herein were tested and found to inhibit kinase Btk, autophosphorylation of Btk at Tyr-223, proliferation in Rec-1 cell line and cellular Btk occupation assay with $IC_{50}$ values ranging from sub-nanomolar to 10 micromolar.

TABLE II

Assay data for representative compounds

| Compound No. | IC50 (nM) | | | | | IC50 (nM) |
|---|---|---|---|---|---|---|
| | Btk | EGFR | Fold of EGFR/Btk | Tec | Fold of Tec/Btk | in cell Btk pY223 |
| A1 | 1.2 | 3326 | 2772 | 253 | 210 | 60 |
| A1a (Faster isomer) | 1.0 | 687 | 687 | 172 | 172 | 17.2 |
| A1b | >100 | ND | ND | ND | ND | ND |
| A2 | 1.3 | >1000 | ND | 180 | 138 | 28 |
| A2a (Faster isomer) | 0.7 | 450 | 643 | 83 | 119 | 7.0 |
| A2b (Slower isomer) | 94.3 | ND | ND | ND | ND | ND |
| A3 | 1.5 | >1000 | ND | 134 | 89 | 29.1 |
| A4 | 0.97 | >1000 | ND | 50 | 52 | 20 |
| A5 | 1.2 | >1000 | ND | 145 | 121 | 21.3 |
| A6 | 1.1 | 1999 | 1817 | 359 | 326 | 33.5 |
| A6a (Faster isomer) | 0.57 | 1092 | 1915 | 98 | 172 | 10.8 |
| A6b | 41 | ND | ND | ND | ND | ND |
| A7 | 4.1 | 1186 | 289 | 254 | 62 | 148.2 |
| A8 | 0.93 | 1382 | 1486 | 130 | 140 | 14.8 |
| A9 | 41 | ND | ND | ND | ND | ND |
| A10 | 51 | ND | ND | ND | ND | ND |
| A11 | 1.9 | 1846 | 972 | 271 | 143 | 39 |
| A11a | 108 | ND | ND | ND | ND | ND |
| A11b | 1.1 | ND | ND | ND | ND | ND |
| A12 | 4.7 | >10000 | ND | 289 | 61 | 37.3 |
| A13 | >100 | ND | ND | ND | ND | ND |
| A14 | 15 | ND | ND | >1000 | ND | ND |
| A15 | 20 | ND | ND | 1002 | 50 | ND |
| A16 | 7.1 | 2367 | 333 | 556 | 78 | ND |
| A17 | 2.0 | 713 | 356 | 189 | 94.5 | 136.2 |
| A18 | 2.0 | 603 | 302 | 297 | 149 | 74.8 |
| A19 | 7.2 | >10000 | ND | 455 | 63.2 | ND |
| A20 | 3.3 | 496 | 150 | 352 | 107 | 142.6 |
| A21 | 21 | ND | ND | ND | ND | ND |
| A22 | 2.3 | 1760 | 765 | 551 | 240 | 54.2 |
| A23 | 1.2 | 656 | 547 | 107 | 89 | 28.2 |
| A24 | 28 | ND | ND | ND | ND | ND |
| A25 | 23 | ND | ND | >1000 | ND | ND |
| A26 | 41 | ND | ND | ND | ND | ND |
| A27 | 18 | ND | ND | >1000 | ND | ND |
| A28 | 16 | ND | ND | 369 | 23 | ND |
| A29 | 16 | ND | ND | >1000 | ND | ND |
| A30 | 53 | ND | ND | >1000 | ND | ND |
| A31 | >100 | ND | ND | ND | ND | ND |
| A32 | 52 | ND | ND | ND | ND | ND |
| A33 | 2.7 | 9394 | 3479 | 499 | 185 | 42.9 |
| A34 | 1.8 | 405 | 225 | 207 | 115 | 41.8 |
| A35 | 2.3 | 1149 | 500 | 174 | 75.6 | 65 |

TABLE II-continued

Assay data for representative compounds

| Compound No. | Btk | EGFR | IC50 (nM) Fold of EGFR/Btk | Tec | Fold of Tec/Btk | IC50 (nM) in cell Btk pY223 |
|---|---|---|---|---|---|---|
| A36 | 1.1 | 2573 | 2339 | 137 | 125 | 50.5 |
| A37 | 1.5 | 4496 | 2997 | 50 | 33 | 49.4 |
| A38 | 2.8 | 2249 | 803 | 264 | 94 | 36.7 |
| A39 | 6.8 | 6082 | 894 | 102 | 15 | ND |
| A40 | 11 | ND | ND | 253 | 23 | ND |
| A41 | 3.3 | 1513 | 458 | 101 | 31 | 66.8 |
| A42 | 3.0 | 2005 | 668 | 53 | 18 | ND |
| A43 | 6.8 | 6181 | 909 | 39 | 5.7 | ND |
| A44 | 4.9 | 3171 | 647 | 35 | 7.1 | ND |
| A45 | 4.4 | >10000 | ND | 362 | 82 | ND |
| A46 | 5.9 | 3813 | 646 | 974 | 165 | 257.5 |
| A47 | 17 | ND | ND | ND | ND | ND |
| A48 | 16 | ND | ND | ND | ND | ND |
| A49 | 18 | ND | ND | ND | ND | ND |
| A50 | 0.34 | 599 | 1762 | 3.2 | 9.4 | 12.3 |
| A51 | ND | ND | ND | 136 | ND | ND |
| A52 | 1.3 | ND | ND | ND | ND | ND |
| A52a | 0.7 | ND | ND | ND | ND | ND |
| A52b | 39.9 | ND | ND | ND | ND | ND |
| B1 | 13 | ND | ND | ND | ND | ND |
| B2 | 5.0 | 1752 | 350 | 172 | 34 | 45.7 |
| B3 | 5.9 | 1913 | 324 | 157 | 27 | 93.1 |
| C1 | 3.4 | 536 | 158 | 380 | 112 | 49.6 |
| C2 | 34 | ND | ND | ND | ND | ND |
| D1 | 10 | ND | ND | ND | ND | ND |
| D2 | 63 | ND | ND | >1000 | ND | ND |
| E1 | 33 | ND | ND | ND | ND | ND |
| F1 | >100 | ND | ND | ND | ND | ND |
| G1 | 12 | ND | ND | ND | ND | ND |
| H1 | 35 | ND | ND | ND | ND | ND |
| 167[#] | 2.4 | 9.5 | 4 | ND | ND | ND |
| 167* (faster isomer) | 1.0 | 14 | 14 | 157 | 157 | 83.5 |
| 167[$] (slower isomer) | >100 | ND | ND | ND | ND | ND |
| 174 | 4.8 | 281 | 58.5 | 64 | 13 | ND |
|  | 22 | ND | ND | ND | ND | ND |

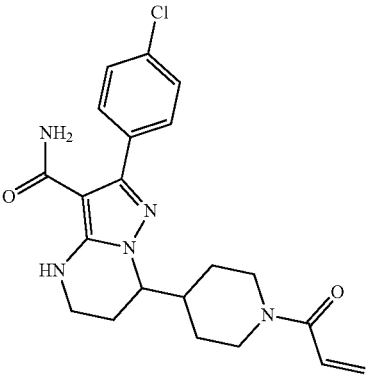 [SMILES: C=CC(=O)N1CCC(C2CCNc3c(C(N)=O)c(-c4ccc(Cl)cc4)nn32)CC1]

in WO2014173289A1

| 144 | 140 | ND | ND | 491 | 3.5 | ND |
| 158 | 2.9 | 0.49 | 0.2 | 56 | 19 | ND |
| 169[#] | 0.15 | 0.54 | 3.6 | ND | ND | ND |
| 169* (faster isomer) | 0.46 | 1.0 | 2.2 | 37 | 80 | 28.2 |
| 169[$] (slower isomer) | >100 | ND | ND | ND | ND | ND |

ND—no data

TABLE III
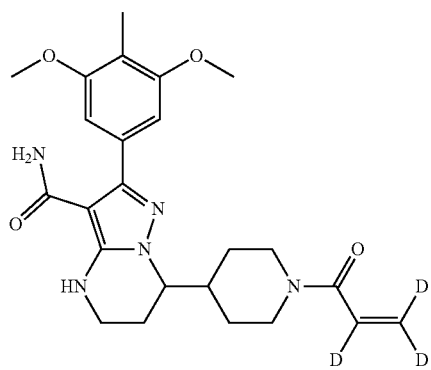 [SMILES: [2H]C([2H])=C([2H])C(=O)N1CCC(C2CCNc3c(C(N)=O)c(-c4cc(OC)c(C)c(OC)c4)nn32)CC1]
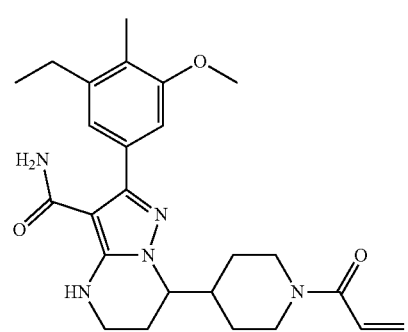 [SMILES: C=CC(=O)N1CCC(C2CCNc3c(C(N)=O)c(-c4cc(CC)c(C)c(OC)c4)nn32)CC1]
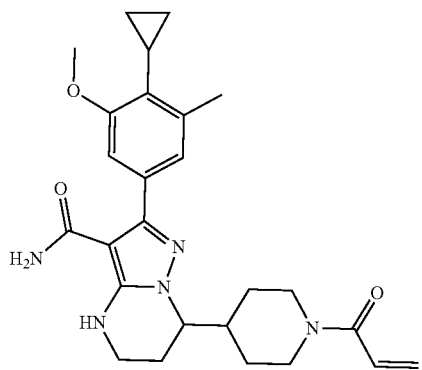 [SMILES: C=CC(=O)N1CCC(C2CCNc3c(C(N)=O)c(-c4cc(C)c(C5CC5)c(OC)c4)nn32)CC1]
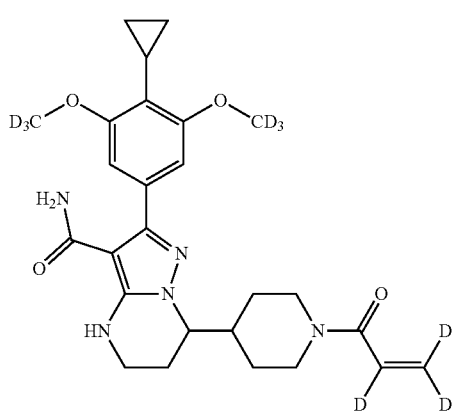 [SMILES: [2H]C([2H])=C([2H])C(=O)N1CCC(C2CCNc3c(C(N)=O)c(-c4cc(OC([2H])([2H])[2H])c(C5CC5)c(OC([2H])([2H])[2H])c4)nn32)CC1]
TABLE III-continued
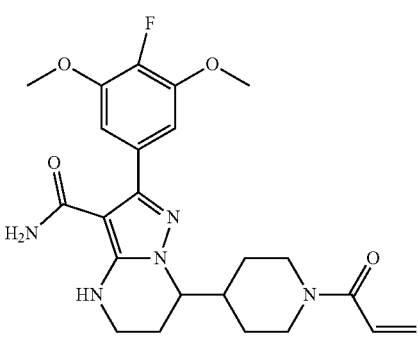 [SMILES: C=CC(=O)N1CCC(C2CCNc3c(C(N)=O)c(-c4cc(OC)c(F)c(OC)c4)nn32)CC1]
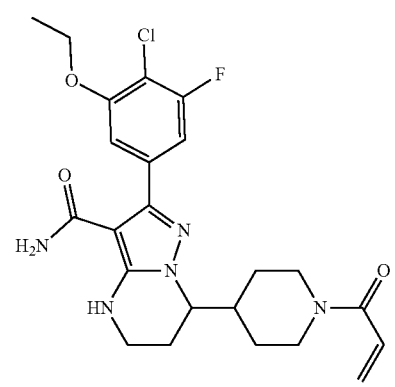 [SMILES: C=CC(=O)N1CCC(C2CCNc3c(C(N)=O)c(-c4cc(F)c(Cl)c(OCC)c4)nn32)CC1]
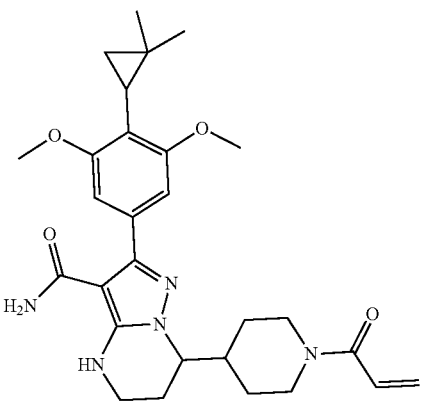 [SMILES: C=CC(=O)N1CCC(C2CCNc3c(C(N)=O)c(-c4cc(OC)c(C5CC5(C)C)c(OC)c4)nn32)CC1]
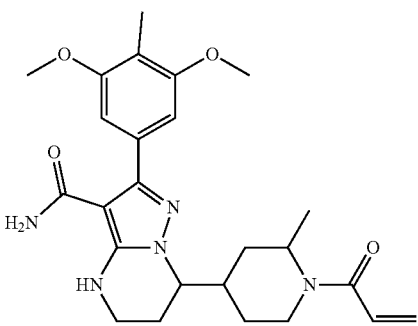 [SMILES: C=CC(=O)N1CCC(C2CCNc3c(C(N)=O)c(-c4cc(OC)c(C)c(OC)c4)nn32)CC1C]

TABLE III-continued

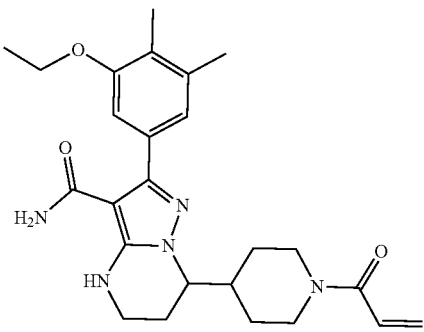 [SMILES: C=CC(=O)N1CCC(C2CCNc3c(C(N)=O)c(-c4cc(C)c(C)c(OCC)c4)nn32)CC1]

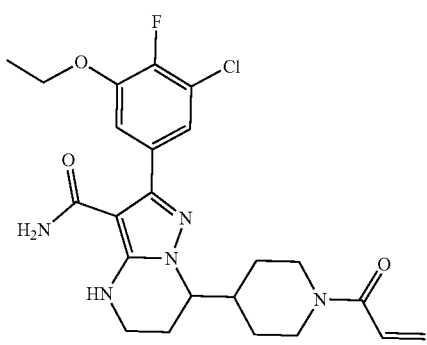 [SMILES: C=CC(=O)N1CCC(C2CCNc3c(C(N)=O)c(-c4cc(Cl)c(F)c(OCC)c4)nn32)CC1]

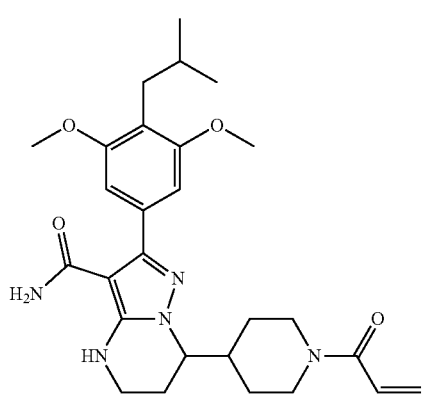 [SMILES: C=CC(=O)N1CCC(C2CCNc3c(C(N)=O)c(-c4cc(OC)c(CC(C)C)c(OC)c4)nn32)CC1]

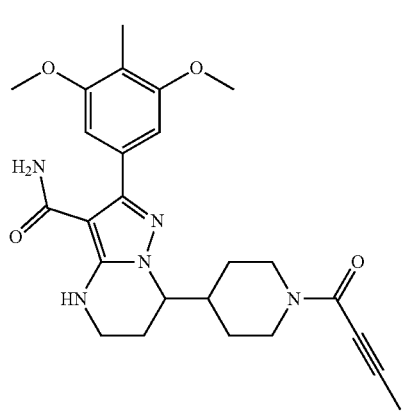 [SMILES: CC#CC(=O)N1CCC(C2CCNc3c(C(N)=O)c(-c4cc(OC)c(C)c(OC)c4)nn32)CC1]

TABLE III-continued

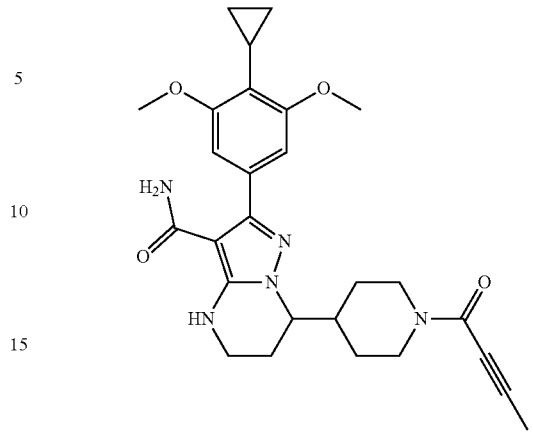

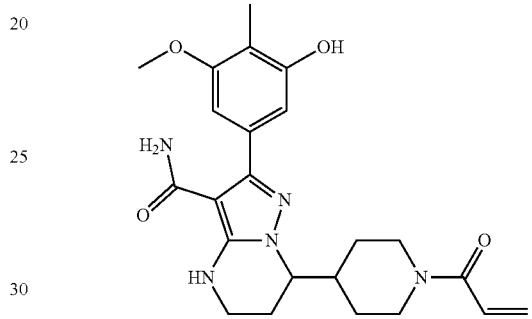

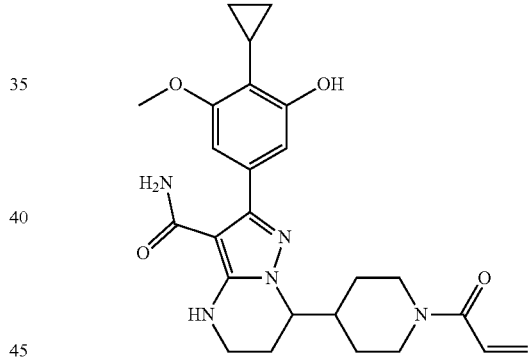

The examples of the present invention and compounds disclosed in WO2014173289A1 were tested in in biochemical assay, cellular assay, pharmacodynamic evaluation in mice and pharmacokinetic evaluation in rat. The results are shown in Tables II, IV and FIG. 1A to 2B. Table II surprisingly demonstrates these compounds having high affinity for Btk and comparatively less affinity for both Tec and EGFR (>100 fold selectivity), for example compounds A1a, A2a, A5, A6a, A8, A11, A18, A20, A22, A33, A34, A36, A46 and C1, most of which have been found to have a specific combination of a tri-substituted phenyl ring and a piperidine ring (particularly N-substituted acryloyl piperidine ring) in the molecule.

To the contrast, Compounds 167 # or 167* and 169 # or 169*, disclosed in WO2014173289A1, also bears a tri-substituted phenyl ring (with substituent $R^1$ is methoxy) in combination with another phenyl ring on the right side. These compounds do exhibit high or comparable inhibitory activity against Btk, and exhibit good selectivity of Btk over Tec. However, they showed poor selectivity of Btk against EGFR, lower cellular potency, pharmacodynamic property and oral bioavailability. Compound 174 in WO2014173289A1 having a combination of di-substituents on the top phenyl ring and a piperidine ring on the right side showed low affinity for Btk and almost no selectivity against Tec.

Starting from Compounds 167 and 169 in WO2014173289A1, the inventors also prepared two analogs A14 and A15 which have a different combination of a tri-substituted phenyl ring and a piperidine ring in the molecule. However, both compounds showed poor affinity for Btk as shown in Table II of the present specification.

In Vivo Mice PD Assay

ICR mice were randomly assigned into different groups with 4 mice per group. Mice were treated with different dose levels of compounds as indicated and euthanized using carbon dioxide at 4 hrs after dosing. Treatments were administered by oral gavage (p.o.). For peripheral blood mononuclear cell (PBMC) and spleen preparation, mouse spleens were collected from euthanized mice and grinded in protein lysis buffer. Mouse blood was lysed with protein lysis buffer. Samples were centrifuged at 4° C. for 15 minutes. Supernatant was transferred to a fresh tube and protein concentration was determined using BCA protein analysis. Ninety-six well plates was coated with neutravidin and incubated with a biotinylated probe. Cell lysates or recombinant human Btk protein samples were added and the plates were incubated at 4° C. overnight. Plates were washed with PBST and blocked with blocking buffer for 1 hr. Primary anti-Btk rabbit polyclonal antibody was added and incubated for 2 hrs and secondary anti-rabbit-HRP antibody was added and incubated for 1 hr. Following standard ELISA protocols using TMB as substrate, OD450 nm was read using microplate reader. The amount of unoccupied Btk proteins in PBMC or spleen lysates was calculated based on the standard curve and presented as percentage of that of vehicle-treated animals.

Result

The PD activity of compounds A1a, A2a, A6a, 167* and 169* was assessed by Btk occupancy assay compared to compound 176, which is designed based on direct quantification of the covalent bonding to Btk protein after drug exposure. As shown in FIGS. 1A and 1B, A1a and A2a were more potent than 176 in both of PBMC and spleen. A6a showed similar activity with that of 176. However, 167* and 169* were 2~3 fold less potent when compared with 176 in both of PBMC and spleen (FIGS. 2A and 2B).

Rat Pharmacokinetic Study 8 weeks old Male Sprague Dawley rats with jugular vein catheter were purchased from SKILLS Model Animal Research Technology Co., Ltd. (Beijing, China). All procedures involving animals were conducted in accordance with the Institutional Animal Care and Use Committee (IACUC) of BeiGene. Compound was dissolved in 32% DMA, 36% ethanol, and 32% propylene glycol for intravenous (IV) injection, and was suspended in 0.5% (w/v) methylcellulose (MC) solution for oral gavage (PO). The rats were fasted overnight prior to the treatment until 4 hours post-dose, and divided into two groups for 3 animals in each group. The first group was given a single IV injection of compound at 1 mg·kg$^{-1}$ via tail vein. Blood samples (~0.15 mL) were collected at Pre-dose, 5, 15, 30 min, 1, 2, 4, 8, and 24 h post-dose via jugular vein cannula into EDTA-coagulated tubes. The second group was given a single PO administration at 5 mg·kg$^{1}$, respectively. Blood samples were collected at Pre-dose, 15, 30 min, 1, 2, 4, 8, and 24 h post-dose. All whole blood was processed for plasma by centrifugation at 3000 g for 10 min. Plasma samples were collected and kept below −30° C. The concentration of compound in plasma was determined by LC-MS/MS method.

Result

In the rat PK study as shown in Table IV, A1a, A2a and A11b exhibited lower plasma clearance values, higher Cmax, AUC and oral bioavailability compared to compound 167*.

TABLE IV

Rat PK results

| Compound | Cl (mL/min/kg) | Cmax (ng/mL) | AUC$_{0-inf}$ (h · ng · mL$^{-1}$) | F (%) |
|---|---|---|---|---|
| A1a (Faster isomer) | 24.4 | 667 | 964 | 26.4 |
| A11b | 13.7 | 2250 | 4799 | 69.5 |
| A2a (Faster isomer) | 42.8 | 859 | 1710 | 73.7 |
| 167* | 151.6 | 60.4 | 65.1 | 11.8 |

What is claimed is:
1. A compound of formula (I):

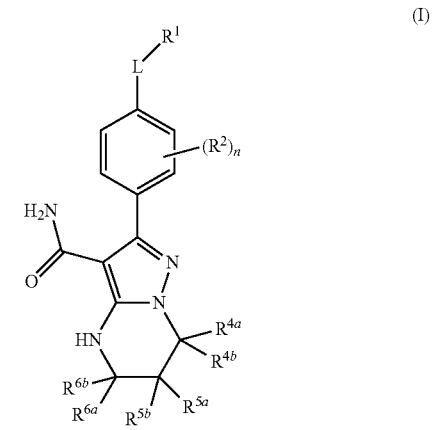

or a stereoisomer thereof, or a pharmaceutically acceptable salt thereof, wherein:
L is a bond, CH$_2$, NR$^{12}$, O, or S;
R$^1$ is halogen, heteroalkyl, alkyl, alkenyl, cycloalkyl, aryl, saturated or unsaturated heterocyclyl, heteroaryl, alkynyl, —CN, —NR$^{13}$R$^{14}$, —OR$^{13}$, —COR$^{13}$, —CO$_2$R$^{13}$, —CONR$^{13}$R$^{14}$, —C(=NR$^{13}$)NR$^{14}$R$^{15}$, —NR$^{13}$COR$^{14}$, —NR$^{13}$CONR$^{14}$R$^{15}$, —NR$^{13}$CO$_2$R$^{14}$, —SO$_2$R$^{13}$, —NR$^{13}$SO$_2$NR$^{14}$R$^{15}$, or —NR$^{13}$SO$_2$R$^{14}$, wherein the alkyl, alkenyl, alkynyl, cycloalkyl, heteroaryl, aryl, and saturated or unsaturated heterocyclyl are optionally substituted with at least one substituent R$^{16}$;
n is an integer of 2, 3 or 4;
each R$^2$ is independently halogen, alkyl, —S-alkyl, —CN, —NR$^{13}$R$^{14}$, —OR$^{13}$, —COR$^{13}$, —CO$_2$R$^{13}$, —CONR$^{13}$R$^{14}$, —C(=NR$^{13}$)NR$^{14}$R$^{15}$, —NR$^{13}$COR$^{14}$, —NR$^{13}$CONR$^{14}$R$^{15}$, —NR$^{13}$CO$_2$R$^{14}$, —SO$_2$R$^{13}$, —NR$^{13}$SO$_2$NR$^{14}$R$^{15}$, or —NR$^{13}$SO$_2$R$^{14}$, wherein R$^2$ is, optionally, partially or fully deuterated;
R$^{4a}$ and R$^{4b}$ are each independently hydrogen, halogen, heteroalkyl, alkyl, alkenyl, cycloalkyl, saturated or unsaturated heterocyclyl, heteroaryl, alkynyl, —CN, —NR$^{13}$R$^{14}$, —OR$^{13}$, —COR$^{13}$, —CO$_2$R$^{13}$, —CONR$^{13}$R$^{14}$, —C(=NR$^{13}$)NR$^{14}$R$^{15}$, —NR$^{13}$COR$^{14}$, —NR$^{13}$CONR$^{14}$R$^{15}$, —NR$^{13}$CO$_2$R$^{14}$, —SO$_2$R$^{13}$, —NR$^{13}$SO$_2$NR$^{14}$R$^{15}$, or —NR$^{13}$SO$_2$R$^{14}$, wherein the alkyl, alkenyl, alkynyl, cycloalkyl, heteroaryl, aryl, and saturated or unsaturated heterocyclyl are optionally substituted with at least one substituent R$^{16}$;

R$^{5a}$ and R$^{5b}$ are each independently hydrogen, halogen, heteroalkyl, alkyl, alkenyl, cycloalkyl, aryl, saturated or unsaturated heterocyclyl, heteroaryl, alkynyl, —CN, —NR$^{13}$R$^{14}$, —OR$^{13}$, —COR$^{13}$, —CO$_2$R$^{13}$, —CONR$^{13}$R$^{14}$, —C(=NR$^{13}$)NR$^{14}$R$^{15}$, —NR$^{13}$COR$^{14}$, —NR$^{13}$CONR$^{14}$R$^{15}$, —NR$^{13}$CO$_2$R$^{14}$, —SO$_2$R$^{13}$, —NR$^{13}$SO$_2$NR$^{14}$R$^{15}$, or —NR$^{13}$SO$_2$R$^{14}$, wherein the alkyl, alkenyl, alkynyl, cycloalkyl, heteroaryl, aryl, and saturated or unsaturated heterocyclyl are optionally substituted with at least one substituent R$^{16}$;

R$^{6a}$ and R$^{6b}$ are each independently hydrogen, halogen, heteroalkyl, alkyl, alkenyl, cycloalkyl, aryl, saturated or unsaturated heterocyclyl, heteroaryl, alkynyl, —CN, —NR$^{13}$R$^{14}$, —OR$^{13}$, —COR$^{13}$, —CO$_2$R$^{13}$, —CONR$^{13}$R$^{14}$, —C(=NR$^{13}$)NR$^{14}$R$^{15}$, —NR$^{13}$COR$^{14}$, —NR$^{13}$CONR$^{14}$R$^{15}$, —NR$^{13}$CO$_2$R$^{14}$, —SO$_2$R$^{13}$, —NR$^{13}$SO$_2$NR$^{14}$R$^{15}$, or —NR$^{13}$SO$_2$R$^{14}$, wherein the alkyl, alkenyl, alkynyl, cycloalkyl, heteroaryl, aryl, and saturated or unsaturated heterocyclyl are optionally substituted with at least one substituent R$^{16}$; or wherein (R$^{4a}$ and R$^{5a}$), or (R$^{4a}$ and R$^{5b}$), or (R$^{4b}$ and R$^{5a}$), or (R$^{4a}$ and R$^{5b}$), or (R$^{5a}$ and R$^{6a}$), or (R$^{5a}$ and R$^{6b}$), or (R$^{5b}$ and R$^{6a}$), or (R$^{5b}$ and R$^{6b}$), together with the atoms to which they are attached, may form a fused ring selected from cycloalkyl, saturated or unsaturated heterocycle, aryl, and heteroaryl rings, optionally substituted with at least one substituent R$^{16}$;

R$^{12}$ is H or alkyl;

R$^{13}$, R$^{14}$ and R$^{15}$ are each independently H, heteroalkyl, alkyl, alkenyl, alkynyl, cycloalkyl, saturated or unsaturated heterocyclyl, aryl, or heteroaryl; wherein (R$^{13}$ and R$^{14}$), and/or (R$^{14}$ and R$^{15}$) together with the atom(s) to which they are attached, each can form a ring selected from cycloalkyl, saturated or unsaturated heterocycle, aryl, and heteroaryl rings optionally substituted with at least one substituent R$^{16}$; and R$^{16}$ is halogen, substituted or unsubstituted alkyl, substituted or unsubstituted alkenyl, substituted or unsubstituted alkynyl, substituted or unsubstituted cycloalkyl, substituted or unsubstituted aryl, substituted or unsubstituted heteroaryl, substituted or unsubstituted heterocyclyl, oxo, —CN, —OR$^a$, —NR$^a$R$^b$, —COR$^a$, —CO$_2$R$^a$, —CONR$^a$R$^b$, —C(=NR$^a$)NR$^b$R$^c$, —NR$^a$COR$^b$, —NR$^a$CONR$^a$R$^b$, —NR$^a$CO$_2$R$^b$, —SO$_2$R$^a$, —SO$_2$aryl, —NR$^a$SO$_2$NR$^b$R$^c$, or —NR$^a$SO$_2$R$^b$, wherein R$^a$, R$^b$, and R$^c$ are independently hydrogen, halogen, substituted or unsubstituted alkyl, substituted or unsubstituted alkenyl, substituted or unsubstituted alkynyl, substituted or unsubstituted cycloalkyl, substituted or unsubstituted aryl, substituted or unsubstituted heteroaryl, substituted or unsubstituted heterocyclyl, wherein (R$^a$ and R$^b$), and/or (R$^a$ and R$^b$) together with the atoms to which they are attached, can form a ring selected from cycloalkyl, saturated or unsaturated heterocycle, aryl, and heteroaryl rings.

2. The compound of claim 1, wherein L is a bond.

3. The compound of claim 1, wherein R$^1$ is halogen, alkyl, alkenyl, cycloalkyl, aryl, saturated heterocyclyl, heteroaryl, or —OR$^{13}$, wherein the alkyl, alkenyl, cycloalkyl, and heteroaryl are optionally substituted with at least one substituent R$^{16}$.

4. The compound of claim 1, wherein n is 2.

5. The compound of claim 4, wherein one of R$^2$ is at position 3 of the phenyl ring, and the other R$^2$ is at position 5 of the phenyl ring, wherein R$^2$ is optionally partially or fully deuterated.

6. The compound of claim 5, wherein R$^2$, at each of its occurrence, is halogen, alkyl or —O-alkyl, wherein the alkyl group or moiety is optionally partially or fully deuterated.

7. The compound of claim 1, wherein R$^{4a}$, R$^{5a}$, R$^{5b}$, R$^{6a}$ and R$^{6b}$ are hydrogen; and R$^{4b}$ is alkyl, or saturated heterocyclyl, wherein the alkyl and saturated heterocyclyl are optionally substituted with at least one substituent R$^{16}$.

8. The compound of claim 7, wherein R$^{4a}$, R$^{5a}$, R$^{5b}$, R$^{6a}$ and R$^{6b}$ are hydrogen; and R$^{4b}$ is a saturated heterocyclyl containing a nitrogen atom which is optionally substituted with acryloyl or propiolyl.

9. The compound of claim 8, wherein the saturated heterocyclyl in the definition of R$^{4b}$ is a monocyclic ring selected from a azetidine, pyrrole, piperidine, azapane or azocane ring; or a spiro or bridged bicyclic ring selected from azabicyclooctanyl, azaspirononanyl or azaspiroheptanyl.

10. The compound of claim 1, wherein (R$^{4a}$ and R$^{5a}$), or (R$^{4a}$ and R$^{5b}$) or (R$^{4b}$ and R$^{5a}$), or (R$^{4b}$ and R$^{5b}$), or (R$^{5a}$ and R$^{6a}$), or (R$^{5a}$ and R$^{6b}$), or (R$^{5b}$ and R$^{6a}$), or (R$^{5b}$ and R$^{6b}$), together with the atoms to which they are attached, form a fused ring selected from cycloalkyl, saturated or unsaturated heterocycle, aryl, and heteroaryl rings, optionally substituted with at least one substituent R$^{16}$.

11. The compound of claim 10, wherein the fused saturated or unsaturated heterocycle ring is a azetidine, pyrrole, piperidine, azapane or azocane ring optionally substituted with a substituent R$^{16}$ at the nitrogen atom of the fused ring, wherein the substituent R$^{16}$ is acryloyl or propiolyl.

12. A compound of formula (II):

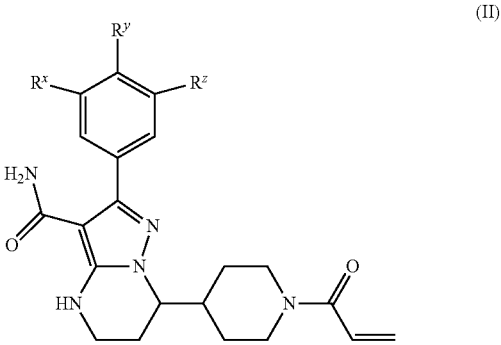

or a stereoisomer thereof, or a pharmaceutically acceptable salt thereof, wherein:

R$^x$ is halogen, alkyl, or —O-alkyl, wherein the alkyl group or moiety is optionally partially or fully deuterated;

R$^y$ is halogen, alkyl optionally substituted with at least substituents selected from hydroxy, halogen, or cycloalkyl; and R$^z$ is halogen, alkyl, or —O-alkyl, wherein the alkyl group or moiety is optionally partially or fully deuterated.

13. The compound of claim 12, wherein
R$^x$ is methoxy, ethoxy, methyl, ethyl or chloro, wherein the methoxy, ethoxy, methyl, ethyl is optionally partially or fully deuterated;
R$^y$ is 2-hydroxylethyl, trifluoromethyl, isopropyl, cyclopropyl, methyl, chloro, bromo, or iodo; and
R$^z$ is methoxy, methyl, or chloro, wherein the methoxy or methyl is optionally partially or fully deuterated.

14. The compound of claim 12, wherein
R$^x$ is methoxy, ethoxy, methyl, chloro, CD$_3$, —CD$_2$CD$_3$, OCD$_3$, or —O—CD$_2$CD$_3$;
R$^y$ is 2-hydroxylethyl, CF$_3$, isopropyl, cyclopropyl, methyl, chloro, bromo, or iodo; and
R$^z$ is ethoxy, methoxy, methyl, ethyl, chloro, or CD$_3$, —CD$_2$CD$_3$, OCD$_3$, or —O—CD$_2$CD$_3$.

15. The compound of claim 12, wherein
R$^x$ is methoxy, ethoxy, methyl, ethyl, chloro, or OCD$_3$;
R$^y$ is 2-hydroxylethyl, CF$_3$, isopropyl, cyclopropyl, methyl, chloro, bromo, or iodo; and
R$^z$ is methoxy, methyl, chloro, or OCD$_3$.

16. The compound of claim 12, wherein the compound is in (S)-configuration of the following formula:

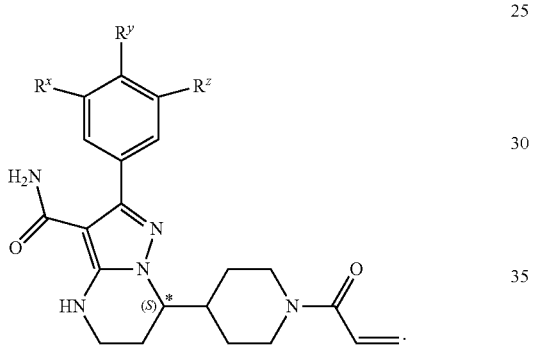

17. The compound of claim 1, which is selected from:

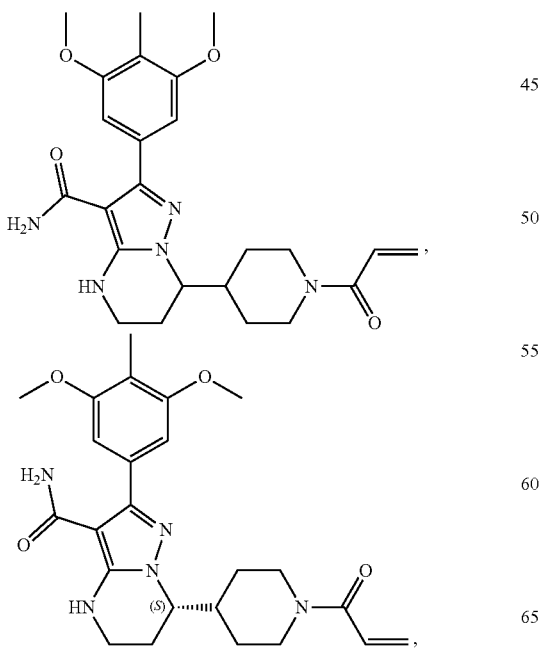

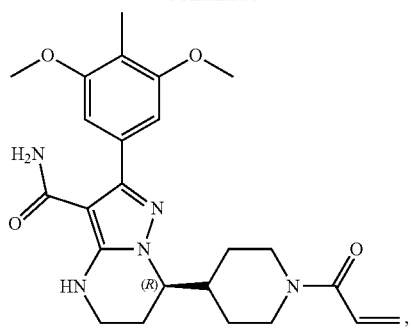

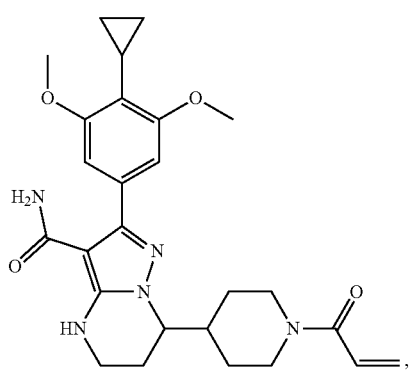

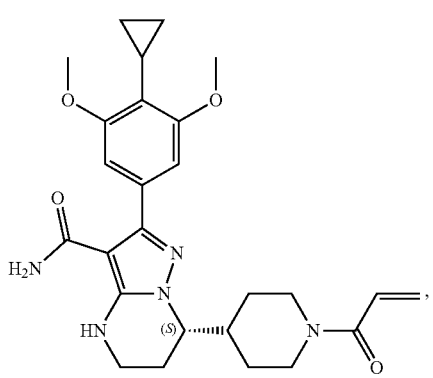

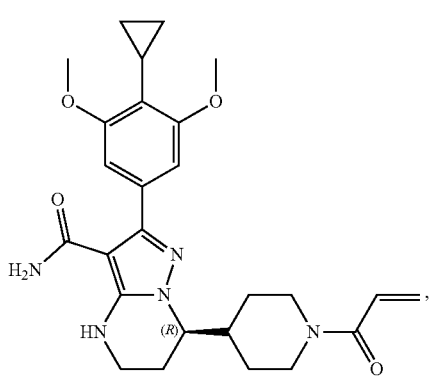

113
-continued
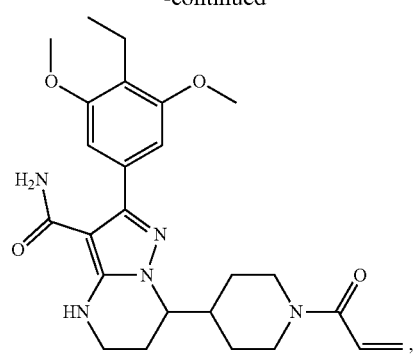
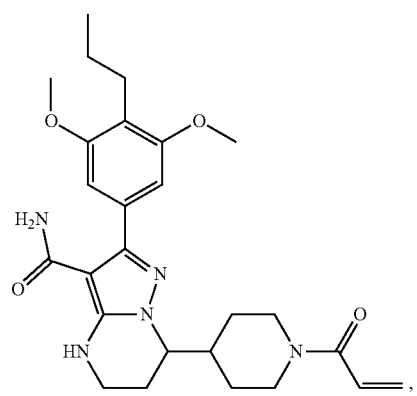
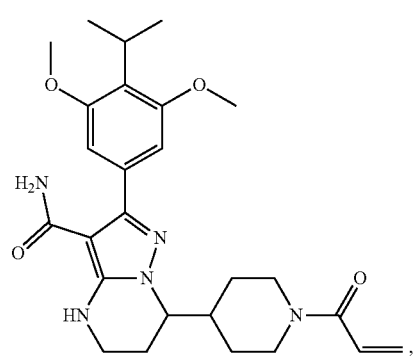
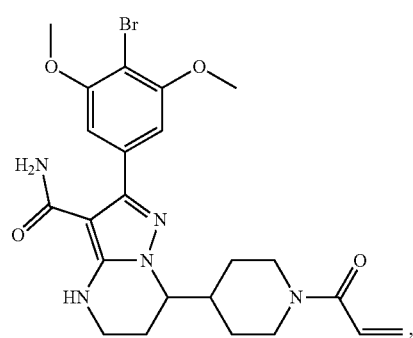
114
-continued
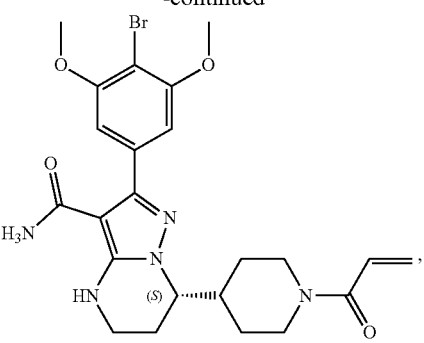
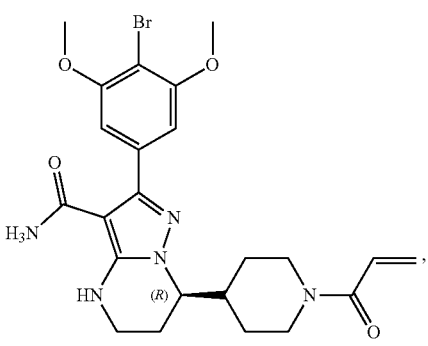
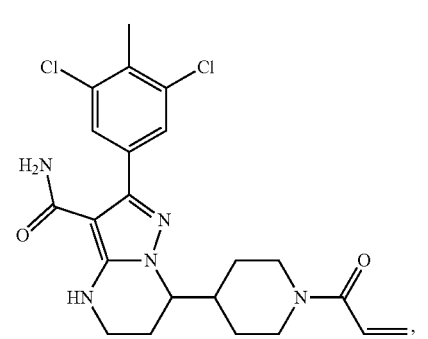
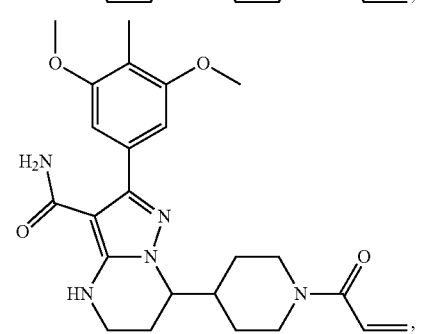
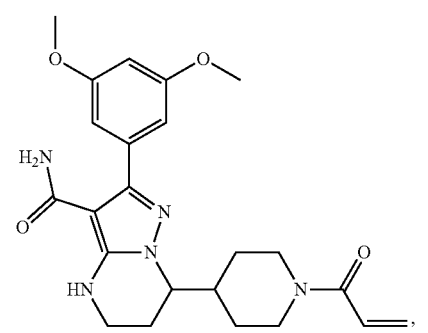

115
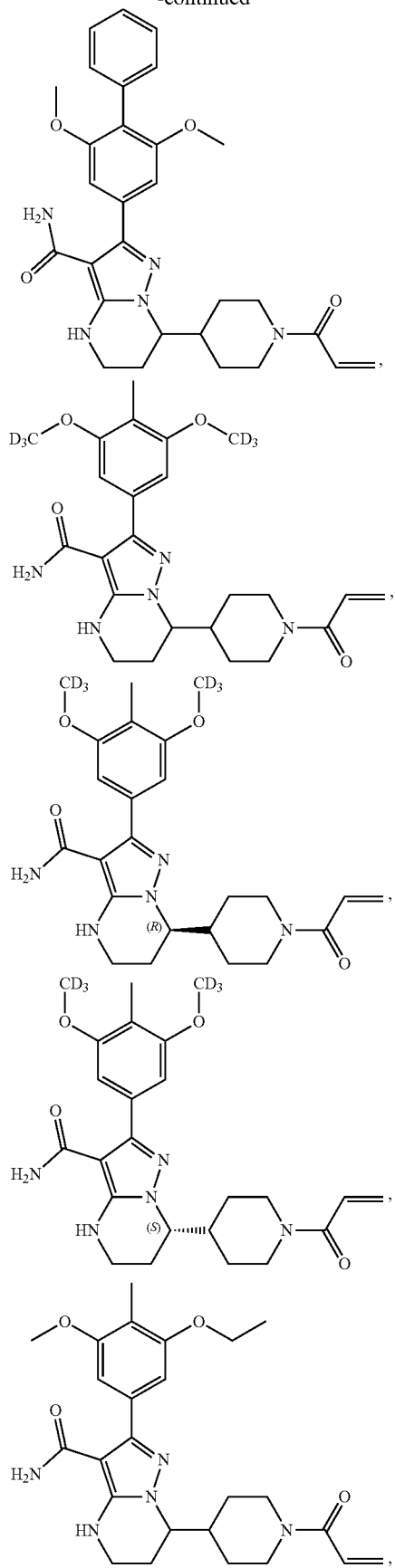
116
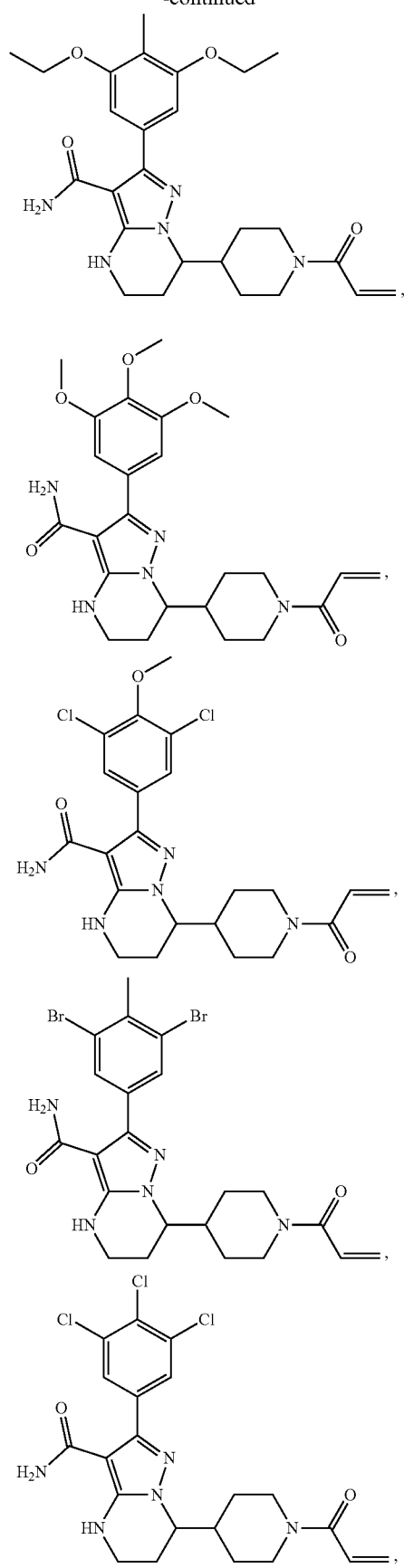

117
-continued
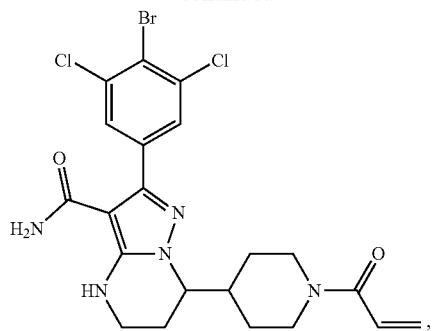
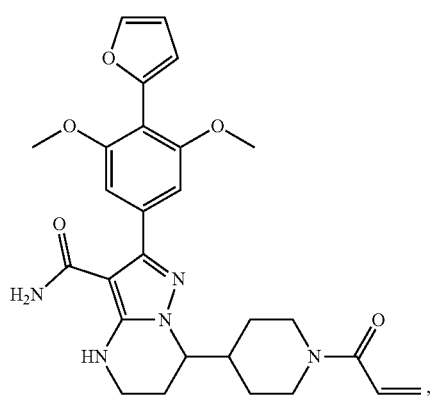
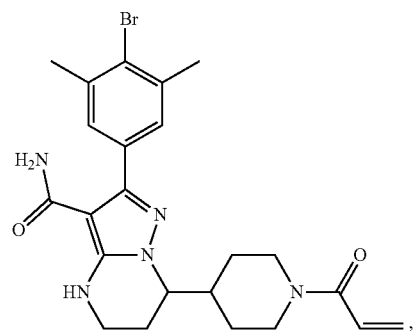
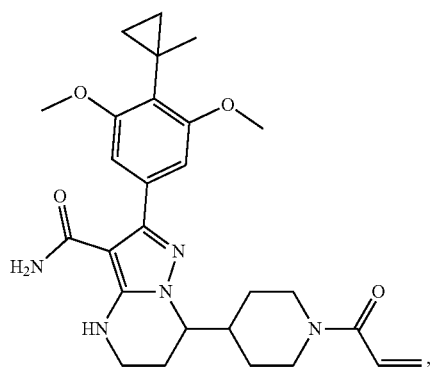
118
-continued
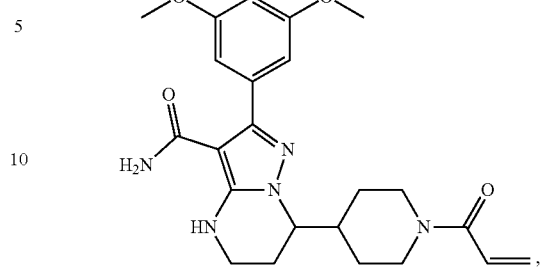
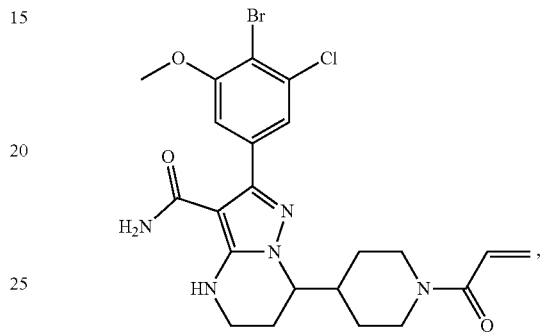
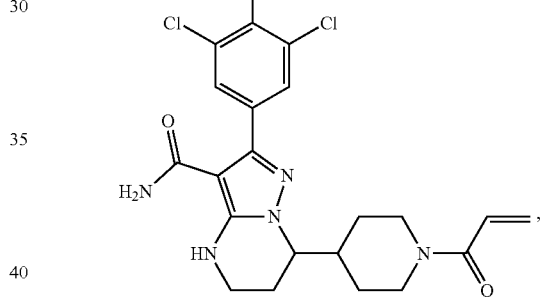
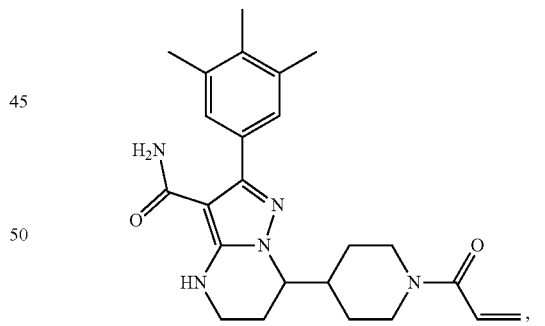
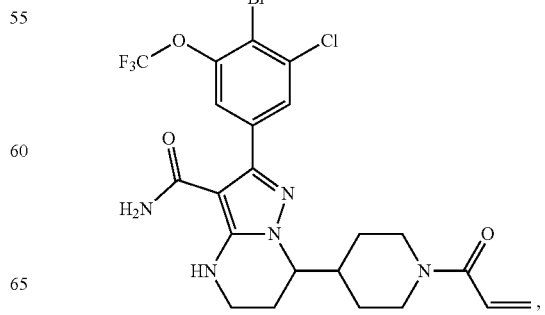

119
-continued
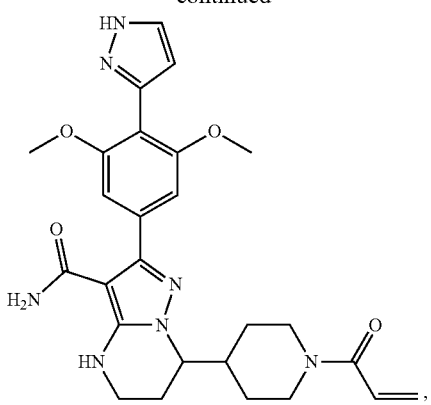
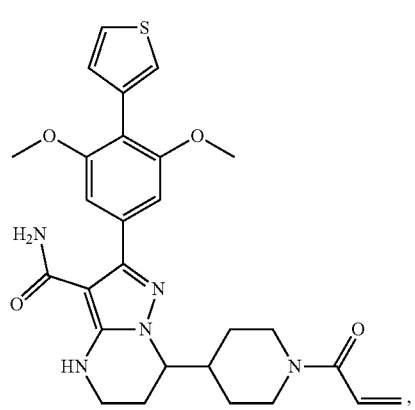
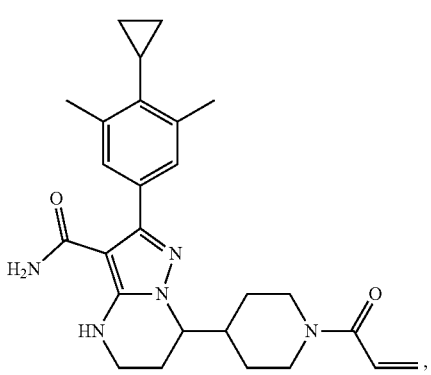
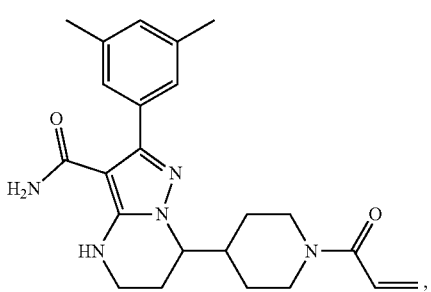
120
-continued
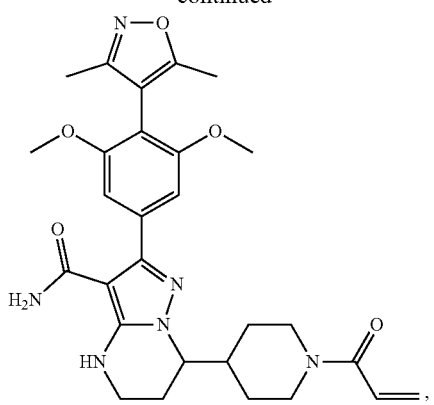
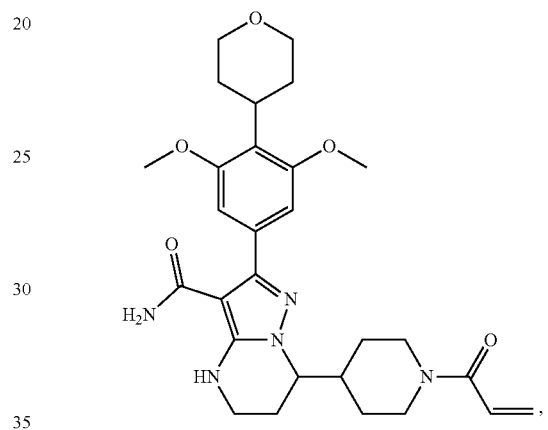
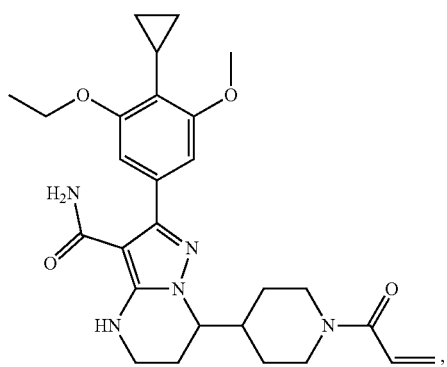
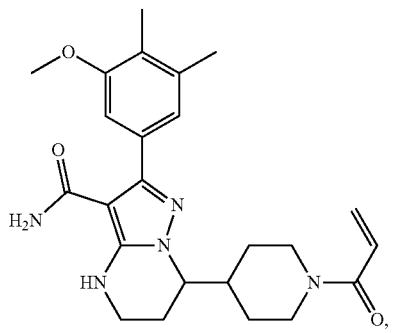

121
-continued
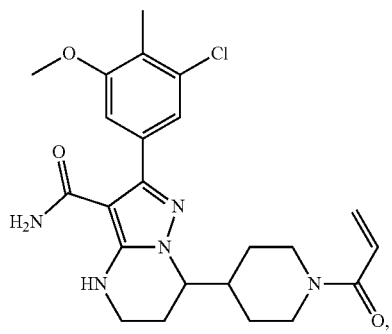
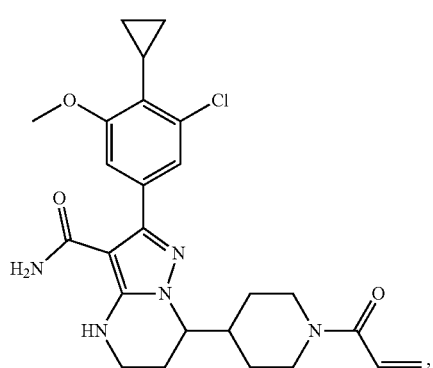
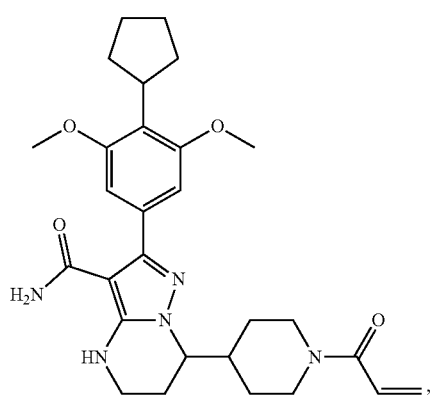
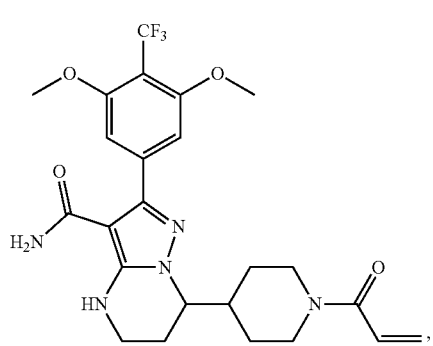
122
-continued
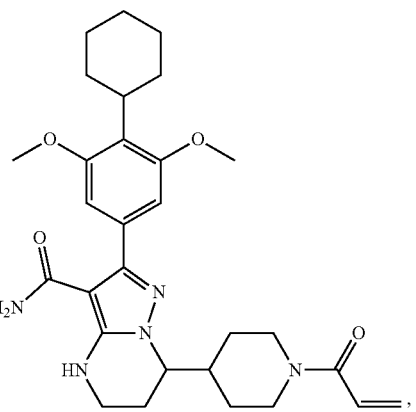
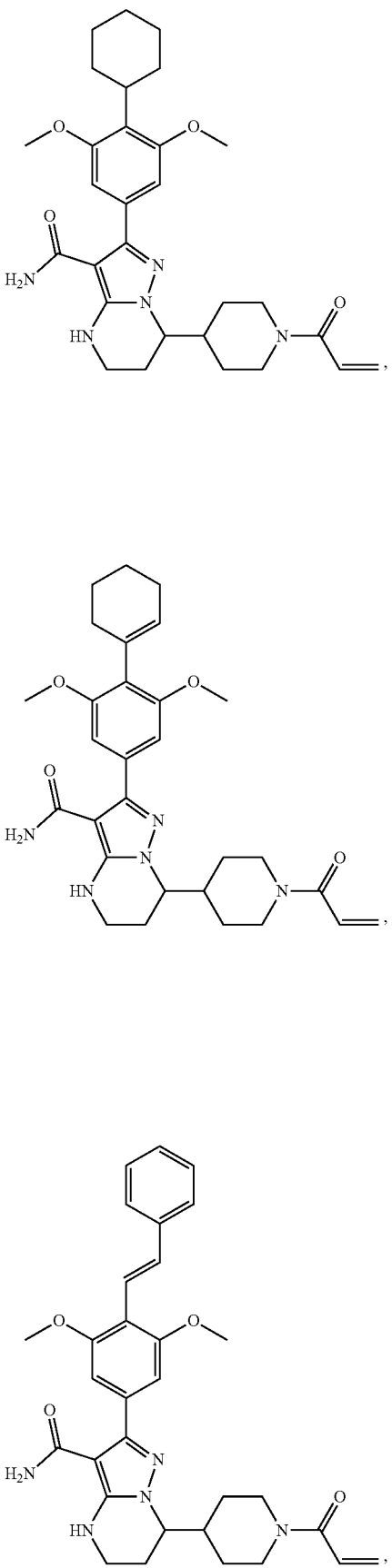

123
-continued
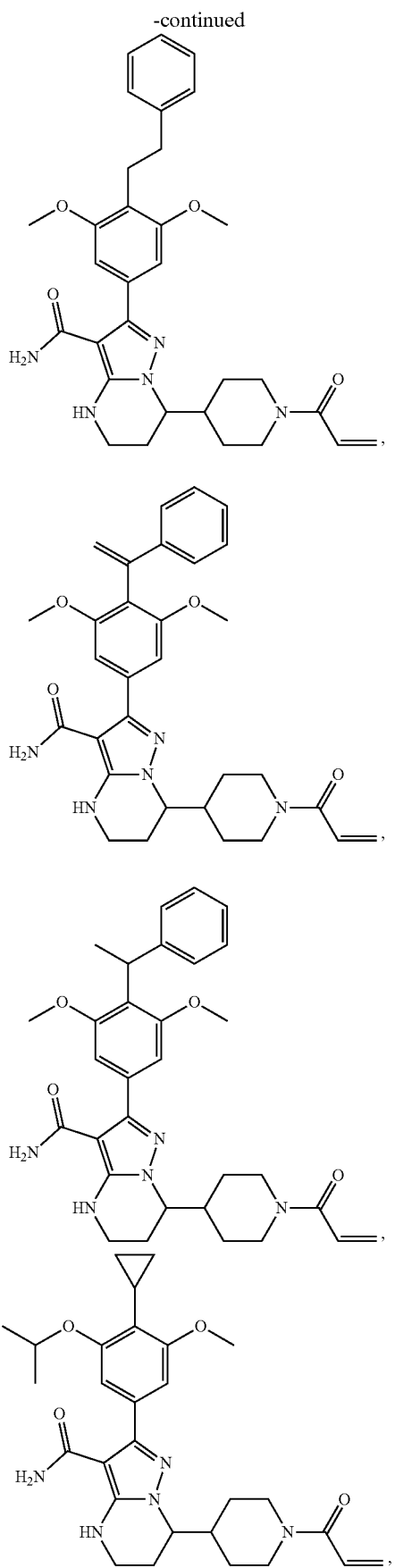
124
-continued
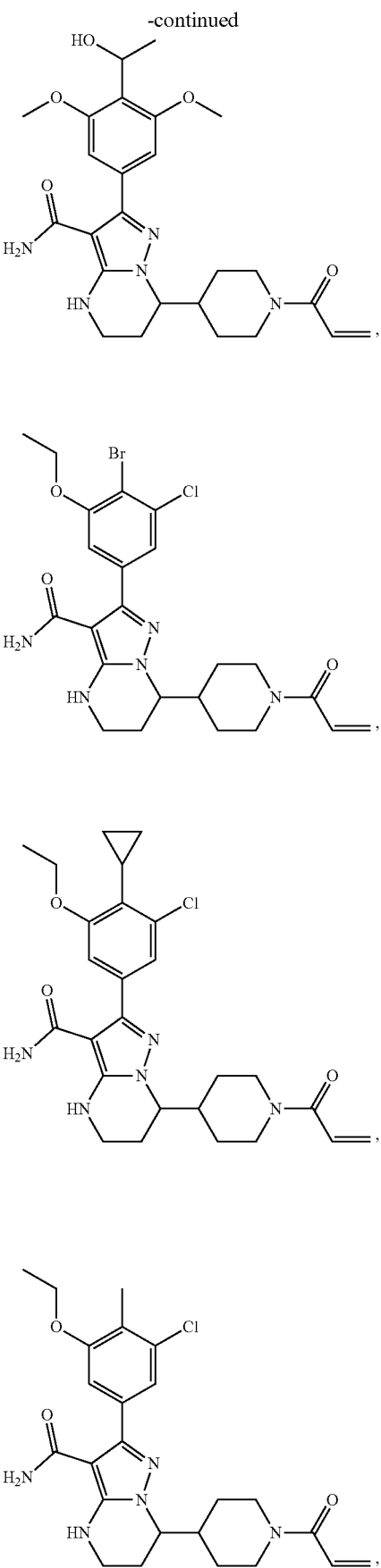

125
-continued
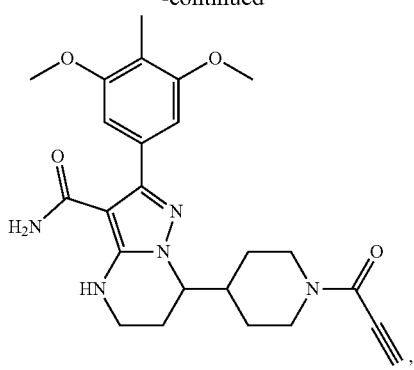
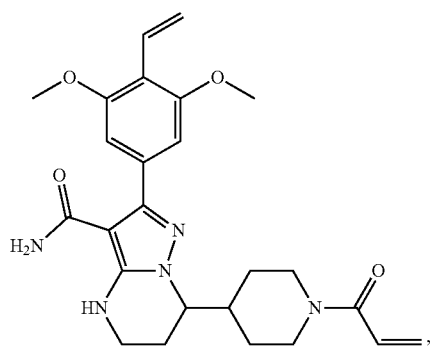
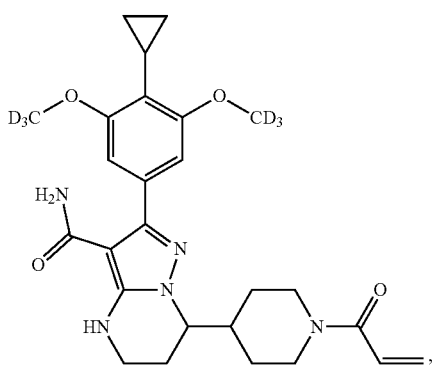
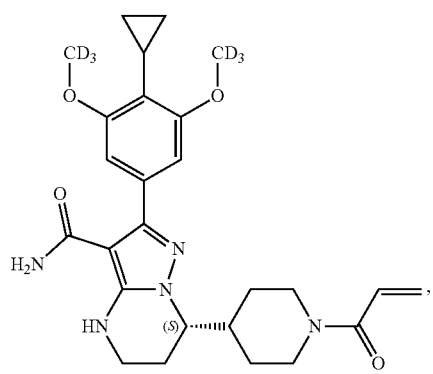
126
-continued
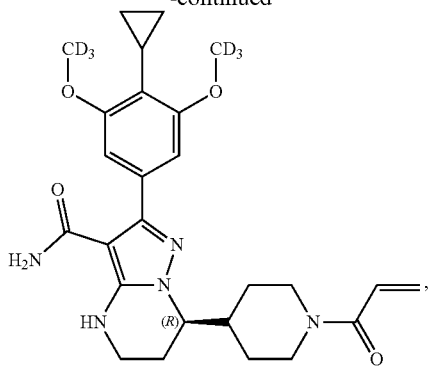
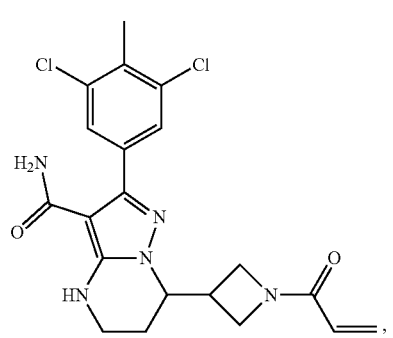
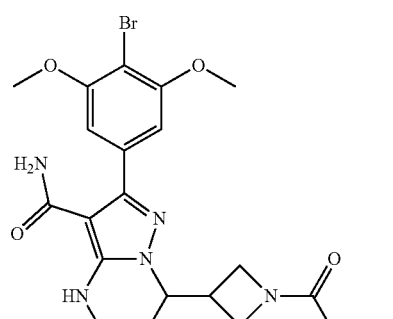
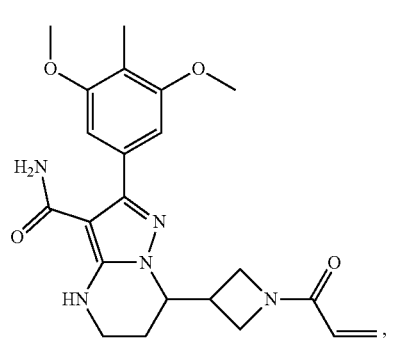

127 -continued
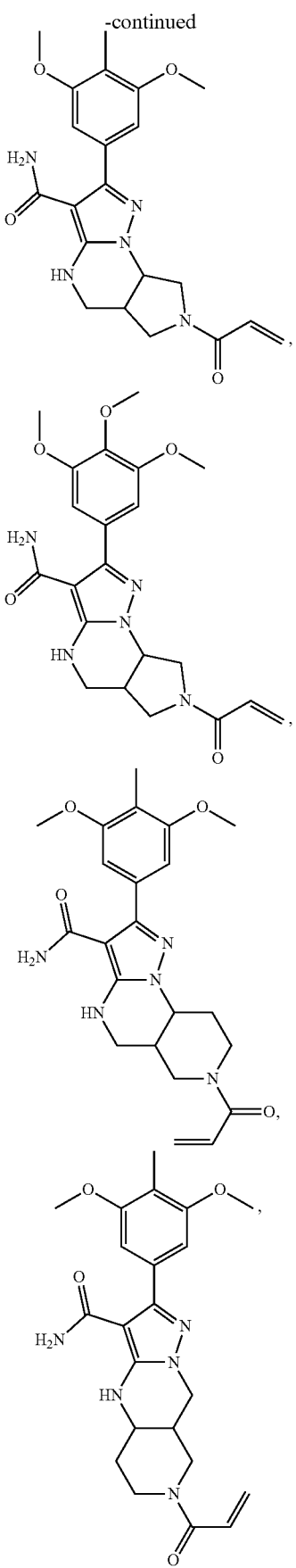
128 -continued
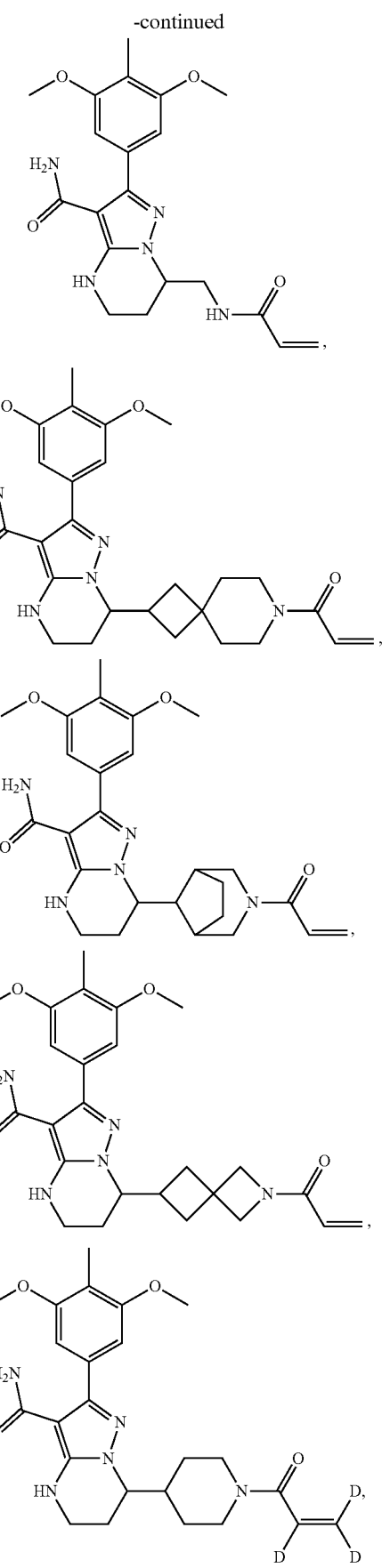

129
-continued
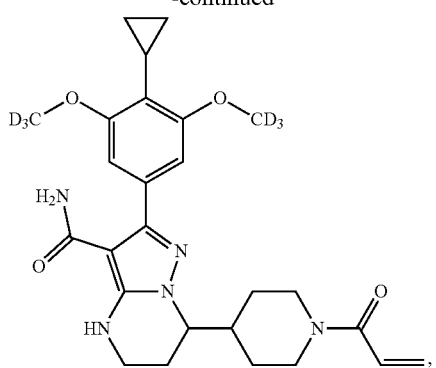
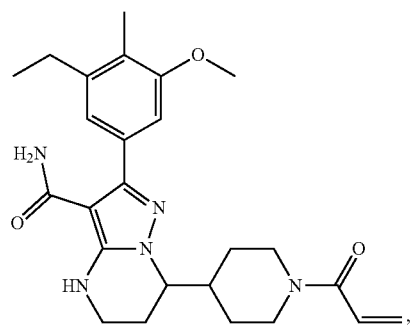
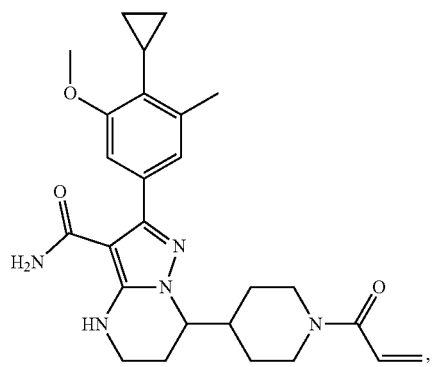
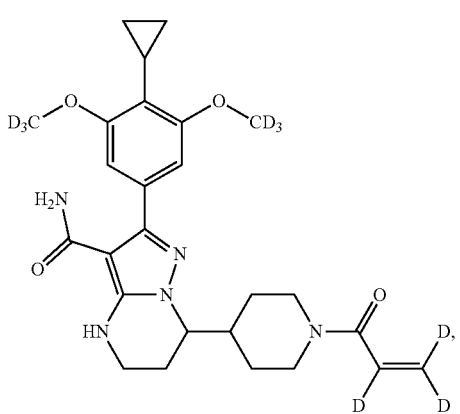
130
-continued
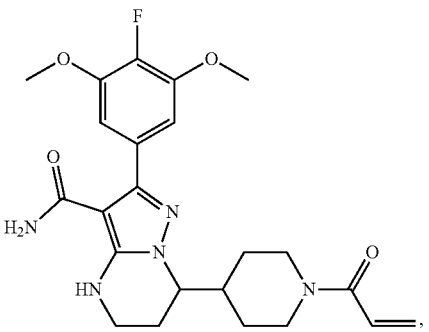
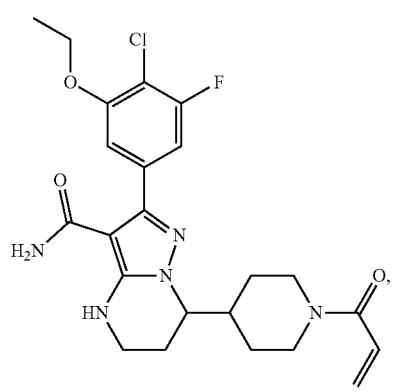
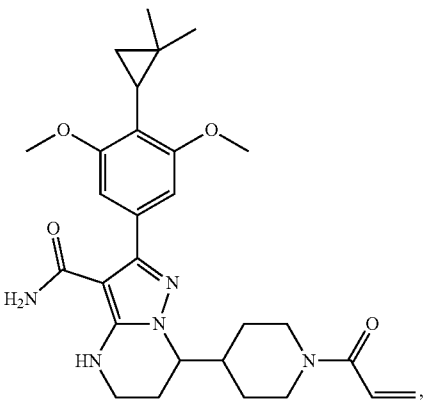
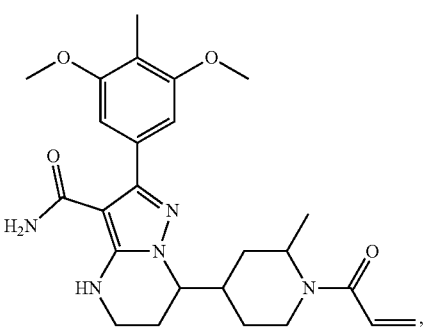

131
-continued

132
-continued

133
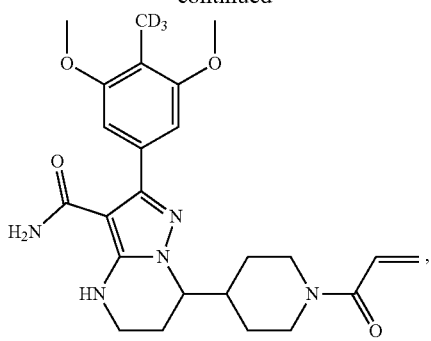
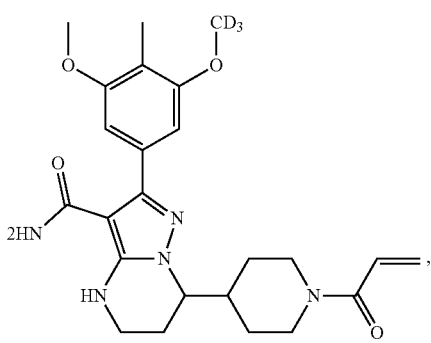
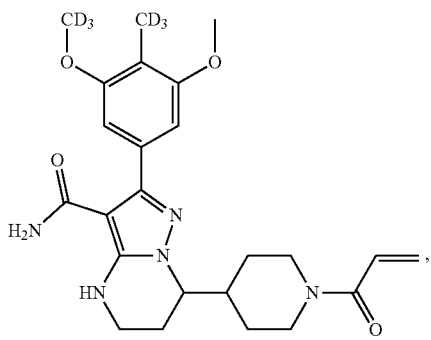
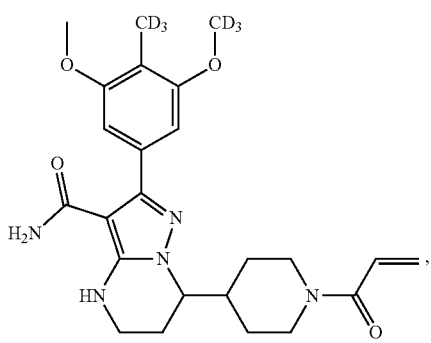
134
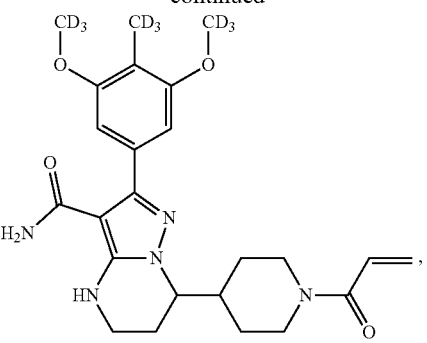
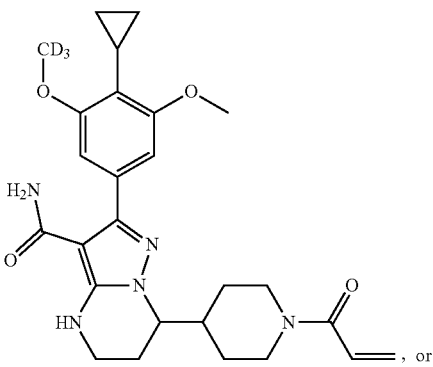
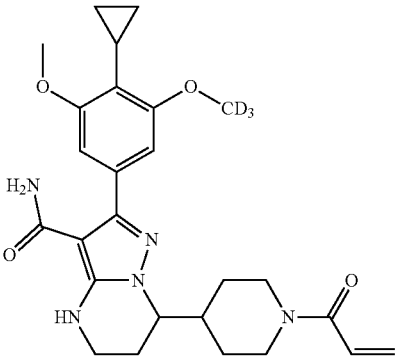
or a pharmaceutically acceptable salt thereof.
18. The compound of claim 3, wherein $R^1$ is alkyl or cycloalkyl.

19. The compound of claim 1, wherein the compound is:

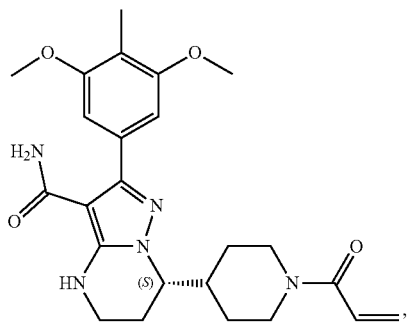

or a pharmaceutically acceptable salt thereof.

20. The compound of claim 1, wherein the compound is:

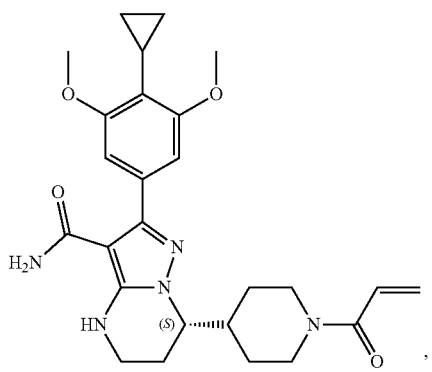

or a pharmaceutically acceptable salt thereof.

21. The compound of claim 1, wherein the compound is:

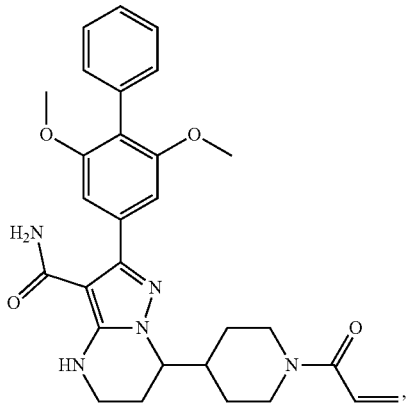 [SMILES: C=CC(=O)N1CCC(C2CCNc3c(C(N)=O)c(-c4cc(OC)c(-c5ccccc5)c(OC)c4)nn32)CC1]

or a stereoisomer thereof, or a pharmaceutically acceptable salt thereof.

22. The compound of claim 1, wherein the compound is:

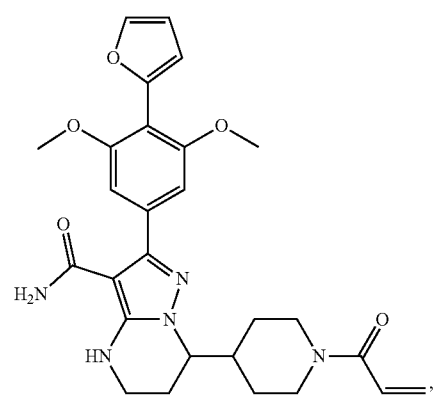 [SMILES: C=CC(=O)N1CCC(C2CCNc3c(C(N)=O)c(-c4cc(OC)c(-c5ccco5)c(OC)c4)nn32)CC1]

or a stereoisomer thereof, or a pharmaceutically acceptable salt thereof.

* * * * *

UNITED STATES PATENT AND TRADEMARK OFFICE
CERTIFICATE OF CORRECTION

PATENT NO. : 11,377,449 B2
APPLICATION NO. : 16/637615
DATED : July 5, 2022
INVENTOR(S) : Zhiwei Wang et al.

Page 1 of 1

It is certified that error appears in the above-identified patent and that said Letters Patent is hereby corrected as shown below:

In the Claims

In Claim 1, Column 109, Line 32, please replace "or ($R^{4a}$ and $R^{5b}$)," with --or ($R^{4b}$ and $R^{5b}$)--

In Claim 10, Column 110, Line 28, please replace "or ($R^{4a}$ and $R^{5b}$) or ($R^{4b}$ and $R^{5a}$)," with --or ($R^{4a}$ and $R^{5b}$), or ($R^{4b}$ and $R^{5a}$),--

In Claim 17, Column 114, Lines 42-54, please replace " 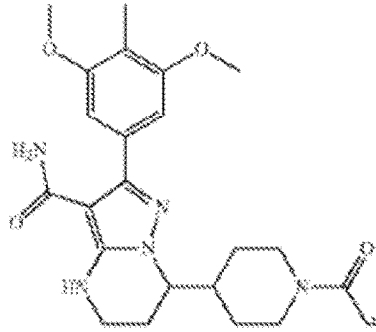 " with
 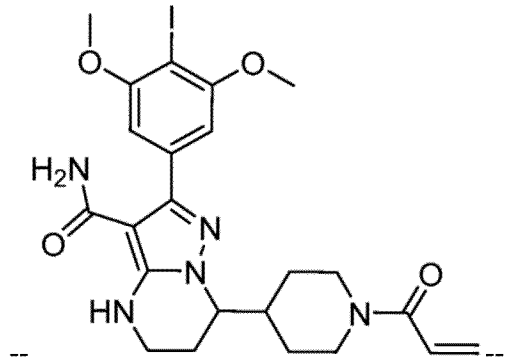 --

Signed and Sealed this
Thirty-first Day of January, 2023

Katherine Kelly Vidal
*Director of the United States Patent and Trademark Office*